United States Patent
Murray et al.

(10) Patent No.: US 6,306,586 B1
(45) Date of Patent: *Oct. 23, 2001

(54) METHODS AND COMPOSITIONS FOR THE DIAGNOSIS AND TREATMENT OF CATARACTS

(75) Inventors: Jeffrey C. Murray, Iowa City; Elena Semina, Coralville, both of IA (US)

(73) Assignee: University of Iowa Research Foundation, Iowa City, IA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/957,351

(22) Filed: Oct. 24, 1997

(51) Int. Cl.[7] .............................. C12Q 1/68; C12N 15/00; C12N 5/00; C07H 21/04
(52) U.S. Cl. ..................... 435/6; 435/320.1; 435/325; 536/23.1; 536/24.3
(58) Field of Search ........................... 435/6, 320.1, 325, 435/91.2; 536/23.1, 24.31

(56) References Cited

PUBLICATIONS

Semina et al.(1) "A novel homeobox gene PITX3 is mutated in families with autosomal–dominant cataracts ans ASMD" Nature Genetics; vol 19, pp. 167–170, Jun. 1998.*
Semina et al. (II) "Isolation of a new homeobox gene belonging to the Pitx/Rieg family: expression during lens development and mapping to the aphakia region on mouse chromosome 19" Human Molecular Genetics, vol.6, pp. 2109–2116, Nov. 5, 1997.*
Levitan, Max Textbook of Human Genetics, (3rd ed.) Oxford University Press, New York, 1988.*
D.H. Shlesinger (ed.) "Current methods in sequence comparison analysis" in Macromolecular Sequencing and Synthesis Selected Metho;DS and Applications, pp. 127–149, 1988.*
Kramer et al, "A Second Gene for Cerulean Cataracts Maps to the B crystallin Region on Chromosome 22" Genomics, vol. 35, pp 539–542, 1996.*
Semina et al., "Characterization of the PITX/RIEG homeobox–containing gene family and its involvement in the formation of anterior eye structures", Amer. J. of Human Gen., vol. 61, No. 4 suppl., Oct. 1997, p. a364, XP002098202.

International Search Report dated Apr. 13, 1999, for PCT US98/22689 filed Oct. 26, 1998.
Hittner, H. M. et al. (1982) "Variable Expressivity of Autosomal Dominant Anterior Segment Mesenchymal Dysgenesis in Six Generations" *Amer. Jour. Ophthal.* 93:57–70.
Jin, Y. et al. (1994) "Control of Type–D GABAergic Neuron Differentiation by C. elegans UNC–30 Homeodomain Protein" *Nature* 372:780–783.
Lamonerie, T. et al. (1996) "Ptx1, A Biocoid–related Homeo Box Transcription Factor Involved in Transcription of the Pro–Opiomelanocortin Gene" *Genes & Development* 10:1284–1295.
Semina, E.V. et al. (1996) "Cloning and Characterization of a Novel Biocoid–related Homeobox Transcription Factor Gene, RIEG, Involved in Rieger Syndrome" *Nat. Gen.* 14:392–399.
Szeto, D.P. et al. (1996) "P–OTX: A Pit–1–interacting Homeodomain Factor Expressed During Anterior Pituitary Gland Development" *Proc. Natl. Acad.* 93:7706–7710.
Marra et al., accession number AA062140, Sep. 23, 1996.*
Adams et al, accession number AA314048, Apr. 19, 1997.*
Mucchieli et al, accession number U80036, Sep. 23, 1996.*

* cited by examiner

*Primary Examiner*—W. Gary Jones
*Assistant Examiner*—Jehanne Souaya
(74) *Attorney, Agent, or Firm*—Beth E. Arnold; Isabelle M. Clauss; Foley, Hoag & Eliot LLP

(57) ABSTRACT

The invention provides nucleic acids encoding Pitx3 polypeptides, fragments thereof and homologs thereof and Pitx3 polypeptides encoded thereby. Pitx3 polypeptides play an important role in development of eye structures, e.g., the lens, and was shown herein to be associated with the formation of cataracts and Anterior Segment Mesenchymal Dysgenesis (ASMD). Thus, the invention provides methods for predicting whether a subject has or is at risk of developing cataracts or other disease associated with an aberrant Pitx3, by determining, e.g., whether the subject has a genetic lesion in a Pitx3 gene, such as a 17 bp insertion, characteristic of cataract development and ASMD or a base pair substitution at codon 13. Methods for treating cataracts or diseases or conditions associated with an aberrant Pitx3, e.g., by administering to the subject a Pitx3 therapeutic, are also disclosed, as well as assays for identifying Pitx3 therapeutics.

31 Claims, 7 Drawing Sheets

```
   1  TGCGGCCGCCCAGAGCAGGGGGCGGCCCACCCGCAGGGTGCCTGGCCCCTGGCCC
  56  CTGCCTGCGCTCCAGAACGCCGCCGCCACAGCCACCACCCGGAGTCTGCCTGCTG
 111  CGGGACGCACTAGACCTCCCTCCATGGAGTTTGGGCTGCTTGGTGAGGCAGAGGC
   1                                  M  E  F  G  L  L  G  E  A  E  A
 166  GCGAAGCCCTGCGCTGTCGTTATCGGACGCAGGCACTCCACACCCTCCGCTTCCA
  12     R  S  P  A  L  S  L  S  D  A  G  T  P  H  P  P  L  P
 221  GAACATGGCTGCAAGGGGCAGGAGCACAGTGACTCGGAGAAGGCCTCGGCCTCAC
  30     E  H  G  C  K  G  Q  E  H  S  D  S  E  K  A  S  A  S  L
 276  TGCCGGGGGGCTCCCCCGAGGACGGCTCTCTGAAGAAGAAGCAGCGGCGGCAGCG
  49        P  G  G  S  P  E  D  G  S  L  K  K  K  Q  R  R  Q  R
 331  CACGCACTTCACCAGCCAGCAGCTGCAGGAGCTGGAGGCCACCTTCCAGAGGAAT
  67        T  H  F  T  S  Q  Q  L  Q  E  L  E  A  T  F  Q  R  N
 386  CGCTACCCTGACATGAGCACCCGCGAAGAGATCGCGGTGTGGACCAACCTCACTG
  85        R  Y  P  D  M  S  T  R  E  E  I  A  V  W  T  N  L  T  E
 441  AGGCCCGCGTGCGGGTGTGGTTCAAGAACCGGCGCGCCAAGTGGCGGAAGCGGGA
 104        A  R  V  R  V  W  F  K  N  R  R  A  K  W  R  K  R  E
 496  GCGCAGCCAGCAGGCGGAGCTGTGCAAAGGTGGCTTCGCAGCCCCGCTCGGGGGC
 122     R  S  Q  Q  A  E  L  C  K  G  G  F  A  A  P  L  G  G
 551  CTGGTGCCACCCTACGAGGAGGTGTACCCGGGCTACTCGTACGGCAACTGGCCGC
 140     L  V  P  P  Y  E  E  V  Y  P  G  Y  S  Y  G  N  W  P
 606  CCAAGGCTCTCGCCCCGCCGCTCGCCGCCAAGACCTTCCCGTTCGCCTTCAACTC
 159     K  A  L  A  P  P  L  A  A  K  T  F  P  F  A  F  N  S
 661  GGTCAACGTGGGGCCTCTGGCTTCACAGCCTGTATTCTCACCGCCCAGCTCCATC
 177     V  N  V  G  P  L  A  S  Q  P  V  F  S  P  P  S  S  I
 716  GCCGCTTCTATGGTGCCCTCGGCCGCCGCTGCCCCGGGCACCGTACCAGGTCCCG
 195     A  A  S  M  V  P  S  A  A  A  A  P  G  T  V  P  G  P  G
 771  GAGCCTTGCAGGGCCTGGGCGGGGCACCCCCGGGCTGGCTCCAGCCGCCGTGTC
 214     A  L  Q  G  L  G  G  A  P  P  G  L  A  P  A  A  V  S
 825  CTCCGGGGCAGTGTCCTGCCCTTACGCCTCGGCCGCCGCAGCCGCCGCTGCAGCC
 232     S  G  A  V  S  C  P  Y  A  S  A  A  A  A  A  A  A  A
 881  GCCTCCTCCCCCTATGTATACCGGGACCCGTGTAACTCGAGCCTGGCTAGCCTGC
 250     A  S  S  P  Y  V  Y  R  D  P  C  N  S  S  L  A  S  L  R
 936  GGCTCAAAGCCAAGCAGCACGCCTCTTTCAGCTATCCCGCCGTGCCCGGGCCGCC
 269        L  K  A  K  Q  H  A  S  F  S  Y  P  A  V  P  G  P  P
 991  GCCGGCCGCTAACCTTAGCCCCTGCCAGTACGCCGTGGAACGGCCGGTGTGAGCC
 287     P  A  A  N  L  S  P  C  Q  Y  A  V  E  R  P  V
1046  GCAGGTCTGTGGATCCATCCCCGAGGGCGGGGCAGTAATTCACAGCCTCTCCGGA
1101  CAGGGGTCGCCTAGACTGGCTTGCCCTCGTCCCAGGGTCTGAAAGGGGTGCCAGA
1156  GCACCCGGGAAGAGGCCGCGGGCTTCGAAGAGGGCCTTTTCCCTCGCAGCCCCCG
1211  AGCGGTGGTCTGACCCCTATGCGGAGACCGCGCCCCTAGGACTAAGGCCAGGAAC
1266  AGGGACCAGCTCCCCCAGGGCCAATTCACCCTTGGCTCACCCCGCCTTCTCCAGA
1321  CTCCCCCTATCCCATTTTCAAAGATCAATGAAATAAACGTGCGCGGACTGTCAAA
1376  AAAAAAAAAAAAAAAAA
```

FIG. 1

```
                   1               15 16                          30 31                45 46                     60 61                75 76                    90
Ptx1/Potx  MDAFKGGMSLERLPE GLRPPPPPPHDMGPS FHIARAADPREPLEN SASESSDADL-PDKE RGEAKGPEDG-GAG SAGCGGGAEDPAKKK   88
Pitx2/Riegl  -------------   --------------- ---------MET NCRKLVSACVQLEKD KQQGK-NED----- ----VGAEDPSKKK   37
Pitx3      -------------   --------MEF GLEGEAEARSPALSL EDAGTPHPELP----E HGCKGQEHSDSEKAS ASLPGGSPEDGSLKK   60

91              105 106                        120 121                135 136                 150 151                165 166                180
Ptx1/Potx  KQRRQRTHFTSQQLQ ELEATFQRNRYPDMS MREEIAVWTNLTEPR VRVWFKNRRAKWRKR ERNQQLDLCKCCIVP QFSGLVQPYEDVYAA  178
Pitx2/Riegl RQRRQRTHFTSQQLQ ELEATFQRNRYPDMS TREEIAVWTNLTEAR VRVWEKNRRAKWRKR ERNQQXELCK-GFGP QFNGIMPPYDDMY-P  126
Pitx3      KQRRQRTHFTSQQLQ ELEATFQRNRYPDMS TREEIAVWTNLTEAR VRVWFKNRRAKWRKR ERSQQAELCKGGFAA PLGGLVPPYEEVY-P  149

181              195 196                        210 211                225 226                 240 241                255 256                270
Ptx1/Potx  GYSYNNWAAKSLAPA PLSTKSFIF-FNSM- -SPLSSQSMFSAPSS I-SSMTMPSSMQPGA VPGMPNS---GLNNL NNITGSSLNSAMSPG  261
Pitx2/Riegl GYSYNNWAAKGLTSA SLSTKSFPF-FNSMN VNPLSSQSMFSPPNS I-SSMSMSSSMVPSA VTGMPGSSLNSLNNL NNLSSPSLNSAVTP   214
Pitx3      GYSYGNWPPKALAP- PLAAKTEPFAFNSVN VGPLASQFVESPPSS IAASMVPSAAAAPGT VPG-PG--ALQGL-- GGAPPGLAPAAVSSG  233

271              285 286                        300 301                315 316                 330 331                345
Ptx1/Potx  A--CPY------- -G TPASPYSVYRDTCNS SLASLRLKSKQHSSF GYGGL--QGPASGIN ACQYNS-----     315
Pitx2/Riegl A--CPY------- -A PPTPPY-VYRDTCNS SLASLRLKAKQHSSF GYASV--QNPASNLS ACQYAVDRPV       271
Pitx3      AVSCPYASAAAAAA AASSPY-VYRDPCNS SLASLRLKAKQHASF SVPAVPGPPPAANLS PCQYAVERPV       302
```

FIG. 2

```
  1  TCCATGGAGTTCGGCCTGCTCAGCGAGGCAGAGGCCCGGAGCCCTGCCCTGT
  1    M  E  F  G  L  L  S  E  A  E  A  R  S  P  A  L  S
 53  CGCTGTCAGACGCTGGCACTCCGCACCCCCAGCTCCCAGAGCACGGCTGCAA
 18   L  S  D  A  G  T  P  H  P  Q  L  P  E  H  G  C  K
105  GGGCCAGGAGCACAGCGgtaagcgcgccccttccgggggtgcaggacataa
 35   G  Q  E  H  S  D
     cagcttcatccc..ggagaatatgcgctggcttgggcgctctgtgacctgcc 122  cccaccctggcccccagACTCAGAAAAGGCCTCGGCTTCGCTGCCCGGCGGC
 41                    S  E  K  A  S  A  S  L  P  G  G
157  TCCCCAGAGGACGGTTCGCTGAAAAAGAAGCAGCGGCGGCAGCGCACGCACT
 52   S  P  E  D  G  S  L  K  K  K  Q  R  R  Q  R  T  H  F
209  TCACCAGCCAGCAGCTACAGGAGCTAGAGGCGACCTTCCAGAGGAACCGCTA
 70   T  S  Q  Q  L  Q  E  L  E  A  T  F  Q  R  N  R  Y
261  CCCCGACATGAGCACGCGCGAGGAGATCGCCGTGTGGACAAACCTCACCGAGG
 87   P  D  M  S  T  R  E  E  I  A  V  W  T  N  L  T  E  A
313  CCCGCGTGCGGtatgctctccagacccgcgactcgcacccgcgcgggccctc
105   R  V  R
     cgcgctcagcct....gctgggacccggccccgggccctgaccgcctttctcc 324  cgtgcccgcagGTGTGGTTCAAGAACCGGCGCGCCAAATGGCGGAAGCGCGAG
108              V  W  F  K  N  R  R  A  K  W  R  K  R  E
365  CGCAGCCAGCAGGCCGAGCTATGCAAAGGCAGCTTCGCGGCGCCGCTCGGGGG
122   R  S  Q  Q  A  E  L  C  K  G  S  F  A  A  P  L  G  G
417  GCTGGTGCCGCCCTACGAGGAGGTGTACCCCGGCTACTCGTACGGCAACTGGC
140   L  V  P  P  Y  E  E  V  Y  P  G  Y  S  Y  G  N  W  P
469  CGCCCAAGGCTCTTGCCCCGCCGCTCGCCGCCAAGACCTTTCCATTCGCCTTC
158    P  K  A  L  A  P  P  L  A  A  K  T  F  P  F  A  F
521  AACTCGGTCAACGTGGGGCCTCTGGCTTCGCAGCCCGTCTTCTCGCCACCCAG
175   N  S  V  N  V  G  P  L  A  S  Q  P  V  F  S  P  P  S
573  CTCCATCGCCGCCTCCATGGTGCCCTCCGCCGCGGCTGCCCCGGGCACCGTGC
193    S  I  A  A  S  M  V  P  S  A  A  A  A  P  G  T  V  P
625  CAGGGCCTGGGGCCCTGCAGGGCCTGGGCGGGGGCCCCCCCGGGCTGGCTCCG
211    G  P  G  A  L  Q  G  L  G  G  G  P  P  G  L  A  P
677  GCCGCCGTGTCCTCCGGGGCCGTGTCCTGCCCTTATGCCTCGGCCGCCGCCGC
228  A  A  V  S  S  G  A  V  S  C  P  Y  A  S  A  A  A  A
729  CGCCGCGGCTGCCGCCTCTTCCCCCTACGTCTATCGGGACCCGTGTAACTCGA
246   A  A  A  A  A  S  S  P  Y  V  Y  R  D  P  C  N  S  S
781  GCCTGGCCAGCCTGCGGCTCAAAGCCAAACAGCACGCCTCCTTCAGCTACCCC
264   L  A  S  L  R  L  K  A  K  Q  H  A  S  F  S  Y  P
833  GCTGTGCACGGGCCGCCCCCGGCAGCCAACCTTAGTCCGTGCCAGTACGCCGT
281   A  V  H  G  P  P  P  A  A  N  L  S  P  C  Q  Y  A  V
885  GGAAAGGCCCGTATGAGCGGCCCCGCCCGTAGATCATCCCCGAGGGCGGGGGC
299   E  R  P  V
937  AACGATTCACAGCCTCCGCGGACTGGGGTCATTTTGACTGGCTTGCTCCCGCC
989  CCAGGGTCTGAAAGG
```

FIG. 3

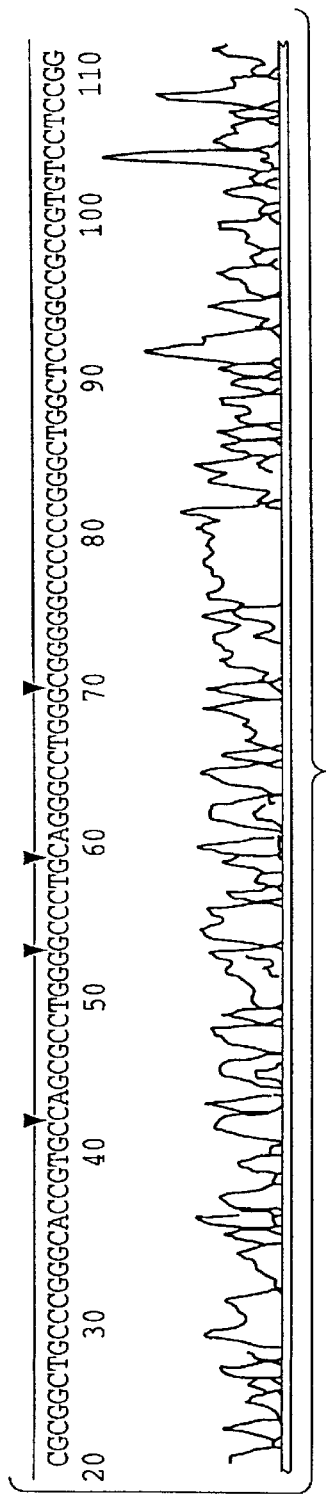
FIG. 4A
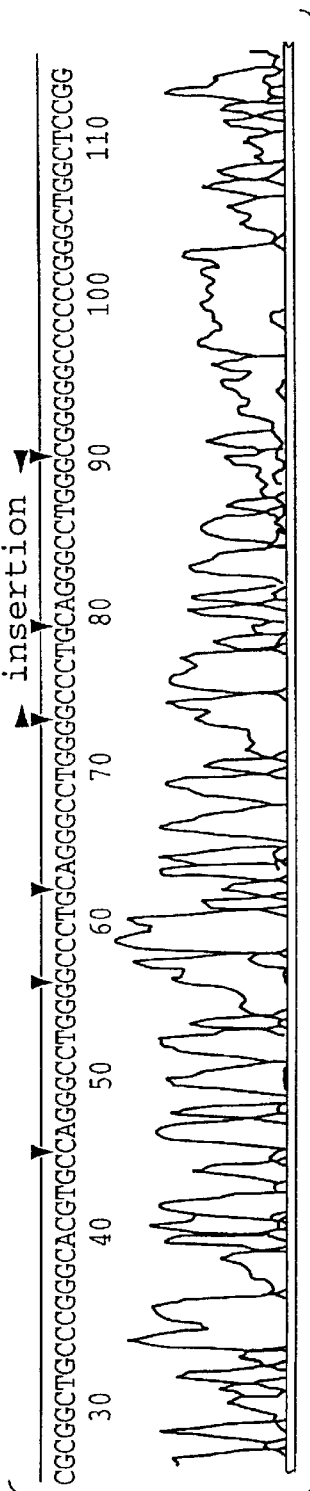
FIG. 4B
| Codon | 210 211 212 | 213 214 215 | 216 217 218 | 219 220 221 | ...302......314 |
|---|---|---|---|---|---|
| Normal | C[CA GGG CCT GGG] | GCC CTG | [CAG GGC CTG GG]C | GGG GGC | ..........STOP |
| | P G P G | A L | Q G L G | G G | |
| Mutant (ASMD) | C[CA GGG CCT GGG] | GCC CTG | [CAG GGC CTG GG]G | CCC TG[C AGG GCC TGG G]CG | insertion frame shift .....STOP |
| | P G P G | A L | Q G L G | P C R A W A | |
FIG. 4C

```
1    TCCATGGAGTTCGGCCTGCTCAGCGAGGCAGAGGCCCGGAGCCCTGCCCTGT
1     M  E  F  G  L  L  S  E  A  E  A  R  S  P  A  L  S
53   CGCTGTCAGACGCTGGCACTCCGCACCCCCAGCTCCCAGAGCACGGCTGCAA
18    L  S  D  A  G  T  P  H  P  Q  L  P  E  H  G  C  K
105  GGGCCAGGAGCACAGCGgtaagcgcgccccttccgggggtgcaggacataa
35    G  Q  E  H  S  D
     cagcttcatccc..ggagaatatgcgctggcttgggcgctctgtgacctgcc 122  cccaccctggcccccagACTCAGAAAAGGCCTCGGCTTCGCTGCCCGGCGGC
41                    S  E  K  A  S  A  S  L  P  G  G
157  TCCCCAGAGGACGGTTCGCTGAAAAAGAAGCAGCGGCGGCAGCGCACGCACT
52    S  P  E  D  G  S  L  K  K  Q  R  R  Q  R  T  H  F
209  TCACCAGCCAGCAGCTACAGGAGCTAGAGGCGACCTTCCAGAGGAACCGCTA
70    T  S  Q  Q  L  Q  E  L  E  A  T  F  Q  R  N  R  Y
261  CCCCGACATGAGCACGCGCGAGGAGATCGCCGTGTGGACAAACCTCACCGAGG
87    P  D  M  S  T  R  E  E  I  A  V  W  T  N  L  T  E  A
313  CCCGCGTGCGGgtatgctctccagacccgcgactcgcacccgcgcgggccctc
105   R  V  R
     cgcgctcagcct....gctgggacccggccccgggccctgaccgcctttctcc 324  cgtgcccgcagGTGTGGTTCAAGAACCGGCGCGCCAAATGGCGGAAGCGCGAG
108              V  W  F  K  N  R  R  A  K  W  R  K  R  E
365  CGCAGCCAGCAGGCCGAGCTATGCAAAGGCAGCTTCGCGGCGCCGCTCGGGGG
122   R  S  Q  Q  A  E  L  C  K  G  S  F  A  A  P  L  G  G
417  GCTGGTGCCGCCCTACGAGGAGGTGTACCCCGGCTACTCGTACGGCAACTGGC
140   L  V  P  P  Y  E  E  V  Y  P  G  Y  S  Y  G  N  W
469  CGCCCAAGGCTCTTGCCCCGCCGCTCGCCGCCAAGACCTTTCCATTCGCCTTC
158   P  K  A  L  A  P  P  L  A  A  K  T  P  P  F  A  F
521  AACTCGGTCAACGTGGGGCCTCTGGCTTCGCAGCCCGTCTTCTCGCCACCCAG
175  N  S  V  N  V  G  P  L  A  S  Q  P  V  F  S  P  P  S
573  CTCCATCGCCGCCTCCATGGTGCCCTCCGCCGCGGCTGCCCCGGGCACCGTGC
193   S  I  A  A  S  M  V  P  S  A  A  A  A  P  G  T  V  P
625  CAGGGCCTGGGGCCCTGCAGGGCCTGGGGCCCTGCAGGGCCTGGGCGGGGGCC
211   G  P  G  A  L  Q  G  L  G  P  C  R  A  W  A  G  A
677  CCCCGGGCTGGCTCCGGCCGCCGTGTCCTCCGGGGCCGTGTCCTGCCCTTAT
228  P  P  G  W  L  R  P  P  C  P  P  G  P  C  P  A  L  M
729  GCCTCGGCCGCCGCCGCCGCCGCGGCTGCCGCCTCTTCCCCCTACGTCTATCG
246   P  R  P  P  P  P  P  R  L  P  P  L  P  P  T  S  I  G
781  GGACCCGTGTAACTCGAGCCTGGCCAGCCTGCGGCTCAAAGCCAAACAGCACG
264   T  R  V  T  R  A  W  P  A  C  G  S  K  P  N  S  T
833  CCTCCTTCAGCTACCCCGCTGTGCACGGGCCGCCCCCGGCAGCCAACCTTAGT
281  P  P  S  A  T  P  L  C  T  G  R  P  R  O  P  T  L  V
885  CCGTGCCAGTACGCCGTGGAAAGGCCCGTATGAGCGGCCCCGCCCGTAGATCAT
299   R  A  S  T  P  W  K  G  P  Y  E  R  P  R  P  STOP
937  CCCCGAGGGCGGGGGCAACGATTCACAGCCTCCGCGGACTGGGGTCATTTTGAC
989  TGGCTTGCTCCCGCCCCAGGGTCTGAAAGG
```

FIG. 5

```
  1    TCCATGGAGTTCGGCCTGCTCAGCGAGGCAGAGGCCCGGACCCCTGCCCTGT
  1      M  E  F  G  L  L  S  E  A  E  A  R  N  P  A  L  S
 53    CGCTGTCAGACGCTGGCACTCCGCACCCCCAGCTCCCAGAGCACGGCTGCAA
 18     L  S  D  A  G  T  P  H  P  Q  L  P  E  H  G  C  K
105    GGGCCAGGAGCACAGCGgtaagcgcgccccttccgggggtgcaggacataa
 35     G  Q  E  H  S  D
       cagcttcatccc..ggagaatatgcgctggcttgggcgctctgtgacctgcc 122    cccaccctggcccccagACTCAGAAAAGGCCTCGGCTTCGCTGCCCGGCGGC
 41                    S  E  K  A  S  A  S  L  P  G  G
157    TCCCCAGAGGACGGTTCGCTGAAAAAGAAGCAGCGGCGGCAGCGCACGCACT
 52     S  P  E  D  G  S  L  K  K  K  Q  R  R  Q  R  T  H  F
209    TCACCAGCCAGCAGCTACAGGAGCTAGAGGCGACCTTCCAGAGGAACCGCTA
 70       T  S  Q  Q  L  Q  E  L  E  A  T  F  Q  R  N  R  Y
261    CCCCGACATGAGCACGCGCGAGGAGATCGCCGTGTGGACAAACCTCACCGAGG
 87     P  D  M  S  T  R  E  E  I  A  V  W  T  N  L  T  E  A
313    CCCGCGTGCGGgtatgctctccagacccgcgactcgcacccgcgcgggccctc
105      R  V  R
       cgcgctcagcct....gctgggacccggccccgggccctgaccgccttttctcc 324    cgtgcccgcagGTGTGGTTCAAGAACCGGCGCGCCAAATGGCGGAAGCGCGAG
108                   V  W  F  K  N  R  R  A  K  W  R  K  R  E
365    CGCAGCCAGCAGGCCGAGCTATGCAAAGGCAGCTTCGCGGCGCCGCTCGGGGG
122     R  S  Q  Q  A  E  L  C  K  G  S  F  A  A  P  L  G  G
417    GCTGGTGCCGCCCTACGAGGAGGTGTACCCCGGCTACTCGTACGGCAACTGGC
140     L  V  P  P  Y  E  E  V  Y  P  G  Y  S  Y  G  N  W  P
469    CGCCCAAGGCTCTTGCCCCGCCGCTCGCCGCCAAGACCTTTCCATTCGCCTTC
158     P  K  A  L  A  P  P  L  A  A  K  T  F  P  F  A  F
521    AACTCGGTCAACGTGGGGCCTCTGGCTTCGCAGCCCGTCTTCTCGCCACCCAG
175     N  S  V  N  V  G  P  L  A  S  Q  P  V  F  S  P  P  S
573    CTCCATCGCCGCCTCCATGGTGCCCTCCGCCGCGGCTGCCCCGGGCACCGTGC
193     S  I  A  A  S  M  V  P  S  A  A  A  A  P  G  T  V  P
625    CAGGGCCTGGGGCCCTGCAGGGCCTGGGCGGGGGCCCCCCCGGGCTGGCTCCG
211     G  P  G  A  L  Q  G  L  G  G  G  P  P  G  L  A  P
677    GCCGCCGTGTCCTCCGGGGCCGTGTCCTGCCCTTATGCCTCGGCCGCCGCCGC
228     A  A  V  S  S  G  A  V  S  C  P  Y  A  S  A  A  A  A
729    CGCCGCGGCTGCCGCCTCTTCCCCCTACGTCTATCGGGACCCGTGTAACTCGA
246     A  A  A  A  S  S  P  Y  V  Y  R  D  P  C  N  S  S
781    GCCTGGCCAGCCTGCGGCTCAAAGCCAAACAGCACGCCTCCTTCAGCTACCCC
264     L  A  S  L  R  L  K  A  K  Q  H  A  S  F  S  Y  P
833    GCTGTGCACGGGCCGCCCCCGGCAGCCAACCTTAGTCCGTGCCAGTACGCCGT
281     A  V  H  G  P  P  P  A  A  N  L  S  P  C  Q  Y  A  V
885    GGAAAGGCCCGTATGAGCGGCCCCGCCCGTAGATCATCCCCGAGGGCGGGGC
299     E  R  P  V
937    AACGATTCACAGCCTCCGCGGACTGGGGTCATTTTGACTGGCTTGCTCCCGCC
989    CCAGGGTCTGAAAGG
```

FIG. 6

METHODS AND COMPOSITIONS FOR THE DIAGNOSIS AND TREATMENT OF CATARACTS

GOVERNMENT SUPPORT

This invention was made during work supported by NIH grant DE-09170. The U.S. Government therefore may have certain rights in the invention.

BACKGROUND OF THE INVENTION

A cataract is any clouding or haziness in the eye's natural lens. Most cataracts develop as part of the normal aging process, from a change in the internal composition of the natural lens. They are extremely common, since anyone living beyond 60 or 70 years will most certainly develop cataracts. About 70% of persons over the age of 75 have visually significant cataracts. Cataracts resulting from the aging process usually develop in both eyes, but often at different rates. While most kinds of cataracts progress slowly over several years, a cataract may progress rapidly over several months producing a significant decrease in vision in the affected eye.

Certain types of cataracts are developmental or congenital and are present at birth. These can be due to chromosomal abnormalities. Furthermore, certain diseases can be associated with the development of cataracts. For example, the autosomal dominant disease termed Anterior Segment Mesenchymal Dystrophy (ASMD), is a disease associated with an anterior segment abnormality in which each individual affected develops cataracts, even at an early age (Hittner et al. (1982) *Am. J. Ophthal.* 93:57). This disease is also associated with strong defects in visual acuity, corneal opacities, lens opacities, optic nerve abnormalities, and the development of glaucoma.

At present, the only way to restore visual loss from cataracts is surgical removal of the cloudy lens. Although most patients benefit from cataract surgery with improved eyesight, this in not true for everyone. Some people do not have sharp eyesight after the surgery due to other eye diseases such as glaucoma and macular degeneration. As with all surgical operations, sometimes complications can occur resulting in reduced vision post-operatively or even rarely blindness. Thus, it is highly desirable to develop methods for preventing cataracts and methods for treating cataracts which are less invasive.

The development of the lens is a well-studied process and includes several stages. The formation of the lens placode (by 10-dpc in mouse embryo) is induced by the neuroepithelium of the optic vesicle after establishment of close contact between the optic vesicle and overlying surface ectoderm at day 9.5–9.75 pc (Zwaan, J. (1975) *Dev. Biol.* 44(2): 306–312; Kaufman, M. H. (1992) *The atlas of mouse development.* Academic Press, London). The lens placode starts to invaginate in the 10.5-dpc embryo and the lens cup rapidly deepens within the next few hours. The closure of the lens cup and detachment of the lens vesicle from the surface occur by day 11–11.25 pc. At day 11.5 pc the formation of lens fibers begins, with continued elongation of the fibers leading to occlusion of the lens cavity before the end of day 13 pc. By day 13 the lens has a similar configuration to that of the adult organ (Zwaan, J. (1975) supra; Kaufman, M. H. (1 992) supra).

During, lens development the peripheral epithelial cells proliferate anterior to the lens equator (or bow region), where they subsequently differentiate into the lens fiber cells. Differentiation into lens fiber cells includes cell elongation and loss of subcellular organelles, cessation of DNA replication and of cell division and synthesis of fiber cell-specific proteins such as various crystallins (Reneker, L. W. and Overbeek, P. A. (1996) *Dev. Biol.* 180(2): 554–565).

Many genes are involved in lens formation. Pax-6, a master gene in eye development, has been implicated in the various mouse and rat Small eye (Sey) mutant phenotypes (Hill, R. E., et al. (1991) *Nature* 354(6354):522–525) as well as in human aniridia (Jordan, T., et al. (1992) *Nature Genet.* 1(5):328–332). Pax6 is expressed in all stages of lens development. A histologic analysis of the murine homozygous Sey mutants revealed that the optic vesicles grow out but there is no lens induction (Hogan, B. L., et al. (1988) *Development* 103 Suppl. 115–119). Tissue transplantation experiments in a rat Sey mutant demonstrated that homozygous rSey ectoderm loses its lens-forming competence early in development (Graw, J. (1996) *Dev. Genet.*18(3):181–197). Several papers have demonstrated that Pax6 is involved in the regulation of lens-specific expression of the crystallin genes (Cvekl, A. and Piatigorsky, J. (1996) *Bioessays* 18(8):621–630). These results suggest that Pax-6 is involved in lens induction and subsequent development and differentiation.

Other homeobox genes involved in early lens development include Prox1 (related to Drosophila prospero), which is expressed in the early lens placode and later throughout the lens, especially in the bow region, in chicken (Zinovieva, R. D., et al, (1996) *Genomics* 35(3): 517–522), and in the developing lens in mouse (Oliver, G., et al. (1993) *Mech. Dev.* 14(1):3–16) and human (Zinovieva, R. D., et al. (1996) supra). Murine Six3 is expressed in the optic vesicle and lens (Oliver, G., et al, (1995) *Development* 121(12):4045–4055). In Xenopus, the Six3 transcript was detected in the anterior neural plate, a region involved in lens induction. The ectopic expression of murine Six3 in fish embryos resulted in ectopic lens formation in the area of the otic vesicle (Oliver, G., et al, (1996) *Mech. Dev.* 60(2):233–239). Chicken GH6 is expressed in the lens epithelium at stage 23, which is roughly equivalent to mouse day 11 pc (Stadler, H. S. and Solursh, M. (1994) *Dev. Biol.* 151(1):251–262). Mouse Msx2 and Emx1 are expressed in the lens, as reviewed by Beebe (Beebe, D. C. (1994) *Invest. Ophthalmal. Vix. Sci.* 35:2897–2900). In addition, some Sox homeodomain proteins have been shown to be involved in lens-specific activation of crystallin genes in mouse (Kamachi, Y., et al, (1995) *EMBO J.* 15:3510–3519).

However, none of these genes have been involved in the development of cataracts. It would be highly desirable to isolate genes which are associated with ocular diseases or disorders, such as cataracts and which would thus provide diagnostic and therapeutic methods. In particular, therapeutic methods less intrusive than surgery could be developed.

SUMMARY OF THE INVENTION

The invention is based at least in part on the isolation of DNA molecules encoding Pitx3 polypeptides, such as human and mouse Pitx3 polypeptides. As described herein, Pitx3 proteins are homeobox containing proteins, which are involved in the development of the lens and contribute to diseases and disorders of the lens, such as cataracts. In fact, as shown herein, a mutated form of Pitx3 having a different C-terminal sequence from that of the wild-type Pitx3 protein (shown in FIGS. 4 and 5) was found in all affected individuals of a family carrying the disorder Anterior Segment Mesenchymal Dysgenesis (ASMD), all of which have cataracts. Furthermore, another mutation, i.e., an amino acid substitution in the N-terminus of the protein (shown in FIG. 6) was found in an individual having congenital cataract, but not in control individuals. In addition, Pitx3 is expressed predominantly in the lens during embryonic development and the mouse Pitx3 gene is located in the chromosomal region as the mutant aphakia gene, which is associated with a phenotype of small eyes and overall ocular disorganization.

Accordingly, in one aspect, the invention provides Pitx3 nucleic acids. In one embodiment, the Pitx3 nucleic acid comprises a nucleotide sequence set forth in SEQ ID Nos. 1, 2, 4, 5, 6, 8 and/or 29 or complement thereof In further embodiments, the nucleic acid molecule is a Pitx3 nucleic acid having an overall homology of at least about 70%, 80%, 85%, 90%, 95%, 98% or preferably 99% with a nucleotide sequence shown as SEQ ID NOs. 1, 2, 4, 5, 6, 8 and/or 29 or to the complement of the nucleic acid shown as SEQ ID NOS 1, 2, 4, 5, 6, 8 and/or 29. Also within the scope of the invention are nucleic acids comprising a nucleotide sequence which is homologous, i.e., has a certain degree of homology or identity, with a portion of a nucleotide sequence shown as SEQ ID NOS. 1, 2, 4, 5, 6, 8 and/or 29 or to the complement thereof. The portion can be the nucleotide sequence located outside the sequence encoding the homeobox domain and/or the 14 amino acid C-terminal domain or the portion can be a nucleotide region located upstream of the sequence encoding the homeobox domain. In yet another embodiment, the nucleic acid of the invention is capable of hybridizing under appropriate stringency conditions (low or high) to a nucleic acid having SEQ ID NOS. 1, 2, 4, 5, 6, 8 and/or 29 or to the complement of the nucleic acid shown as SEQ ID NOS. 1, 2, 4, 5, 6, 8 and/or 29. Preferred nucleic acids of the invention are vertebrate, preferably mammalian, even more preferably human nucleic acids.

The invention also provides probes and primers comprising substantially purified oligonucleotides, which correspond to a region of nucleotide sequence which hybridizes to at least about 6 at least about 10, and at least about 15, at least about 20, or preferably at least about 25 consecutive nucleotides of the sequence set forth as SEQ ID NOS. 1, 2, 4, 5, 6, 8, 28, and/or 29, or complements of the sequence set forth as SEQ ID NOS. 1, 2, 4, 5, 6, 8, 28, and/or 29, as well as polymorphic variants and/or mutants thereof Much preferred probes and primers are those which essentially do not hybridize to other nucleic acids found naturally in cells, such as other Pitx genes, i.e., Pitx1 and Pitx2. In one embodiment, the probe is capable of hybridizing to the 17 base pair insert found in the Pixt3 genes of individuals having the disorder ASDM and having the nucleotide sequence set forth in SEQ ID NO. 28. In preferred embodiments, the probe/primer further includes a label group attached thereto, which is capable of being detected.

In certain embodiments, the Pitx3 nucleic acid is expressed in vitro and in vivo. For expression, the subject nucleic acids can include a transcriptional regulatory sequence, e.g. at least one of a transcriptional promoter (e.g., for constitutive expression or inducible expression) or transcriptional enhancer sequence, which regulatory sequence is operably linked to the gene sequence. Such regulatory sequences in conjunction with a Pitx3 nucleic acid molecule can provide a useful vector for gene expression. This invention also describes host cells transfected with said expression vector whether prokaryotic or eukaryotic and in vitro (e.g. cell culture) and in vivo (e.g. transgenic) methods for producing Pitx3 polypeptides by employing said expression vectors.

In another aspect, the invention features isolated Pitx3 polypeptides, preferably substantially pure preparations, e.g. of cell purified or recombinantly produced polypeptide. In particularly preferred embodiments, the subject polypeptide has a Pitx3 bioactivity, for example, the subject polypeptide is capable of interacting with a target nucleic acid sequence, or of modulating cell proliferation, differentiation and/or cell survival of cells, such as lens cells.

In a preferred embodiment, the polypeptide is encoded by a nucleic acid which hybridizes with the nucleic acid sequence represented in SEQ ID NOS. 1, 2, 4, 5, 6, 8 and/or 29. In a further preferred embodiment, the Pitx3 polypeptide comprises an amino acid sequence set forth in SEQ ID NOS. 3, 7, 9 and/or 30. The subject Pitx3 polypeptide also includes within its scope modified polypeptides, e.g. polypeptides which are resistant to post-translational modification, for example, due to mutations which alter modification sites (such as tyrosine, threonine, serine or aspargine residues), or which prevent glycosylation of the polypeptide, or which prevent interaction of the polypeptide with intracellular polypeptides involved in signal transduction.

The Pitx3 polypeptides of the present invention can be glycosylated, or conversely, by choice of the expression system or by modification of the polypeptide sequence to preclude glycosylation, reduced carbohydrate analogs can also be provided. Glycosylated forms can be obtained based on derivatization with glycosaminoglycan chains. Also, Pitx3 polypeptides can be generated which lack or comprise a signal sequence (though this is typically cleaved off even if present in the pro-form of the polypeptide).

The Pitx3 polypeptide can comprise a full length polypeptide or can comprises a smaller fragment corresponding to one or more particular motif/domain, such as the homeobox domain and the 14 amino acid C-terminal domain, or a fragment comprising at least about 5, 10, 25, 50, 75, 100, 125, 130, 135, 140 or 145 amino acids in length. In preferred embodiments, the polypeptide has a Pitx3 bioactivity, such as the capability to interact with DNA and/or modulate cell proliferation, differentiation and/or survival.

In yet another preferred embodiment, the invention features a purified or recombinant polypeptide, which has the ability to modulate, e.g., mimic or antagonize, an activity of a wild-type Pitx3 polypeptide. Preferably, the polypeptide comprises an amino acid sequence which is identical or homologous to a sequence designated in SEQ ID No. 3, 7, 9 and/or 30.

Another aspect of the invention features chimeric molecules (e.g., fusion polypeptides) comprising a Pitx3 polypeptide. For instance, the Pitx3 polypeptide can be provided as a recombinant fusion polypeptide which includes a second polypeptide portion, e.g., a second polypeptide having an amino acid sequence unrelated (heterologous) to the Pitx3 polypeptide.

A still further aspect of the present invention features antibodies and antibody preparations specifically reactive with an epitope of a Pitx3 polypeptide. The epitope may be located in a region that is common to a mutated Pitx3 protein and a wild-type Pitx3 protein or the epitope may be specific to a mutated Pitx3 protein, e.g., in the region of the Pitx3 protein that encompasses and/or which is downstream of amino acid 219 (encoded by the codon in which the 17 bp insertion is found in subjects having ASDM). Another preferred antibody is an antibody recognizing specifically amino acid 13 of the Pitx3 variant in which this residue is an Asparagine.

The invention also features transgenic non-human animals which include (and preferably express) a heterologous form of a Pitx3 gene described herein, and/or which mis-express an endogenous Pitx3 gene (e.g., an animal in which expression of the subject Pitx3 polypeptides is disrupted). Such transgenic animals can serve as animal models for studying cellular and/or tissue disorders comprising mutated or mis-expressed Pitx3 alleles or for use in drug screening. Particularly useful transgenic animals are those in which the endogenous Pitx3 gene has been "knock-out" and the animal expresses the mutated form of the Pitx3 protein that is found in subjects having cataracts and/or ASMD. Such mice will allow the identification of therapeutic compounds for preventing and treating cataracts, ASMD, and similar diseases. Alternatively, such transgenic animals can be useful for expressing recombinant Pitx3 polypeptides.

In another aspect, the invention provides methods for preventing or treating a disease, which is caused by, or contributed to by, an aberrant Pitx3 activity, nucleic acid and/or protein. In a preferred embodiment, the disease is a ASMD, a disease or disorder of the lens or other eye structure.

In a further aspect, the invention provides methods for modulating a Pitx3 bioactivity, such as the expression of a gene encoding Pitx3 or a gene located downstream of Pitx3 in a biochemical pathway in which Pitx3 is involved. In another aspect of the invention, a bioactivity of Pitx3 is modulated by administering to the subject a compound which modulates the interaction of Pitx3 with another molecule, e.g., a nucleic acid. Pharmaceutical compositions that modulate expression of a gene, e.g., Pitx3 gene, or a Pitx3 activity can be a protein, a peptide, a peptidomimetic, or other small molecule or nucleic acid (e.g., gene replacement therapies, antisense, ribozyme and triplex nucleic acid constructs).

In a preferred embodiment, the pharmaceutical composition is comprised of an agonist of a normal (functional) Pitx3 bioactivity. For example, to ameliorate disease symptoms involving insufficient Pitx3 protein level or a Pitx3 protein having a less potent activity than the wild-type Pitx3, an agonist therapeutic can be administered to the subject. The agonist can be, e.g., a compound which is capable of modulating Pitx3 gene expression or expression of a gene located downstream of Pitx3 in a biochemical pathway in which Pitx3 is involved. The agonist can also be a compound that is capable of modulating an interaction between Pitx3 and another molecule, e.g., a nucleic acid.

In another preferred embodiment, the pharmaceutical composition is comprised of an antagonist of a Pitx3 bioactivity. For example, to ameliorate disease symptoms involving excessive Pitx3 protein levels or a Pitx3 protein having a more potent activity than the wild-type Pitx3, an antagonist gene therapeutic or antagonist polypeptide therapeutic can be administered to the subject. The antagonist can be, e.g., a compound that is capable of modulating Pitx3 gene expression or expression of a gene located downstream of Pitx3 in a biochemical pathway in which Pitx3 is involved. The antagonist can also be a compound that is capable of modulating an interaction between Pitx3 and another molecule, e.g., a nucleic acid.

The invention provides methods and kits for determining whether a subject has or is at risk of developing a disease associated with an aberrant Pitx3 activity, nucleic acid and/or protein, e.g., an ocular disease, in particular cataracts and ASMD. In one embodiment, the diagnostic method consists of determining a Pitx3 activity, such as the Pitx3 polypeptide or mRNA level in cells from a subject. A higher or lower level of a Pitx3 activity, e.g., Pitx3 polypeptide or mRNA level, relative to the Pitx3 activity in similar cells from a healthy subject which is not at risk of developing the disease, may indicate that the subject is at risk of developing a disease which is caused by or contributed to an aberrant Pitx3 level.

In another embodiment, the diagnostic methods and kits for determining whether a subject has or is at risk of developing a disease associated with an aberrant Pitx3, include detecting, in a biological sample obtained from the subject, the presence or absence of a genetic lesion, characterized by at least one of: (i) a mutation in a Pitx3 gene; (ii) the mis-expression of a Pitx3 gene; or (iii) an error or mutation in the promoter regulating a Pitx3 gene that may lead to aberrant expression. In preferred embodiments, detecting the genetic lesion includes ascertaining the existence of at least one of: (a) a deletion of one or more nucleotides from a wildtype gene; (b) an addition of one or more nucleotides to a wildtype gene; (c) a substitution of one or more nucleotides of a wildtype gene; (d) a gross chromosomal rearrangement of a wildtype gene; (e) an alteration in the level of a messenger RNA transcript of a gene; (f) the presence of a non-wild type splicing pattern of a messenger RNA transcript of a gene; and/or (h) an aberrant level of a polypeptide. A particularly preferred diagnostic method consists of determining the presence in a Pitx3 gene or mRNA of a subject, the presence of a 17 bp insertion in codon 219 of Pitx3, found in individuals having cataracts and ASMD and can therefore by used as a test to determine whether a subject has or is susceptible to develop cataracts and/or ASMD. Another preferred diagnostic method for determining whether a subject has or is susceptible of developing cataracts consists in determining the amino acid at residue 13 of Pitx3. The presence of an amino acid other than a Serine, e.g., an Asparagine, is indicative that the subject has or is likely to develop cataracts.

Detecting the genetic lesion or determining the identity of an allelic variant can include: (i) providing probes or primers comprised of an oligonucleotide which hybridizes to a sense or antisense sequence of a Pitx3 gene or gene fragment (wildtype or mutant); (ii) contacting the probes or primers with an appropriate nucleic acid containing biological sample obtained from the subject; and (iii) detecting, by hybridization of the probes or primers to the nucleic acid, the presence or absence of the genetic lesion.

In a preferred embodiment, the diagnostic methods and/or kits utilize a set of primers for amplifying (e.g. via PCR or LCR) at least one region of a Pitx3 gene and means for analyzing the amplification product for differences (e.g. mutations) from the normal, wildtype coding sequence.

In another preferred embodiment, the diagnostic methods and/or kits utilize a probe to determine its ability to hybridize under appropriately stringent conditions to a complementary nucleic acid sequence in the biological sample, wherein an inability of a probe, which is comprised of a wild-type Pitx3 sequence to hybridize to the sample nucleic acid is indicative of the presence of a mutation in the sample nucleic acid; or the ability of a probe, which is comprised of a mutant Pitx3 sequence to hybridize to the sample nucleic acid comprising a Pitx3 sequence or portion thereof is indicative of the presence of a mutation in the sample nucleic acid.

In yet a further preferred embodiment, the diagnostic methods and kits employ at least one antibody to at least one epitope, which is characteristic of a wildtype or mutant Pitx3 polypeptide in an immunoassay procedure to detect the presence of a Pitx3 mutation in a biological sample obtained from a subject.

In yet another aspect, the invention provides assays, for screening test compounds to identify compounds that modulate a Pitx3 activity such as by modulating the expression of a Pitx3 gene. Such screening techniques can be performed in vitro or in vivo, in a cell or in an animal. In one embodiment, the assay comprises combining a Pitx3 polypeptide, a Pitx3 binding partner, e.g., a target nucleic acid, and a test compound under conditions wherein, but for the test compound, the Pitx3 polypeptide and Pitx3 binding partner are able to interact, and detecting the formation of a Pitx3/Pitx3 binding partner complex. A difference in formation, e.g., amount, of a Pitx3 polypeptide/Pitx3 binding partner complex in the presence of a test compound relative to in the absence of the test compound indicates that the test compound modulates a Pitx3 activity. Another assay for identifying a compound which modulates a Pitx3 activity or the expression of a Pitx3 gene, comprises contacting a cell expressing a Pitx3 polypeptide with a test compound and monitoring a Pitx3 activity, such as expression of a gene which is regulated by Pitx3 or a Pitx3 binding partner.

Other features and advantages of the invention will be apparent from the following detailed description and claims.

BRIEF DESCRIPTION OF THE FIGURES

FIG. 1 shows the nucleotide sequence (SEQ ID NO. 1) and deduced amino-acid sequence (SEQ ID NO. 3) of the mouse Pitx3 gene. The first methionine codon (ATG) followed by a G at position +4 from the ATG is underlined. The homeodomain is shown in boldface. The 14-amino-acid domain is underlined.

FIG. 2 shows an alignment of the amino acid sequence of the mouse Pitx3 protein (SEQ ID NO. 3) with the amino acid sequences of Rieg1/Pitx2 (SEQ ID NO. 26) and Pitx1/POTX (SEQ ID NO. 27). Conserved amino acids are shown in grey. The homeodomain and the 14-amino-acid motif are boxed.

FIG. 3 shows the nucleotide sequence (SEQ ID NO. 4) and deduced amino acid sequence (SEQ ID NO. 7) of the human Pitx3 gene. The homeodomain is shown in boldface. The 14-amino-acid motif is underlined.

FIG. 4 shows the nucleotide sequence of a portion of a mutant Pitx3 gene, having an insertion of 17 nucleotides (SEQ ID NO. 28) and the encoded portion of the protein.

FIG. 5 shows the nucleotide and amino acid sequences of the mutant Pitx3 gene, having a 17 bp insertion in codon 219 and encoded protein. The 17 bp insertion is represented in bold and the C-terminal amino acid sequence which is different from the wild-type Pitx3 protein is underlined.

FIG. 6 shows the nucleotide and amino acid sequences of a gene encoding a second Pitx3 variant in which amino acid residue 13 is different from that in the wild-type Pitx3 protein (amino acid 13 is represented in bold).

DETAILED DESCRIPTION OF THE INVENTION

General

Figure 7:
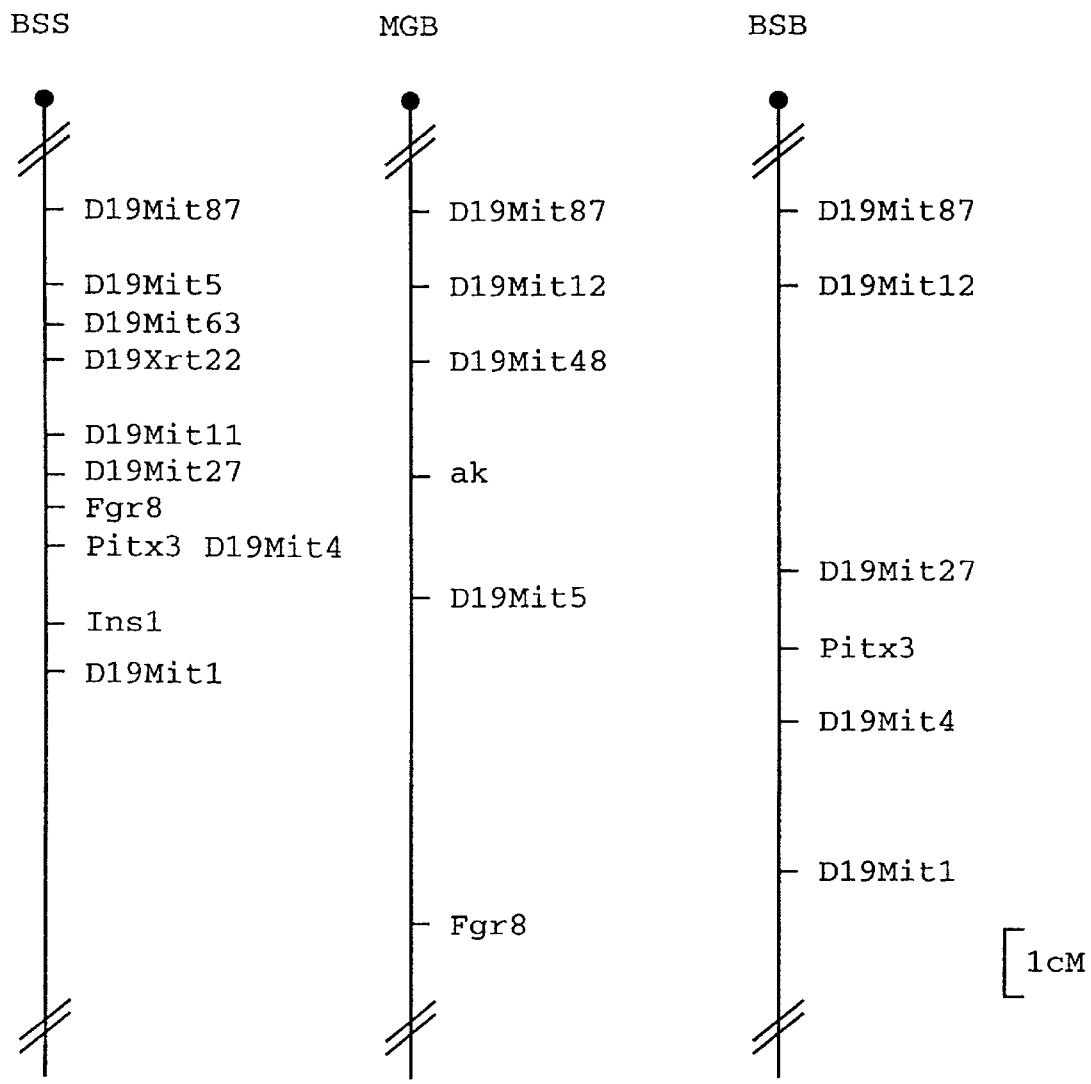
FIG. 7 shows the localization of mouse Pitx3 to distal portion of mouse chromosome 19. BSB and BSS panels mapping data are presented in this paper. The corresponding portion of the MGB map was obtained from Mouse Genome Informatics (http://www.informatics.jax.org/map.html). Note positions of markers D19Mit87, D19Mit12. Fgf8 integrated into the MGB map and also localized on BSB or BSS or both maps. The positions of the Pitx3 gene and of the ak mutation are shown in boldface.

The invention is based at least in part on the discovery of two genes, a human and a mouse gene, termed hPitx3 and mPitx3 genes, respectively, which are involved in the development of the lens and in diseases affecting the lens, e.g, cataracts. As shown herein, variants or mutant forms of this gene were found in individuals having cataracts, but not in normal individuals. In particular, a mutant Pitx3 protein was found in each affected member of a family carrying the autosomal dominant disorder Anterior Segment Mesenchymal Dysgenesis (ASMD), which is characterized by the development of cataracts in each affected member and an abnormal development of anterior eye structures. A variant Pitx3 protein gene was also found in a congenital form of cataract. Furthermore, as shown herein, Pitx3 is localized in the same mouse chromosomal region as the aphakia (ak) mutation, which is associated with reduced eye size and overall ocular disorganization (Varnum, D. S. and Stevens, L. C. (1968) *J. Hered.* 59:147–150). Thus, Pitx3 plays an important role in the development of the lens and in diseases affecting the lens. As discussed further herein, Pitx3 is also likely to be associated with other ocular diseases.

As further described in the Examples, the invention features human and mouse Pitx3 nucleic acids. The nucleotide sequences of the mouse and human Pitx3 genes are shown in FIGS. 1 and 3, respectively, and set forth in SEQ ID NOS. 1 and 4, respectively. The putative proteins encoded by the mouse and human Pitx3 genes is a 302 amino acid protein having the amino acid sequences shown in FIG. 1 and FIG. 3, respectively, and set forth in SEQ ID NO. 3 and SEQ ID NO. 7, respectively.

The coding region of human and mouse Pitx3 genes are about 90% identical and the human and mouse Pitx3 proteins are about 99% identical. The 5' and 3' untranslated regions of the two genes are more different. In fact, the 3' untranslated regions of the mouse and human genes is only about 85% identical.

Analysis of Pitx3 nucleotide and amino acid sequences revealed that Pitx3 is a homeobox domain (HD) containing protein. The amino acid sequence of the homeobox of mouse and human Pitx3 proteins is identical and corresponds to amino acid 62 to amino acid 121 of SEQ ID NOS. 3 and 7 and is encoded by nucleotides 317–496 of SEQ ID NO. 1 and by nucleotides 187–364 of SEQ ID NO. 4. The HD is a DNA-binding motif which is characteristic and strongly conserved among the HD proteins. The specificity of HD binding to its target is based on distinct DNA-binding properties of the HD sequence and also, at least in some cases, on the assembly with other proteins. Protein-protein interactions can involve both specific residues within the HD itself and other regions of the protein, as has been suggested for the regions immediately C- and N-terminal to the HD (Sharkey, M., et al. (1997) *Trends Genet.* 13(4):145–151). The DNA binding sequence of Pitx3 is likely to be a bicoid target site, as described in Lamonerie et al. (1996) Genes & Development 10: 1284.

A BLASTN sequence analysis revealed that Pitx3 has significant homology in the homeobox region and in the 14 amino acid C-terminal domain to other homeobox containing proteins, in particular to the two other Pitx proteins, i.e., Pitx1/Potx (Lamoneri et al., supra and Szeto et al. (1996) Proc. Natl. Acad. Sci. USA 93:7706) and Pitx2/Rieg (Semina et al. (1996) Nature Genetics 14:392. The 14 amino acid C-terminal domain is underlined in the sequences shown in FIGS. 1 and 3. It corresponds to amino acids 262–275 of SEQ ID Nos. 3 and 7 and is encoded by nucleotides 917–958 of SEQ ID NO. 1 and nucleotides 777–818 of SEQ ID NO. 4. A comparison of the amino acid sequences of mouse Pitx3 and that of Pitx1/Potx and Rieg/Pitx2 is shown in FIG. 2. The amino acid sequences of the homeobox domains of mouse Pitx3 and Pitx2/Rieg1 are in fact identical. The amino acid sequences of the homeobox domains of mouse Pitx3 and Pitx1/Potx differ in two amino acids. There is also significant homology extending into the N-terminal and C-terminal regions from the HD. Another domain of Pitx3, i.e., the 14 amino acid C-terminal box is also strongly conserved between these three genes. In fact, as shown in FIG. 2, the amino acid sequences of this box are identical in the mouse Pitx3 protein and in the Pitx2/Rieg protein. The amino acid sequences of this box in mouse Pitx3 differs in only 2 amino acids from that in Pitx1/Potx. The strong homology between these three proteins in these domains suggest that they may be members of a family of proteins, the Pitx/Rieg homeobox-containing transcription factor gene family. However, outside of these domains, the amino acid sequence homology between Pitx3 and the other Pitx proteins is weaker. In fact, the overall identity of the amino acid sequence of Pitx3 proteins with that of other Pitx proteins is only about 40%.

The Pitx proteins are found to be most closely related to the *C. elegans* Unc-30 protein, Drosophila orthodenticle (Otd) and its murine homologs Otx1 and Otx2, and the paired-like proteins Drg 11, al, Cart-1, Prx-1, Prx-2 and Chx-10 (for comparisons, see Lamonerie [Lamonerie, T., et al. (1996) supra] and Semina [Semina, E. V. (1996) supra]). The paired-like proteins were found to share a 14-amino-acid motif, located 3' of the HD, with the Pitx proteins (5; recently designated OAR [Furukawa, T., et al, (1 997) *PNAS USA* 94(7):3088–3093]), which may represent a DNA-binding element or a site of protein-protein interaction playing a role in the specificity of the HD protein's function.

As further shown herein, human and mouse Pitx3 genes comprise 3 exons and 2 introns. The position of the introns in the mouse and human Pitx3 genes is shown in Table I and in FIG. 3, respectively. As also found in the other Pitx genes, one of the introns is located in the region encoding the homeobox domain.

As described in the Examples, Pitx3 is expressed predominantly in the lens during embryogenesis. Thus, the tissue distribution of Pitx3 expression is markedly different from that of the other Pitx genes. Rieg1/Pitx2 and Pitx1/Potx have very similar temporal and spatial expression (Szeto et al, supra; Semina et al., supra), overlapping in the maxilla, mandible, Rathke's pouch, eye, umbilicus, midgut region, and the limbs (Semina et al., supra and Szeto et al., supra) and beginning early in development; 8-days pc embryos exhibit strong signal in the head and trunk (Semina et al., supra). Pitx3 mRNA, on the other hand, was first detected in 11-dpc embryos in a survey of embryos from 8.5–11.5 dpc, and the signal was restricted to the developing lens. Thus, although Pitx3 has significant sequence similarity to other Pitx genes, it is likely to be involved in different biological functions. In particular, Pitx3 is likely to be involved in the development of structures of the eye.

As shown herein, Pitx3 is associated with diseases affecting the lens, e.g., cataract. In fact, there was cosegregation of a mutation in Pitx3 in families having a disorder termed Anterior Segment Mesenchymal Dysgenesis, a disorder characterized by the development of cataracts in all affected individuals and an abnormal development of anterior eye structures (see, e.g., Hittner et al. (1982) *Am. J. Ophthalmol.* 93:57). Thus, each one of the 16 individuals having cataracts in this family had a Pitx3 gene containing a 17 base pair insertion in codon 219. This insertion results in a frameshift and in the expression of a mutated Pitx3 protein having a different amino acid composition at the C-terminal of the protein (see FIGS. 4 and 5). The nucleic acid sequence of this mutant Pitx3 cDNA and of the encoded protein are set forth as SEQ ID NOS. 8 and 9, respectively. It is likely that this mutation affects the activity of Pitx3. In particular, it is likely that its interaction with one or more other proteins or with a target nucleic acid sequence is different from that of the wild-type protein.

Furthermore, another variant of Pitx3 was found in an individual having congenital cataract, but not in normal controls. The Pitx3 gene of this individual has a one nucleotide substitution: the G in codon 13 of the open reading frame is a C in the subject having congenital cataract. Thus, the Pitx3 protein in the affected individual has an Asparagine at position 13, as opposed to a Serine in the wild-type protein. Thus, variant forms of Pitx3 have been associated with various forms of cataracts.

Accordingly, the invention provides nucleic acids encoding Pitx3 nucleic acids, proteins, and homologs thereof The invention also provides diagnostic methods for determining whether a subject has or is at risk of developing a disease associated with an aberrant Pitx3, e.g., a disorder of the eye, such as cataracts and ASMD. Also within the scope of the invention are methods for treating such disorders and assays for isolating compounds for treating such diseases.

For convenience, the meaning of certain terms and phrases employed in the specification, examples, and appended claims are provided below.

DEFINITIONS

The term "agonist", as used herein, is meant to refer to an agent that upregulates (e.g. potentiates or supplements) a Pitx3 bioactivity. A Pitx3 agonist can be a Pitx3 protein or nucleic acid encoding a Pitx3 protein or a protein having at least one Pitx3 activity. A Pitx3 agonist can be a compound that upregulates expression of a Pitx3 gene. An agonist can also be a compound which increases the interaction of a Pitx3 polypeptide with another molecule, e.g., a nucleic acid. Alternatively, a Pitx3 agonist can be a compound which mimics the effect of binding of a Pitx3 polypeptide to its target nucleic acid sequence and can be, e.g., a protein, that binds to the same target sequence as a Pitx3 polypeptide. A Pitx3 agonist can also be a compound which modulates the expression or bioactivity of a protein which is located downstream or upstream of Pitx3 or which interacts with Pitx3.

"Antagonist" as used herein is meant to refer to an agent that downregulates (e.g. suppresses or inhibits) a Pitx3 bioactivity. A Pitx3 antagonist can be a dominant negative Pitx3 protein or nucleic acid encoding such. An antagonist can be a compound that downregulates expression of a Pitx3 gene. A preferred Pitx3 antagonist inhibits the interaction between a Pitx3 polypeptide and another molecule, e.g., a nucleic acid, in particular a target DNA sequence. A Pitx3 antagonist can also be a compound which modulates the expression or activity of a protein which is located downstream or upstream of Pitx3 or which interacts with Pitx3.

The term "allele", which is used interchangeably herein with "allelic variant" refers to alternative forms of a gene or portions thereof Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

The term "allelic variant of a polymorphic region of a Pitx3 gene" refers to a region of a Pitx3 gene having one of several nucleotide sequences found in that region of the gene in other individuals.

"Biological activity" or "bioactivity" or "activity" or "biological function", which are used interchangeably, for the purposes herein means an effector function that is directly or indirectly performed by a Pitx3 polypeptide (whether in its native or denatured conformation), or by any subsequence thereof. Biological activities include binding to a molecule, e.g., a nucleic acid, such as a specific DNA or RNA target sequence; binding to another protein, e.g., a protein with which a Pitx3 polypeptide interacts, such as by dimerization; regulation of expression of target genes, e.g., modulation of transcription from a promoter comprising a binding site directly or indirectly targeted by Pitx3 or a Pitx3-binding protein; modulation of cellular proliferation and/or differentiation; modulation of cell death; and/or immune modulation, whether presently known or inherent. A Pitx3 bioactivity can be modulated by affecting directly a Pitx3 polypeptide. Alternatively, a Pitx3 bioactivity can be modulated by modulating the level of a Pitx3 polypeptide, such as by modulating expression of a Pitx3 gene. Biologically active Pitx3 includes antagonist and agonist polypeptides.

As used herein the term "bioactive fragment of a Pitx3 polypeptide" refers to a fragment of a full-length Pitx3 polypeptide, wherein the fragment specifically mimics or antagonizes the activity of a wild-type Pitx3 polypeptide. The bioactive fragment preferably is a fragment capable of binding to a second protein, or a nucleic acid.

The term "an aberrant activity", as applied to an activity of a polypeptide such as Pitx3, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target molecule, e.g., nucleic acid sequence or protein relative to its native counterpart. A cell can have an aberrant Pitx3 activity due to overexpression or underexpression of the gene encoding Pitx3.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Cell proliferative diseases" refers to diseases or disorders characterized by an abnormal cell proliferation, differentiation or survival, in particular of lens cells. Thus, a cell proliferative disease can be a disease or disorder characterized by hyper- or hypo-proliferation of at least one cell type, epithelial cells, lens epithelial cells. Examples of cell proliferative diseases include benign or malignant tumor growth, e.g., any form of cancer or autoimmune diseases.

A "chimeric polypeptide" or "fusion polypeptide" is a fusion of a first amino acid sequence encoding one of the subject Pitx3 polypeptides with a second amino acid sequence defining a domain (e.g. polypeptide portion) foreign to and not substantially homologous with any domain of a Pitx3 polypeptide. A chimeric polypeptide may present a foreign domain which is found (albeit in a different polypeptide) in an organism which also expresses the first polypeptide, or it may be an "interspecies", "intergenic", etc. fusion of polypeptide structures expressed by different kinds of organisms. In general, a fusion polypeptide can be represented by the general formula X-Pitx3-Y, wherein Pitx3 represents a portion of the polypeptide which is derived from a Pitx3 polypeptide, and X and Y are independently absent or represent amino acid sequences which are not related to a Pitx3 sequence in an organism, including naturally occurring mutants.

The term "nucleotide sequence complementary to the nucleotide sequence set forth in SEQ ID NO. x" refers to the nucleotide sequence of the complementary strand of a nucleic acid strand having SEQ ID NO. x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO. x refers to the complementary strand of the strand having SEQ ID NO. x or to any nucleic acid having the nucleotide sequence of the complementary strand of SEQ ID NO. x. When referring to a single stranded nucleic acid having the nucleotide sequence SEQ ID NO. x, the complement of this nucleic acid is a nucleic acid having a nucleotide sequence which is complementary to that of SEQ ID NO. x. The nucleotide sequences and complementary sequences thereof are always given in the 5' to 3' direction. The term "complement" and "reverse complement" are used interchangeably herein.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g,. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes or a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a Pitx3 polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a polypeptide with the same biological activity.

A disease, disorder or condition "associated with" or "characterized by" an aberrant Pitx3 refers to a disease, disorder or condition in a subject which is caused by or contributed to by an aberrant Pitx3 activity or which is associated with an aberrant Pitx3 amino acid an/or nucleotide sequence, such as the 17 bp insertion in codon 219 of Pitx3 or an Arginine at position 13.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, though preferably less than 25% identity, with one of the Pitx3 sequences of the present invention.

The term "interact" as used herein is meant to include detectable interactions (e.g. biochemical interactions) between molecules, such as interaction between a polypeptide and a nucleic acid or between two polypeptides as can be detected using, for example, a DNA binding assay or a yeast two hybrid assay, respectively. The term interact is also meant to include "binding" interactions between molecules. Interactions may, for example, be protein-protein, protein-nucleic acid, nucleic acid-nucleic acid, and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject Pitx3 polypeptides preferably includes no more than 10 kilobases (kb) of nucleic acid sequence which naturally immediately flanks the Pitx3 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "lens cells" refers to cells present in a crystalline lens. A lens cell can be an epithelial cell, e.g., an epithelial cell from the central epithelium or from the equatorial epithelium. A lens cell can also be a fiber cell. A lens consists of concentric layers: the external layers are soft and easily detachable and form the external layers of the lens, whereas more internal layers are harder and form the "nucleus of the lens". A lens cell can be located in the external layers of a lens or in the nucleus of the lens.

The term "modulation" as used herein refers to both upregulation (i.e., activation or stimulation (e.g., by agonizing or potentiating)) and downregulation (i.e. inhibition or suppression (e.g., by antagonizing, decreasing or inhibiting)).

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous subject (for that gene), the mutation is said to be co-dominant.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant Pitx3 gene is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "Pitx3 nucleic acid" is intended to encompass nucleic acids comprising the nucleotide sequence SEQ ID No. 1, 2, 4, 5, 6, 8, or 29, fragments thereof, and homologs thereof, so long as they have some characteristic of Pitx3.

The term "Pitx3 therapeutic" refers to various forms of Pitx3 polypeptides, as well as peptidomimetics, nucleic acids, or small molecules, which can modulate at least one activity of a Pitx3 polypeptide, e.g., binding to a nucleic acid, by mimicking or potentiating (agonizing) or inhibiting (antagonizing) the effects of a naturally-occurring Pitx3 polypeptide. A Pitx3 therapeutic which mimics or potentiates the activity of a wild-type Pitx3 polypeptide is a "Pitx3 agonist". Conversely, a Pitx3 therapeutic which inhibits the activity of a wild-type Pitx3 polypeptide is a "Pitx3 antagonist".

The terms "Pitx3 polypeptide" and "Pitx3 protein" are intended to encompass polypeptides comprising the amino acid sequence SEQ ID No. 3, 7 or 30, fragments thereof, and homologs thereof, so long as they have some characteristic of Pitx3, and include agonist and antagonist polypeptides.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding a Pitx3 polypeptide is inserted into a suitable expression vector which is in turn used to transform a host cell to produce the heterologous protein. Moreover, the phrase "derived from", with respect to a recombinant Pitx3 gene, is meant to include within the meaning of "recombinant protein" those proteins having an amino acid sequence of a native Pitx3 polypeptide, or an amino acid sequence similar thereto which is generated by mutations including substitutions and deletions (including truncation) of a naturally occurring form of the polypeptide.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that modulate a Pitx3 bioactivity.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a vertebrate, preferably a Pitx3 gene.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a Pitx3 gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of Pitx3 polypeptide.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a Pitx3 polypeptide or, in the case of anti-sense expression from the transferred gene, the expression of a naturally-occurring form of the Pitx3 polypeptide is disrupted.

As used herein, the term "transgene" means a nucleic acid sequence (encoding, e.g., a Pitx3 polypeptides) or an antisense transcript thereto which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extra-chromosomally replicating DNA. In the typical transgenic animals described herein, the transgene causes cells to express a recombinant form of one of the Pitx3 polypeptide, e.g. either agonistic or antagonistic forms. However, transgenic animals in which the recombinant Pitx3 gene is silent are also contemplated, as for example, the FLP or CRE recombinase dependent constructs described below. Moreover, "transgenic animal" also includes those recombinant animals in which gene disruption of a Pitx3 gene is caused by human intervention, including both recombination and antisense techniques.

The term "treating" as used herein is intended to encompass curing as well as ameliorating at least one symptom of the condition or disease.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

A "wound to eye tissue" refers to severe dry eye syndrome, corneal ulcers and abrasions, ophthalmic surgical wounds and the like.

Pitx3 Nucleic Acids and Gene Therapeutics

The invention provides isolated Pitx3 nucleic acids, homologs thereof and fragments thereof A preferred Pitx3 nucleic acid is a vertebrate Pitx3 nucleic acid, and even more preferably a mammalian Pitx3 nucleic acid, such as a human Pitx3 nucleic acid.

In one embodiment, the invention provides isolated nucleic acids comprising nucleotide sequences encoding Pitx3 polypeptides, equivalents thereof, homologs thereof, and fragments thereof The term equivalent is understood to include nucleotide sequences encoding functionally equivalent Pitx3 polypeptides or functionally equivalent peptides having an activity of a Pitx3 polypeptide such as described herein. Equivalent nucleotide sequences will include sequences that differ by one or more nucleotide substitution, addition or deletion, such as allelic variants; and will, therefore, include sequences that differ from the nucleotide sequence of the Pitx3 nucleic acids shown in SEQ ID NOS 1, 2, 4, 5, 6, 8 and/or 29 or complement thereof due to the degeneracy of the genetic code.

Preferred nucleic acids of the invention comprise a nucleic acid sequence which is at least about 70%, at least about 75%, at least about 80%, at least about 85%, at least about 90%, at least about 95%, or at least about 98% homologous to a nucleic acid sequence of SEQ ID NOS. 1, 2, 4, 5, 6, 8 and/or 29 or complement thereof. Even more preferred nucleic acids have a nucleotide sequence which is at least about 99% identical to the nucleotide sequence set forth in SEQ ID NOS. 1, 2, 4, 5, 6, 8 and/or 29 or complement thereof Preferred nucleic acids have an overall nucleotide sequence homology of at least about 70%, 75%, 80%, 90%, preferably at least about 92%, at least about 95%, at least about 98%, and even more preferably at least about 99% identity with the sequence set forth in SEQ ID No. 1, 2, 4, 5, 6, and/or 8 or complement thereof Other preferred nucleic acids of the invention comprise a nucleotide sequence that is at least about 70%, 75%, 80%, 85%, 90%, 95%, 97%, 98%, or preferably at least 99% identical to a specific portion of a nucleic acid comprising the nucleotide sequence set forth in any of SEQ ID NOS. 1, 2, 4, 5, 6, 8 and/or 29 or complement thereof. For example, preferred nucleic acids of the invention comprise a nucleotide sequence which is homologous to the nucleotide sequence of a DNA binding domain, or portion thereof, of a gene comprising the nucleotide sequence set forth in SEQ ID NOS. 1, 2, 4, 5, 6, 8 and/or 29 or complement thereof Particularly preferred nucleic acids comprise a nucleotide sequence encoding a homeobox domain and/or a 14 amino acid C-terminal domain, such as that corresponding to amino acids 262–275 of human or mouse Pitx3.

Yet other preferred nucleic acids are homologous to regions of human and/or mouse Pitx3 DNA sequences located outside the region encoding the homeobox domain and/or outside the region encoding the 14 amino acid C-terminal box. The invention also provides nucleic acids having a certain degree of homology to a 5' or 3' UTR of the mouse or the human Pitx3, such as those in SEQ ID NOS. 1 or 4. The term "having a certain degree of homology" refers to any one of about 60%, 70%, 75%, 80%, 85%, 90%, 95%, 98%, or 99% homology or identity.

Also within the scope of the invention are nucleic acids comprising essentially the entire coding region of a Pitx3 nucleic acid or homolog thereof such as a nucleic acid comprising SEQ ID NO. 2 or SEQ ID NO. 6.

Nucleic acids having a sequence that differs from the nucleotide sequence shown in one of SEQ ID NOS. 1, 2, 4, 5, 6, 8 and/or 29 or complement thereof due to degeneracy in the genetic code are also within the scope of the invention. Such nucleic acids encode functionally equivalent peptides (i.e., a peptide having a biological activity of a Pitx3 polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a Pitx3 polypeptide. However, it is expected that DNA sequence polymorphisms that do lead to changes in the amino acid sequences of the subject Pitx3 polypeptides will exist among mammals. One skilled in the art will appreciate that these variations in one or more nucleotides (e.g., up to about 3–5% of the nucleotides) of the nucleic acids encoding polypeptides having an activity of a Pitx3 polypeptide may exist among individuals of a given species due to natural allelic variation.

Nucleic acids which are homologous to Pitx3 nucleic acids set forth in SEQ ID NOS. 1, 2, 4, 5, 6, 8 and/or 29 can be isolated, e.g., by hybridization or PCR experiments, as described below. For example, homologs can be identified by using a Pitx3 full length cDNA or portion thereof as a probe to screen genomic or cDNA libraries by hybridization. Alternatively, degenerate PCR primers capable of hybridizing under appropriate stringency to a Pitx3 nucleic acid can be used to PCR amplify at least a region of a Pitx3 homolog. The primers can be designed to amplify a region that is conserved among numerous Pitx3 genes, or they can be designed to hybridize to a region of Pitx3 which is very different from that in other Pitx genes, such as the 5' end of the coding region.

The invention also provides nucleic acids which are capable of hybridizing under appropriate hybridization conditions to a nucleic acid having SEQ ID NOS. 1, 2, 4, 5, 6, 8 and/or 29 or complement thereof. Appropriate stringency conditions for identifying homologs, for example, 6.0 x sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

Nucleic acids can be obtained from mRNA present in any of a number of eukaryotic cells. It is also possible to obtain nucleic acids of the present invention from genomic DNA from both adults and embryos. For example, a gene can be cloned from either a cDNA or a genomic library in accordance with protocols described herein, as well as those generally known to persons skilled in the art. Examples of tissues and/or libraries suitable for isolation of the subject nucleic acids include embryonic lens cells. A cDNA can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a protein can also be cloned using established polymerase chain reaction techniques in accordance with the nucleotide sequence information provided by the invention. The nucleic acid of the invention can be DNA or RNA.

Preferred nucleic acids which are homologs of the nucleic acids set forth in SEQ ID Nos. 1, 2, 4, 5, 6, 8 and/or 29 or complement thereof are at least about 10, 15, 20, 25, 30, 50, 100, 150, 200, 300, 400, or 500 nucleotides or base pairs long. However, nucleic acids of the invention can have any number of nucleotides or base pairs, so long as they comprise a novel nucleotide sequence. Preferred nucleic acid molecules for use as probes/primer or antisense molecules (i.e. noncoding nucleic acid molecules) can comprise at least about 6, 12, 20, 30, 50, 60, 70, 80, 90 or 100 base pairs in length, whereas coding nucleic acid molecules can comprise about 50, 60, 70, 80, 90, or 100 base pairs.

Also within the scope of the invention are primers and probes. Primers and probes can be used for diagnostic or therapeutic purposes and can be used, e.g, for sequencing Pitx3 nucleic acids, for PCR amplification of Pitx3 sequences or for hybridization purposes. Primers and probes are optionally labeled. Such nucleic acids can also be modified as described below for antisense oligonucleotides.

Probes and primers can be used to determine the presence of a Pitx3 nucleic acid in a sample. Preferred probes and primers are those that can be used to determine the presence of a variant of a Pitx3 nucleic acid, such as a mutant or a polymorphic variant. In particular, the invention provides primers and probes for detecting the presence of a Pitx3 nucleic acid having a 17 base pair (bp) insert in codon 219 in the open reading frame of a Pitx3 gene, an insertion which is associated with the increase likelihood of developing cataracts and with the disorder ASMD. Thus, the invention provides nucleic acid probes comprising a nucleotide sequence which comprise a least a portion of the 17 bp insertion shown in FIG. 4 and set forth in SEQ ID NO. 28, so long as they are capable of specifically hybridizing to a Pitx3 nucleic acid having the insertion, but essentially not to a Pitx3 nucleic acid which does not comprise the insertion. Even more preferably, the probe does essentially not hybridize to other nucleic acids in a cell in appropriate stringency conditions. Preferred probes comprise the 17 base pair sequence set forth in SEQ ID NO. 28. Thus, a probe can comprise the nucleotide sequence set forth in SEQ ID NO. 28 or complement thereof and a certain number of nucleotides from SEQ ID NO. 4 on one or both sides. A probe does not have to have the exact nucleotide sequence or complement sequence of the insertion, so long as it is capable of hybridizing specifically to a Pitx3 nucleic acid having the 17 bp insertion.

Another preferred probe is a probe which is capable of hybridizing specifically to a region of human Pitx3 comprising a C at position 41 of SEQ ID NO. 4, but which does not hybridize to the same region wherein the nucleotide at this position is a G. Such a probe can be used to detect individuals having susceptible of developing cataracts.

Preferred primers for PCR detection of the 17 bp insertion are primers which are capable of hybridizing specifically to sequences flanking the site of insertion and which preferably are not capable of hybridizing to other Pitx genes. Thus, the presence of the 17 bp insertion in a Pitx3 nucleic acid will be indicated by a difference in the size of the amplification product. A primer can also be complementary to an intronic sequence or sequence located in a 5' or 3' untranslated region. Alternatively, one of the primers can be a primer which at least partially overlaps the insertion. The identity of preferred primers for use can be determined using computer programs predicting the specificity of primers and test PCR amplifications. Such methods are known in the art and do not require undue experimentation.

Other preferred primers include those that can be used to amplify a region encompassing nucleotide 41 in SEQ ID NO. 4, or which overlap this nucleotide. Such primers can be used to detect individuals having a likelihood of developing cataracts.

In another embodiment, the invention provides nucleic acids which encode polypeptides that are at least 70%, 80%, 90%, or 95% similar or identical to an amino acid sequence of a vertebrate Pitx3 polypeptide, e.g., an amino acid sequence set forth in SEQ ID NOS. 3, 7, 9 or 30. In an even more preferred embodiment, the nucleic acid of the invention encodes a Pitx3 polypeptide which is at least about 98% similar or identical to a sequence in SEQ ID NO. 3, 7, 9 or 30 and even more preferably at least about 99% similar or identical to an amino acid sequence in SEQ ID NO. 3, 7, 9 or 30. Most preferred nucleic acids encode a Pitx3 polypeptide having an overall amino acid sequence homology or identity of at least about 90%, preferably at least about 92%, at least about 95%, at least about 98%, and even more preferably at least about 99% with the amino acid sequence set forth in SEQ ID NOS. 3, 7, 9 or 30. Yet other preferred nucleic acids include those encoding a polypeptide which has a certain degree of similarity or identity with a portion of a Pitx3 polypeptide, such as the homeobox domain and/or the 14 amino acid C-terminal domain. Alternatively, also within the scope of the invention are nucleic acids encoding a polypeptide which has a certain degree of homology with a region of a Pitx3 polypeptide located outside specific regions, such as the homeobox domain and/or the 14 amino acid C-terminal domain. The term "having a certain degree of homology or similarity" refers to any one of about 60%, 70%, 75%, 80%, 85%, 90%, 95%, 98%, or 99% homology or similarity.

Preferred nucleic acids encode a polypeptide having at least one bioactivity of a Pitx3 polypeptide, and can be full length polypeptide or a bioactive fragment of a polypeptide. A bioactive polypeptide is preferably at least 60% homologous, more preferably 70% homologous and most preferably 80% homologous with an amino acid sequence set forth in SEQ ID NOS. 3, 7, 9 or 30. Nucleic acids which encode bioactive polypeptides at least about 90%, more preferably at least about 95%, and most preferably at least about 98–99% homology, or identical, with an amino acid sequence represented in one of SEQ ID NOS. 3, 7, 9 or 30 are also within the scope of the invention.

Accordingly, the invention provides nucleic acids encoding a DNA binding domain of a Pitx3 polypeptide, and comprising preferably the homeobox domain. Assays for determining the location of a DNA binding domain in proteins include gel retardation assays, well known in the art. Briefly, recombinant proteins comprising various portions of a Pitx3 polypeptide can be produced and their interaction with DNA can be measured by incubation with a DNA target sequence and separation of the complexes by gel electrophoresis. The DNA target sequence of a Pitx3 polypeptide can be determined, e.g., by binding site selection experiments, well known in the art. Binding site selection experiments are performed by incubation of a DNA binding protein, e.g., a Pitx3 polypeptide, with a degenerate pool of labeled double stranded oligonucleotides and isolation of the oligonucleotides which interact specifically with the DNA binding protein. Individual oligonucleotides are then sequenced.

In another embodiment, the invention provides nucleic acids encoding a domain capable of interacting with another protein. Numerous transcription factors have a dimerization domain and/or domains interacting with specific factors, e.g., factors of the basal transcription machinery, e.g., TATA box binding (TBP) protein, TAFs (Transcriptional Activation Factors), or coactivators. Such domains can be identified by, e.g., direct interaction experiments using recombinantly produced portions of Pitx3 polypeptides and recombinant or isolated basal transcription machinery proteins. The nucleotide sequence of numerous factors from the basal transcription machinery is publically available in GenBank, which is freely available on the internet.

Yet other preferred nucleic acids encode a transcriptional activation or repression domain. The location of such domains in Pitx3 polypeptides can be determined by, e.g., transfection experiments using GAL4 fusion proteins comprising at least a portion of a Pitx3 polypeptide and a reporter construct containing GAL4 DNA binding sites.

Still other preferred nucleic acids of the present invention encode a Pitx3 polypeptide which is comprised of at least 2, 5, 10, 25, 50, 100, 150 or 200 amino acid residues. However, a nucleic acid encoding a peptide having any number of amino acids is within the scope of the invention, so long as the nucleic acid has a novel nucleotide sequence.

The nucleic acids of the invention may comprise a signal sequence, whether from the native nucleic acid or from a heterologous nucleic acid. In fact, in certain embodiments of the invention, it may be desirable to produce a secreted form of the proteins of the invention.

The nucleic acid of the invention may also encode a polypeptide which is fused in frame to a marker sequence which allows, e.g., for purification of the polypeptide of the present invention. In a preferred embodiment, the marker sequence is a hexahistidine tag supplied by a PQE-9 vector to provide for purification of the fusion protein in the case of a bacterial host or an HA tag when a mammalian host, e.g. COS-7 cells, are used. In another embodiment, the marker sequence is a 16 amino acid portion of the *Haemophilus influenza* hemagglutinin protein, or a peptide from the myc proto-oncogene.

In another embodiment, the invention provides a nucleic acid encoding a Pitx3 polypeptide comprising an amino acid sequence which is at least about 70%, at least about 80%, at least about 85%, at least about 90%, at least about 95% and more preferably at least about 98% homologous or identical to a sequence of at least about 10, preferably at least about 12, at least about 15, at least about 17, at least about 20, and most preferably at least about 25 consecutive amino acid residues of SEQ ID NOS. 3, 7, 9 or 30.

Other nucleic acids within the scope of the invention include an intron such as a sequence set forth in FIG. 3, an intron-exon border, or promoter, or portion thereof A genomic DNA encoding a Pitx3 polypeptide can be isolated, e.g., by screening a genomic DNA library according to methods known in the art. The site of initiation of transcription (thus the 3' end of the promoter) can be determined by, e.g., primer extension on mRNA or cDNA.

For gene therapy, preferably the gene is administered to a subject in an expression vector, i.e. a nucleic acid encoding a polypeptide, operably linked to at least one transcriptional regulatory sequence. "Operably linked" is intended to mean that the nucleotide sequence is linked to a regulatory sequence in a manner which allows expression of the nucleotide sequence. Regulatory sequences are art-recognized and are selected to direct expression of the subject polypeptides. Accordingly, the term "transcriptional regulatory sequence" includes promoters, enhancers and other expression control elements. Such regulatory sequences are described in Goeddel; *Gene Expression Technology: Methods in Enzymology* 185, Academic Press, San Diego, Calif. (1990). In one embodiment, the expression vector includes a recombinant gene encoding a peptide having an agonistic activity of a Pitx3 polypeptide, or alternatively, encoding a peptide which is an antagonistic form of a Pitx3 polypeptide. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject Pitx3 polypeptides. Thus, the invention features expression vectors for in vivo or in vitro transfection and expression of a Pitx3 polypeptide, in particular for expression of a Pitx3 polypeptide in cells so as to reconstitute the function of, or alternatively, abrogate the function of a Pitx3 polypeptide. This could be desirable, for example, when the naturally-occurring form of the polypeptide is mis-expressed; or to deliver a form of the polypeptide which alters transcription of target genes in a tissue.

Pitx3 Polypeptides and Protein Therapeutics

The invention provides isolated naturally occurring Pitx3 polypeptides as well as recombinantly produced or synthetic Pitx3 polypeptides and portions thereof Preferred Pitx3 polypeptides are vertebrate polypeptides, even more preferably mammalian polypeptides and most preferably human polypeptides. Preferred polypeptides have the amino acid sequence set forth in SEQ ID NOS. 3, 7, 9 or 30.

Preferred Pitx3 polypeptides comprise an amino acid sequence from SEQ ID NOS. 3, 7, 9 or 30. Yet other preferred Pitx3 polypeptides are those which are encoded by any of the nucleic acid molecules described in the above-section drawn to "Nucleic Acids and Gene Therapeutics". For example, polypeptides comprising one or more particular motifs and/or domains or to arbitrary sizes, for example, at least 5, 10, 25, 50, 75, 100, 125, 150 amino acids in length are within the scope of the present invention.

Particularly preferred polypeptides of the invention are those which have a certain degree of similarity or identity with an amino acid sequence set forth in SEQ ID NOS 3, 7, 9 or 30. Such polypeptides include those which are at least about 60%, 70%, 75%, 80%, 85%, 90%, 95%, 98%, or 99% homologous or identical to all of or a portion of the amino acid sequence set forth in SEQ ID NOS. 3, 7, 9 or 30. For example, a polypeptide of the invention can have a certain degree of homology (or similarity) or identity with a specific domain of Pitx3, such as the homeobox domain and/or the 14 amino acid C-terminal domain. Alternatively, a polypeptide of the invention can have a certain degree of homology or identity with a region of a Pitx3) polypeptide having SEQ ID NOS. 3, 7, 9 or 30 located outside of a specific domain, such as the homeobox domain and/or the 14 amino acid C-terminal domain. A polypeptide of the invention can also have a certain decree of homology or identity with a region of a Pitx3 polypeptide having SEQ ID NOS. 3, 7, 9 or 30 located upstream of the homeobox domain. The term "a certain degree of homology or identity" refers to at least about 60%, 70%, 75%, 80%, 85%, 90%, 95%, 98%, or 99% homology or identity.

In one embodiment, the invention provides a Pitx3 polypeptide comprising a domain mediating the interaction with another molecule, such as a nucleic acid, such as a target DNA binding protein. Accordingly, the invention provides Pitx3) polypeptides comprising a domain of a Pitx3) polypeptide having SEQ ID NOS. 3, 7, 9 or 30, or a homolog thereof, which is capable of interacting with a target nucleic acid sequence.

Polypeptides within the scope of the invention can be agonists or antagonists of Pitx3 polypeptides. Antagonists can be, e.g., dominant negative mutants. In one embodiment of the invention, an agonist is a protein which is capable of binding to a target DNA sequence, but does not activate or repress transcription as a wild-type Pitx3 polypeptide would. Agonists of Pitx3 polypeptides can be used, e.g., to modulate expression of genes whose expression is controlled by Pitx3, i.e., target genes. Target genes can be identified, e.g., by identifying, genes having, a Pitx3 DNA target sequence in their promoter, and confirming that they are target genes, e.g., transfection experiments using reporter genes under the control of a promoter region from the potential target gene.

The present invention also makes available isolated Pitx3 polypeptides, which are isolated from, or otherwise substantially free of other cellular proteins. The term "substantially free of other cellular proteins" (also referred to herein as "contaminating, proteins") or "substantially pure or purified preparations" are defined as encompassing preparations of polypeptides having less than about 20% (by dry weight) contaminating protein, and preferably having less than about 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least about 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified preparations will lack any contaminating proteins from the same animal from which the subject polypeptide is normally produced, as can be accomplished by recombinant expression of, for example, a human protein in a non-human cell.

Isolated peptidyl portions of Pitx3 polypeptides can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "functional") or mutant Pitx3 polypeptide.

The present invention further pertains to methods of producing the subject polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant polypeptide is a fusion protein containing a domain which facilitates its purification, such as GST fusion protein or poly(His) fusion protein.

Moreover, it will be generally appreciated that, under certain circumstances, it may be advantageous to provide homologs of one of the subject Pitx3 polypeptides, which function in a limited capacity as one of either an agonist (mimetic) or an antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of Pitx3 polypeptides.

Homologs of each of the subject polypeptides can be generated by mutagenesis, such as by discrete point mutation(s), or by truncation. For instance, mutation can give rise to homologs which retain substantially the same, or merely a subset, of the biological activity of the polypeptide from which it was derived. Alternatively, antagonistic forms of the protein can be generated which are able to inhibit the function of the naturally occurring form of the protein. In addition, agonistic forms of the protein may be generated which are constitutively active. Thus, the Pitx3 polypeptide and homologs thereof, as provided herein may be either positive or negative regulators of gene expression.

The recombinant polypeptides of the present invention also include homologs of Pitx3 which are resistant to proteolytic cleavage, as for example, due to mutations which alter ubiquitination or other enzymatic targeting associated with the protein.

Polypeptide agonists or antagonists as discussed herein may also be chemically modified to create derivatives by forming covalent or aggregate conjugates with other chemical moieties, such as glycosyl groups, lipids, phosphate, acetyl groups and the like.

Covalent derivatives of proteins can be prepared by linking the chemical moieties to functional groups on amino acid sidechains of the protein or at the N-terminus or at the C-terminus of the polypeptide.

Modification of the structure of the subject polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (I) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, W H Freeman and Co.: 1981). Whether a change in the amino acid sequence of a peptide results in a functional homolog (e.g. functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject agonist or antagonist polypeptides as well as truncation mutants, and is especially useful for identifying potential variant sequences (e.g. homologs) that are functional in modulating a Pitx3 activity. The purpose of screening such combinatorial libraries is to generate, for example, novel compounds which can act as either agonists or antagonist, comprise some, but not all Pitx3 activities, or alternatively, compounds which possess novel activities all together.

In one embodiment, the variegated library of variants is generated by combinatorial mutagenesis at the nucleic acid level, and is encoded by a variegated gene library. For instance, a mixture of synthetic oligonucleotides can be enzymatically ligated into gene sequences such that the degenerate set of potential sequences are expressible as individual polypeptides, or alternatively, as a set of larger fusion proteins (e.g. for phage display) containing the set of sequences therein.

There are many ways by which such libraries of potential Pitx3 homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules,* ed. A. G. Walton, Amsterdam: Elsevier pp 273–289; Itakura et al. (1984) *Annu. Rev. Biochem.* 53:323; Itakura et al. (1984) *Science* 198:1056; Ike et al. (1983) *Nucleic Acid Res.* 11:477). Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87:6378–6382; as well as U.S. Pat. Nos. 5,223,409, 5,198,346, and 5,096,815).

Likewise, a library of coding sequence fragments can be provided for a clone in order to generate a variegated population of fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for C-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of Pitx3 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature,* 2., In Maenner and Manderick, eds., Elsevier Publishing Co., Amsterdam, pp. 401–410; Delgrave et al., 1993, *Protein Engineering* 6(3):327–331).

The invention also provides for reduction of the agonist or antagonist proteins to generate mimetics, e.g. peptide or non-peptide agents, which are able to modulate at least one activity of Pitx3, such as disrupting binding of a Pitx3 polypeptide to a nucleic acid. Thus, such mutagenic techniques as described above are also useful to map the determinants of the proteins which participate in protein-protein and protein-DNA interactions involved in, for example, binding of the subject polypeptides to proteins which may function upstream (including both activators (enhancers) and repressors of its activity) or to proteins and/or nucleic acids which may function downstream of the polypeptides, whether they are positively or negatively regulated by it. To illustrate, the critical residues of a subject polypeptide which are involved in molecular recognition of a component upstream or downstream of a Pitx3 polypeptide can be determined and used to generate peptidomimetics which competitively inhibit binding of the authentic protein with that moiety. By employing, for example, scanning mutagenesis to map the amino acid residues of each of the subject proteins which are involved in binding other proteins or nucleic acids, peptidomimetic compounds can be generated which mimic those residues of the protein which facilitate the interaction. Such mimetics may then be used to interfere with the normal function of a protein. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

This invention also pertains to a host cell transfected to express a recombinant form of the subject polypeptides. The host cell may be any prokaryotic or eukaryotic cell. Thus, a nucleotide sequence derived from the cloning of vertebrate proteins, encoding all or a selected portion of the full-length protein, can be used to produce a recombinant form of a polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. MAP kinase, p53, WT1, PTP phosphatases, SRC, and the like. Similar procedures, or modifications thereof, can be employed to prepare recombinant polypeptides by microbial means or tissue-culture technology in accord with the subject invention.

The recombinant gene products can be produced by ligating a nucleic acid encoding a protein, or a portion thereof, into a vector suitable for expression in either prokaryotic cells, eukaryotic cells, or both. Expression vectors for production of recombinant forms of the subject polypeptides include plasmids and other vectors. For instance, suitable vectors for the expression of a polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimential Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, Pitx3 polypeptide is produced recombinantly utilizing an expression vector generated by sub-cloning the coding sequence of Pitx3 gene.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Lahoratory Manual*, 2nd Ed., ed. by Sambrook, Fritsch and Maniatis (Cold Spring Harbor Laboratory Press: 1989) Chapters 16 and 17.

In addition to viral transfer methods, such as those illustrated above, non-viral methods can also be employed to cause expression of a subject polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject gene by the targeted cell. Exemplary targeting means of this type include liposomal derived systems, poly-lysine conjugates, and artificial viral envelopes.

In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing polypeptides in a host which produces MAP (e.g., *E. coli* or CM89 or *S. cerevisiae*), or in vitro by use of purified MAP (e.g., procedure of Miller et al., supra).

In other embodiments transgenic animals, which can be produced by methods known in the art, could be used to produce recombinant proteins.

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a protein. For example, the VP6 capsid protein of rotavirus can be used as an immunologic carrier protein for portions of the polypeptide, either in the monomeric form or in the form of a viral particle. The nucleic acid sequences corresponding to the portion of a subject protein to which antibodies are to be raised can be incorporated into a fusion gene construct which includes coding sequences for a late vaccinia virus structural protein to produce a set of recombinant viruses expressing fusion proteins comprising epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an agonist or antagonist protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized to generate an immunogen, wherein a desired portion of a polypeptide is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the polypeptides of the present invention. For example, agonist or antagonist polypeptides can be generated as glutathione-S-transferase (GST-fusion) proteins. Such GST-fusion proteins can enable easy purification of the agonist or antagonist polypeptide, as for example by the use of glutathione-derivatized matrices (see, for example, *Current Protocols in Molecular Biology*, eds. Ausubel et al. (N.Y. John Wiley & Sons, 1991)). Such fusion proteins can also be used to isolate proteins which interact with Pitx3. For example, a cell extract can be poured over an affinity column containing a Pitx3 fusion protein and the proteins binding to the column can then be eluted and identified.

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocol in Molecular Biology*, eds. Ausubel et al. John Wiley & Sons: 1992).

Antisense, Ribozyme and Triplex Therapeutics

Another aspect of the invention relates to nucleic acids that are effective antisense, ribozyme and triplex antagonists of mutant or otherwise defective (e.g., overexpressed) Pitx3 nucleic acids. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a functional Pitx3 polypeptide. Alternatively, the antisense construct is an oligonucleotide probe which is generated ex vivo and which, when introduced into the cell causes inhibition of expression by hybridizing with the mRNA and/or genomic sequences of a Pitx3 gene.

Antisense molecules of the invention can be any nucleic acid or complement thereof described in the section entitled "Nucleic Acids and Gene Therapeutics". Antisense molecules within the scope of the invention can also be nucleic acids hybridizing to a portion of (a) a nucleic acid encoding a protein which regulates expression of a Pitx3 gene; (b) a gene whose expression is regulated by Pitx3; or (c) a gene encoding a protein interacting with a Pitx3 polypeptide.

Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668. With respect to antisense DNA, oligodeoxyribonucleotides derived from the translation initiation site, e.g., between the −10 and +10 regions of the Pitx3 translation initiation site are preferred.

Antisense approaches involve the design of oligonucleotides (either DNA or RNA) that are complementary to Pitx3 mRNA or mRNA of gene whose expression is modulated by Pitx3 or genes encoding proteins which interact with Pitx3. The antisense oligonucleotides will bind to the mRNA transcript (e.g. a mutant transcript) and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides complementary to either the 5' or 3' untranslated, non-coding regions of a gene, e.g. Pitx3 gene can be used in an antisense approach to inhibit translation of endogenous mRNA, e.g. Pitx3 mRNA. Whether designed to hybridize to the 5', 3' or coding region of an mRNA, antisense nucleic acids should be at least six nucleotides in length, and are preferably oligonucleotides ranging from 6 to about 50 nucleotides in length. In certain embodiments, the oligonucleotide is at least about 10 nucleotides, at least about 17 nucleotides, at least about 25 nucleotides, or at least about 50 nucleotides long.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., (1989) *PNAS USA* 86:6553–6556; Lemaitre et al. (1987) *PNAS* 84:648–652; PCT Publication No. WO 88/09810, published Dec. 15, 1988) or the blood-brain barrier (see, e.g., PCT Publication No. WO 89/10134, published Apr. 25, 1988), hybridization-triggered cleavage agents. (See, e.g., Krol et al. (1988) *Bio Techniques* 6:958–976) or intercalating agents. (See, e.g., Zon (1988) *Pharm. Res.* 5:539–549). To this end, the oligonucleotide may be conjugated to another molecule, e.g., a peptide, hybridization triggered cross-linking, agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3 -amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe, et al. (1996) *PNAS USA* 93:14670 and in Eglom, et al. (1993) *Nature* 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al. (1987) *Nucl. Acids Res.* 15:6625–6641). The oligonucleotide is a 2'-0-methylribonucleotide (Inoue et al. (1987) *Nucl. Acids Res.* 15:6131–6148), or a chimeric RNA-DNA analogue (Inoue et al. (1 987) *FEBS Lett.* 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, *Nucl. Acids Res.* 16:3209), methylphosphonate oligonucleotides can be prepared by use of controlled pore glass polymer supports (Sarin et al. (1988, *PNAS USA* 85:7448–7451), etc.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

A preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous transcript and thereby prevent translation of the mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon (1981) Nature 290:304–310), the promoter contained in the 3' long terminal repeat of Rous sarcoma virus (Yamamoto et al. (1980) Cell 22:787–797), the herpes thymidine kinase promoter (Wagner et al. (1981) PNAS USA 78:1441–1445), the regulatory sequences of the metallothionein gene (Brinster et al. (1982) Nature 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue; (e.g., for brain, herpes virus vectors may be used), in which case administration may be accomplished by another route (e.g., systematically).

The invention further provides ribozymes for regulating a Pitx3 activity. Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding agonist or antagonist proteins (further described herein).

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Ribozyme molecules are described in PCT International Publication WO90/11364, published Oct. 4, 1990; Sarver et al., 1990, and Science 247:1222–1225. While ribozymes that cleave mRNA at site specific recognition sequences can be used to destroy mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585–591. There are typically hundreds of potential hammerhead ribozyme cleavage sites within the nucleotide sequence of a gene, e.g. Pitx3 gene. Preferably the ribozyme is engineered so that the cleavage recognition site is located near the 5' end of the mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a gene.

As in the antisense approach, the ribozymes can be composed of modified oligonucleotides (e.g. for improved stability, targeting, etc.) and should be delivered to cells which express the gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous Pitx3 messages and inhibit translation. Because ribozymes unlike antisense molecules, are catalytic, a lower intracellular concentration is required for efficiency.

Endogenous mutant Pitx3 gene expression can also be reduced by inactivating or "knocking out" the Pitx3 gene or its promoter using targeted homologous recombination. (e.g., see Smithies et al. (1985) Nature 317:230–234; Thomas & Capecchi (1987) Cell 51:503–512; Thompson et al. (1989) Cell 5:313–321; each of which is incorporated by reference herein in its entirety). For example, a wildtype, functional Pitx3 (or a completely unrelated DNA sequence) flanked by DNA homologous to the endogenous mutant Pitx3 gene (either the coding regions or regulatory regions of the Pitx3 gene) can be used, with or without a selectable marker and/or a negative selectable marker, to transfect cells that express mutant Pitx3 in vivo. Insertion of the DNA construct, via targeted homologous recombination, results in inactivation of the mutant Pitx3 gene. Such approaches are particularly suited for generating transgenic animals, where modifications to ES (embryonic stem) cells can be used to generate animal offspring with an inactive Pitx3 e.g., see Thomas & Capecchi 1987 and Thompson 1989, supra). However this approach can be adapted for use in humans provided the recombinant DNA constructs are directly administered or targeted to the required site in vivo using appropriate viral vectors, e.g., herpes virus vectors for delivery to brain tissue.

Alternatively, endogenous (mutant or wildtype) gene expression can be reduced by targeting deoxyribonucleotide sequences complementary to the regulatory region of the gene (i.e., the promoter and/or enhancers) to form triple helical structures that prevent transcription of the gene in target cells in the body. (See generally, Helene, C. (1991) Anticancer Drug Des. 6(6):569–84; Helene, C., et al. (1992)

Ann, N.Y. *Acad. Sci.,* 660:27–36; and Maher, L. J. (1992) *Bioassays* 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Antibody Therapeutics

Another aspect of the invention pertains to antibodies or antigen binding agents, which are specifically reactive with a Pitx3 polypeptide, either wildtype or mutant Pitx3. The term "Pitx3 binding agent" as used herein, refers to an agent, e.g., a protein which interacts specifically with a Pitx3 polypeptide. Preferred Pitx3 binding agents are antibodies or derivatives thereof, which are further described infra. Pitx3 binding agents can be used, e.g., for treating or preventing a disease caused by, or contributed to by an aberrant Pitx3 activity in a subject, by administering to the subject an effective amount of a Pitx3 binding agent or nucleic acid encoding a Pitx3 binding agent. For example, a Pitx3 binding agent can inhibit at least partly an aberrant activity of a mutated or overexpressed Pitx3 polypeptide. Also within the scope of the invention are Pitx3 binding agents which are capable of interacting specifically with a mutated form of a Pitx3 polypeptide, such as a polypeptide having the amino acid sequence set forth in SEQ ID NO. 9. Another preferred antibody interacts specifically with a Pitx3 protein having an Arginine at position 13 of the protein. Preferably the antibody or Pitx3 binding agent is administered in a delivery complex or in conjunction with an agent that allows entry of the antibody into cell nuclei. Alternatively, it can be produced in the target cell.

In another embodiment, a Pitx3 binding agent is used as a target molecule. For example, a Pitx3 binding agent can be linked to cytotoxic molecule, such as to lyse a cell expressing or overexpressing Pitx3 or a mutated form thereof.

In yet another embodiment, a Pitx3 binding agent is used as a prognostic or diagnostic agent. For example, a Pitx3 binding agent can be used to determine the amount of Pitx3 or mutated Pitx3 in a subject. In one embodiment, the amount of Pitx3 polypeptide or mutated Pitx3 polypeptide is determined in vivo. Alternatively, the amount of Pitx3 polypeptide or mutated polypeptide is determined in a tissue sample that is obtained from the subject. In a specific embodiment, a Pitx3 binding agent is linked to a marker protein for detecting a Pitx3 polypeptide or determining its polypeptide level.

Various methods can be used to produce Pitx3 binding agents. For example, by using immunogens derived from a Pitx3 polypeptide, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide. Techniques for conferring immunogenicity on a protein or peptide include conjugation to carriers or other techniques well known in the art. An immunogenic portion of an agonist or antagonist protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a Pitx3 polypeptide of a mammal, e.g. antigenic determinants of a protein represented in Bach, I. et al., (1990) *Genomics* 8:155–164 or closely related homologs (e.g. at least 92% homologous, and more preferably at least 94% homologous).

Following immunization of an animal with an antigenic preparation of an agonist or antagonist polypeptide, antisera can be obtained and, if desired, polyclonal antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) *Nature,* 256: 495–497), the human B cell hybridoma technique (Kozbar et al., (1983) *Immunology Today,* 4:72), and the EBV-hybridoma technique to produce human monoclonal antibodies (Cole et al., (1985) *Monoclonal Antibodies and Cancer Therapy,* Alan R. Liss, Inc. pp. 77–96). Hybridoma cells can be screened immunochemically for production of antibodies specifically reactive with an agonist or antagonist polypeptide of the present invention and monoclonal antibodies isolated from a culture comprising such hybridoma cells.

The term "antibody" as used herein is intended to include fragments thereof which are also specifically reactive with one of the subject agonist or antagonist polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The term "antibody" is further intended to encompass modified forms or antibodies or fragments thereof, derivatives of antibodies or fragments thereof. Such modified forms or derivatives include, but are not limited to, bispecific molecules or antibodies, chimeric molecules or antibodies, humanized molecules or antibodies, single chain molecules or antibodies, having affinity for a protein which is conferred by at least one CDR region of an antibody. Modified forms or derivatives of antibodies can be produced recombinantly according to methods known in the art.

Pitx3 binding agents can also be produced in the cell to be targeted, by introduction into the target cell of one or more nucleic acids encoding the one or more Pitx3 binding agents. For example, intracellular antibodies can be produced in the target cell.

Antibodies which specifically bind agonist or antagonist epitopes can also be used in immunohistochemical staining of tissue samples in order to evaluate the abundance and pattern of expression of each of the subject agonist or antagonist polypeptides. Anti-agonist or antagonist antibodies can be used diagnostically in immuno-precipitation and immuno-blotting to detect and evaluate protein levels in tissue as part of a clinical testing procedure. For instance, such measurements can be useful in predictive valuations of the onset or progression of proliferative disorders. Likewise, the ability to monitor protein levels in an individual can allow determination of the efficacy of a given treatment regimen for an individual afflicted with such a disorder. The level of polypeptides may be measured from cells in bodily fluid, such as in samples of cerebral spinal fluid or amniotic fluid, or can be measured in tissue, such as produced by biopsy.

Another application of antibodies of the present invention is in the immunological screening of cDNA libraries constructed in expression vectors such as $\lambda$gt11, $\lambda$gt18–23, $\lambda$ZAP, and $\lambda$ORF8. Messenger libraries of this type, having coding sequences inserted in the correct reading frame and orientation, can produce fusion proteins. For instance, $\lambda$gt11 will produce fusion proteins whose amino termini consist of $\beta$-galactosidase amino acid sequences and whose carboxy termini consist of a foreign polypeptide. Antigenic epitopes of an agonist or antagonist protein, e.g. other orthologs of a particular Pitx3 polypeptide or other paralogs from the same species, can then be detected with antibodies, as, for example, reacting nitrocellulose filters lifted from infected plates with antibodies. Positive phage detected by this assay can then be isolated from the infected plate. Thus, the presence of Pitx3 homologs can be detected and cloned from other animals, as can alternate isoforms (including splicing variants) from humans.

Methods of Treating Diseases

As further described herein, variant forms of Pitx3 proteins have been found in individuals having cataracts, but not in individuals who do not have cataracts. Cataract is the progressive opacification of the lens. Variant forms of Pitx3 were found both in all individuals having the autosomal dominant disease Anterior Segment Mesenchymal Disgenesis (ASMD), in which all affected individuals have cataracts, and in individuals having congenital cataracts. Furthermore, as described herein, Pitx3 is expressed predominantly in lens cells during development, in particular in fiber cells, but most notably in the anterior epithelium and in the equator regions of the lens. As also shown herein, the mouse Pitx3 gene is localized in the same chromosomal region as that of the mutant gene responsible for the phenotype aphakia (ak), which is characterized by small eyes lacking a lens and closed eyelids (first described in Varnum and Stevens (1968) J. Hered. 59:147). Thus, Pitx3 is involved in the development of the lens and is involved in diseases or disorders of the lens.

Pitx3 is also likely to be involved in diseases or disorders of other eye structures. In fact, Pitx3 is also expressed in the eye muscles and the eyelid during embryonic development. Furthermore, ASMD, is also associated with symptoms other than cataracts, including poor visual acuity, abnormal corneal endothelium. Accordingly, the invention provides more generally methods and compositions for treating and preventing disorders of the eye, referred to as ocular disorders.

A preferred disease that can be treated according to the methods of the invention is ASMD. ASMD is an anterior segment abnormality characterized by a strong defects in visual acuity, corneal abnormalities with or without synechiae. In particular, affected individuals have corneal opacities and lens opacities. Corneal opacities are associated with central endothelial abnormalities. Furthermore, all affected individuals have cataracts and some have optic nerve abnormalities and develop glaucoma. This disorder is further described in Hittner et al. (1982) *Am. J. Ophthal.* 93:57.

Based at least on the fact, that ASMD, which is associated with a mutated form of Pitx3, it is likely, that similar diseases or at least disorders or conditions that have at least some of the characteristics of ASMD also involve an abnormal form of Pitx3. For example, ASMD is a disease associated with anterior segment abnormalities, in particular abnormalities of the first axial migrating wave of mesenchyme from the margin of the optic cup, which produces the corneal endothelium and the trabecular meshwork. Such abnormalities are also referred to as dysembryogenesis of the first mesenchymal wave and include central abnormalities, such as central keratoconus, Peter's anomaly (characterized by central congenital corneal opacities) and Descemet's layer defects. A primary mesenchymal defect can also have further development of the ectodermal lens, for example. Individuals having ASMD typically have corneal endothelial abnormalities with or without anterior synechia. These individuals also have variable visual acuity, which can be rather poor, corneal opacities with or without iris adhesions, lens opacities and abnormal optic nerve, such as tilting of the optic nerve or myelination of optic nerve fibers. This disease is also accompanied by optic nerve abnormalities, indicating that this disorder does not affect the anterior segment alone, but may involve any portion of the eye derived from mesenchyme. Thus, the methods of the invention can be used to treat or prevent diseases or disorders relating to anterior segment abnormalities, abnormalities of any portion of the eye derived from mesenchyme, corneal endothelial abnormalities, corneal opacities, and/or lens opacities among others. In one embodiment, cataracts can be treated according to the methods of the invention.

In particular, it is likely that Peter's anomaly can be treated according to the methods of the invention. In fact, Peter's anomaly is believed to result from a failure of the fist axial migratory wave of mesenchyme to reach the central cornea (Kenyon (1975) Exp. Eye Res. 21:125). The ultrastructural manifestation of this disease is a total absence of any endothelium or its secreted Descemet's layer in the central cornea. Other mesenchymal dystrophies that can be treated according to the methods of the invention include primary keratoconus, sclerocornea, and congenital endothelial dystrophy. Other diseases or disorders, which like ASMD, involve an abnormal corneal endothelium, and which accordingly can be treated according to the methods of the invention include Zellweger's syndrome, Conradi's syndrome, and Smith-Lemli-Opitz syndrome.

Yet other diseases or disorders associated with abnormalities of the lens which can be treated according to the methods of the invention include those characterized by an abnormal lens size or shape, such as: microphalda (small lens), aphakia (absence of lens), coloboma of the lens (localized flattening or notching of its margins), sperophakia (round lens), congenital aphakia, and anterior or posterior lent'conus.

All of the diseases cited herein may not only occur in humans, but also in animals, such as domestic animals, in particular dogs and cattle. A list of eye disorders that are known to occur more frequently in certain animals can be found, e.g., at http://vetpathl.afip.mil/CLDavis/syllabi/eye.txt. The methods and compositions of the invention can also be used to treat such animals.

A pharmaceutical composition of the present invention can be, as appropriate, any of the preparations described above, including isolated polypeptides, binding agents, gene therapy constructs, antisense, ribozyme or triplex molecules, peptidomimetics or agents (e.g. small molecules) identified in the drug assays provided herein.

In one aspect, the invention provides a method for preventing or treating in a subject, a disease or condition associated with an aberrant Pitx3, such as an aberrant Pitx3 activity or an aberrant Pitx3 protein and/or nucleic acid, by administering to the subject a therapeutically effective amount of a compound which modulates at least one Pitx3 activity.

Subjects having a disease, which is caused or contributed to by an aberrant Pitx3, e.g., cataracts, can be treated by administration to the subject of a therapeutically effective amount of a Pitx3 therapeutic. Depending on the type of Pitx3 aberrancy, a Pitx3 agonist or Pitx3 antagonist therapeutic can be used for treating the subject. For example, in the case of cataracts and individuals having ASMD, a treatment could consist in administration of a wild-type Pitx3 protein, such as a Pitx3 protein having SEQ ID NO. 7. Optionally, treatment of cataracts or ASMD can further be accompanied by administration of a therapeutic which inhibits the abnormal Pitx3 protein, such as a therapeutic which inhibits its production, e.g., antisense compound. In other diseases or disorders, the appropriate therapeutic can be determined based on assays described herein. For example, a sample obtained from the subject can be analyzed to determine whether the subject has an abnormally high or low Pitx3 polypeptide level or Pitx3 activity or a mutant form of a Pitx3 polypeptide. Assays which can be used for this purpose are further described in the section drawn to prognostic and diagnostic assays. Where the subject has an abnormally high Pitx3 polypeptide level and/or activity, a Pitx3 antagonist therapeutic is administered to the subject. On the other hand, where the subject has an abnormally low Pitx3 polypeptide level and/or activity, a Pitx3 agonist is administered to the subject. Agonist and antagonist compounds are further described below. Therapeutics can also be administered for preventing the development of a disease, by administration to the subject a Pitx3 therapeutic before the first symptoms of the disease or disorder appear.

It is likely, that Pitx3 is involved in modulating cell proliferation, differentiation, and/or cell survival, in particular of cells of the eye, such as lens cells, e.g., epithelial lens cells and fiber cells and endothelial cells. Thus, Pitx3 therapeutics could be used for preventing or treating disorders or diseases that are characterized by an abnormal cell proliferation, differentiation, and/or survival. For example, the disease that can be treated according to the methods of the invention can be a hyper- or hypoproliferative disease. The invention also provides methods for treating diseases characterized by an abnormal cell proliferation, differentiation, and/or survival in a subject, which are not characterized by an abnormal Pitx3 activity. In fact, since Pitx3 is likely to be capable of modulating the proliferative state of a cell (i.e., state of proliferation, differentiation, and or survival of a cell), Pitx3 can be used for treating diseases wherein the abnormal proliferative state of a cell results from a defect other than an abnormal Pitx3 activity. For example, the defect could be in another gene involved in regulating cell proliferation, e.g., a proto-oncogene. Examples of diseases or disorders of the eye, which are likely to be associated with an abnormal proliferation, differentiation or survival of cells in the eye, and which can be treated according to the methods of the invention include colmeal dystrophy, non-attachment of the retina, iris cysts, choroidal hypoplasia or aplesia, scleral ectasia, progressive retical degeneration such as retinal dysplasia, corneal endothelial dysplasia, glaucoma and cataracts.

Hyperproliferative diseases that can be treated with Pitx3 therapeutics include neoplastic and hyperplastic diseases, such as various forms of cancers, and fibroproliferative disorders. Other hyperproliferative diseases that can be treated or prevented with the subject Pitx3 therapeutics include malignant conditions, premalignant conditions, and benign conditions. The condition to be treated or prevented can be a solid tumor, such as a tumor arising in an epithelial tissue of the eye. Accordingly, treatment of such a cancer could comprise administration to the subject of a Pitx3 therapeutic decreasing the interaction of Pitx3 with a target DNA sequence.

The invention also provides methods for preventing the formation and/or development of tumors. For example, the development of a tumor can be preceded by the presence of a specific lesion, such as a pre-neoplastic lesion, e.g., hyperplasia, metaplasia, and dysplasia, which can be detected, e.g., by cytologic methods. Such lesions can be found, e.g., in epithelial tissue. Thus, the invention provides a method for inhibiting progression of such a lesion into a neoplastic lesion, comprising administering to the subject having a preneoplastic lesion an amount of a Pitx3 therapeutic sufficient to inhibit progression of the preneoplastic lesion into a neoplastic lesion.

The invention also provides methods for treating or preventing diseases or conditions in which proliferation of cells is desired. For example, Pitx3 therapeutics can be used to stimulate tissue repair or wound healing, such as after surgery or to stimulate tissue healing from burns. Other diseases in which proliferation of cells is desired are hypoproliferative diseases, i.e, diseases characterized by an abnormally low proliferation of certain cells.

In yet another embodiment, the invention provides a method for treating or preventing diseases or conditions characterized by aberrant cell differentiation. Accordingly, the invention provides methods for stimulating cellular differentiation in conditions characterized by an inhibition of normal cell differentiation which may or may not be accompanied by excessive proliferation. Alternatively, Pitx3 therapeutics can be used to inhibit differentiation of specific cells.

In another embodiment, the invention provides a method for enhancing the survival and/or stimulating proliferation and/or differentiation of cells and tissues in vitro. In a preferred embodiment, Pitx3 therapeutics are used to promote tissue regeneration and/or repair (e.g., to treat lens injury). For example, tissues from a subject can be obtained and grown in vitro in the presence of a Pitx3 therapeutic, such that the tissue cells are stimulated to proliferate and/or differentiate. The tissue can then be administered back to the subject.

A Pitx3 activity can also be agonized by acting on a step located downstream or upstream of Pitx3 in the biochemical pathway in which Pitx3 is involved. For example, in some situations, an agonist of a Pitx3 activity can be a compound which increases the expression of a gene whose expression is regulated by Pitx3. Accordingly, disorders that are contributed to, or caused by, a mutation in Pitx3 that results in a protein that is less active than the wild-type Pitx3, can be treated by administering to the subject a compound which regulates a step located downstream of Pitx3 in the biochemical pathway in which Pitx3 is involved. Similarly, disorders that are caused by, or contributed to, by a level of Pitx3 that is abnormally low relative to the level of Pitx3 in a normal subject, can be treated by administration to the subject having such a disorder of an effective amount of a compound which regulates a step located downstream of Pitx3 in the biochemical pathway in which Pitx3 is involved. Thus, a subject suffering from a disease that is caused by, or contributed to by, a mutation in the Pitx3 gene resulting in abnormally low levels of Pitx3 or abnormally low activity of Pitx3 can be treated by administration to the subject of a compound that effects a step located downstream of Pitx3 in the biochemical pathway in which Pitx3 is involved. The term "agonistic Pitx3 therapeutics" is intended to encompass such compounds.

In another aspect, the invention features compounds that are antagonists of a normal (functional) Pitx3 bioactivity. Such antagonists can decrease a Pitx3 activity by, e.g., decreasing the interation of Pitx3 with a nucleic acid. An antagonists can also decrease a Pitx3 activity by decreasing the level of Pitx3 polypeptide, by, e.g., inhibiting expression of the Pitx3 gene in a cell or by introducing into the cell a transgene encoding a nucleic acid or polypeptide, capable of inhibiting transcription, translation, or protein activity of Pitx3 in a cell in which it is expressed. Accordingly, diseases caused by, or contributed to by, an abnormally high level of Pitx3 or an abnormally potent activity of Pitx3 relative to the level and activity of wild-type Pitx3, can be treated by administering to the subject having such a disease an efficient amount of a compound which decreases the expression of a Pitx3 gene or an operable nucleic acid encoding a Pitx3 antagonistic protein or nucleic acid. Thus, a subject having a disease that is caused by, or contributed to by, a mutation in a Pitx3 gene, resulting in an abnormally high protein level of Pitx3 or an abnormally potent Pitx3 activity can be treated by administration to the subject of an efficient amount of a compound which decreases the protein level or activity of Pitx3.

A Pitx3 activity can also be antagonized by acting on a step located downstream or upstream of Pitx3 in the biochemical pathway in which Pitx3 is involved. For example, in some situations, an antagonist of a Pitx3 activity can be a compound which decreases the expression of a gene whose expression is regulated by Pitx3 or of a gene encoding a protein regulating the expression of a Pitx3 gene. Accordingly, disorders that are contributed to, or caused by, a mutation in Pitx3 that results in a protein that is more active than the wild-type Pitx3 or in abnormally high levels of Pitx3, can be treated by administering to the subject a compound which regulates a step located downstream or upstream of Pitx3 in the biochemical pathway in which Pitx3 is involved. The term "antagonist Pitx3 therapeutics" is intended to encompass such compounds.

Effective Dose

Toxicity and therapeutic efficacy of the above-described compounds can be determined by standard pharmaceutical procedures in cell cultures, lens cell cultures (which can be prepared as described herein) or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosages for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, topical application and/ or intraocularly.

For such therapy, the compositions of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous. For injection, the compositions of the invention can be formulated in liquid solutions, preferably in physiologically compatible buffers such as Hank's solution or Ringer's solution. In addition, the compositions may be formulated in solid form and redissolved or suspended immediately prior to use. Lyophilized forms are also included.

The therapeutic compositions of the invention are preferably formulated as ophthalmic eye drops or aerosols. The compounds of the invention can also be formulated as gels or ointments, or can be incorporated into collagen or a hydrophilic polymer shield. The materials can also be inserted as a contact lens or reservoir or as a subconjunctival formulation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insulator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the nucleic acids of the invention are formulated into ointments, salves, gels, or creams as generally known in the art.

In clinical settings, gene delivery systems for the therapeutic Pitx3 gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91:3054–3057). A Pitx3 gene, or a sequence homologous thereto can be delivered in a gene therapy construct by electroporation using techniques described, for example, by Dev et al. ((1994) *Cancer Treat Rev* 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Diagnostic and Prognostic Assays

The invention further provides methods for determining whether a subject has or is at risk of developing a disease caused by, or contributed to by, an aberrant Pitx3, e.g., an aberrant Pitx3 activity, or associated with an abnormal Pitx3 gene or protein. In a preferred embodiment, the invention provides diagnostic methods for diseases or disorders of specific structures in the eye, e.g., lens. A preferred disease that can be diagnosed according to the methods of the invention is the increased risk of developing cataract, in particular early in life, such as occurs in ASMD. As shown herein, the formation of cataracts has been shown to be associated with mutations or variations in the Pitx3 gene and protein. For example, a mutated Pitx3 was shown to cosegregate with individuals having ASMD which have cataracts and a second mutant or variant of Pitx3 was found in a case of congenital cataract.

In one embodiment, the diagnostic method comprises determining whether a subject has an abnormal mRNA and/or protein level of Pitx3, or abnormal Pitx3 mRNA or protein, such as by Northern blot analysis, in situ hybridization, immunoprecipitation, Western blot hybridization, or immunohistochemistry. According to the method, cells are obtained from a subject and the protein or mRNA level of Pitx3, wild-type and/or mutant, is determined and compared to the protein or mRNA level of Pitx3 in a healthy subject. An abnormal level of a wild-type or mutated Pitx3 polypeptide or mRNA might be indicate that the subject has or is at risk of developing a disease associated with an abnormal Pitx3.

In another embodiment, the diagnostic method comprises measuring at least one activity of Pitx3. For example, the level of expression of genes which are regulated by Pitx3 can be determined. Alternatively, the extent of interaction of Pitx3 with a nucleic acid can be determined. Comparison with results from similar experiments performed in healthy subjects will be indicative whether a subject has an abnormal Pitx3 activity.

The invention also provides numerous diagnostic and prognostic methods comprising determining whether a genetic lesion is present in a Pitx3 gene in a subject, such as a 17 base pair insertion which is associated with cataract development and ASMD and an amino acid substitution associated with congenital cataract. A genetic lesion can be any difference present in the gene of a subject which is not present in a healthy subject who is not at risk of developing a disease associated with aberrant Pitx3 activity. Thus, a genetic lesion can be a point mutation, such as a deletion, addition or substitution of a nucleotide. A genetic lesion can also be a deletion, addition, or substitution of more than one nucleotide. A genetic lesion can also be a chromosomal rearrangement, such as a translocation. The genetic lesion can be in any portion of the Pitx3 gene, e.g. promoter, enhancers, exons, introns, translated or untranslated regions. Accordingly, the invention provides methods for determining the presence of a genetic lesion in a Pitx3 gene and/or regulatory sequence thereof These methods include, but are not limited to, methods involving sequence analysis, Southern blot hybridization, restriction enzyme site mapping, and methods involving detection of absence of nucleotide pairing between the nucleic acid to be analyzed and a probe. These and other methods are further described infra.

Also within the scope of the invention are probes and primers for use in prognostic or diagnostic assays. For instance, the present invention provides a probe and/or primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of a sense or anti-sense sequence of wild-type or mutant Pitx3 nucleic acid sequence. Preferred primers and probes are further described in the section entitled "Pitx3 Nucleic Acids and Gene Therapeutics". In preferred embodiments, a probe comprises a label group attached thereto and able to be detected, e.g. the label group is selected from amongst radioisotopes, fluorescent compounds, enzymes, and enzyme co-factors.

In preferred embodiments, the methods for determining whether a subject is at risk for developing a disease associated with an aberrant Pitx3 activity is characterized as comprising detecting, in a sample of cells from the subject, the presence or absence of a genetic lesion characterized by at least one of (i) an alteration affecting the integrity of a gene encoding a Pitx3 polypeptide, or (ii) the misexpression of the Pitx3 gene. To illustrate, such genetic lesions can be detected by ascertaining the existence of at least one of (i) a deletion of one or more nucleotides from a Pitx3 gene, (ii) an addition of one or more nucleotides to a Pitx3 gene, (iii) a substitution of one or more nucleotides of a Pitx3 gene, (iv) a gross chromosomal rearrangement of a Pitx3 gene, (v) a gross alteration in the level of a messenger RNA transcript of a Pitx3 gene, (vii) aberrant modification of a Pitx3 gene, such as of the methylation pattern of the genomic DNA, (vii) the presence of a non-wild type splicing pattern of a messenger RNA transcript of a Pitx3 gene, (viii) a non-wild type level of a Pitx3 polypeptide, (ix) allelic loss of a Pitx3 gene, and/or (x) inappropriate post-translational modification of a Pitx3 polypeptide. As set out below, the present invention provides a large number of assay techniques for detecting lesions in a Pitx3 gene.

For example, in a preferred embodiment, the presence of the 17 base pair insertion in a Pitx3 gene which is associated with cataracts and with ASMD, can be detected by hybridization of genomic DNA from any cell of a subject, such as a blood cell, with a probe comprising a nucleotide sequence which is identical to or complementary to the 17 base pair insertion (GCCCTGCAGGGCCTGGG; SEQ ID NO. 28). Alternatively, the insertion can also be detected by PCR amplification of a region that would comprise the insertion. These hybridization or PCR analyses can be performed on genomic DNA or on RNA. Furthermore, since the insertion results in a frameshift mutation, the mutated Pitx3 protein has a different C-terminal region and can thus be detected in a cell which normally expresses Pitx3 (e.g., a lens cell) by using an antibody which is specific to the mutated form. These and other diagnostic methods are further described below, in a general manner. The single nucleotide substitution in codon 13 that is associated with congenital cataracts can be detected by various method, including any of the ones described herein.

Specific diseases or disorders, e.g., genetic diseases or disorders, are associated with specific allelic variants of polymorphic regions of certain genes, which do not necessarily encode a mutated protein. Thus, the presence of a specific allelic variant of a polymorphic region of a gene in a subject can render the subject susceptible to developing a specific disease or disorder. Polymorphic regions in genes, e.g., Pitx3 genes, can be identified, by determining the nucleotide sequence of genes in populations of individuals. If a polymorphic region is identified, then the link with a specific disease can be determined by studying specific populations of individuals, e.g., individuals which developed a specific disease, such as a cell proliferative disease, e.g., cancer. Thus, the invention provides methods for determining the identity of the allele or allelic variant of a polymorphic region of a Pitx3 gene in a subject, to thereby determine whether the subject has or is at risk of developing a disease or disorder associated with a specific allelic variant of a polymorphic region.

A polymorphic region can be located in any region of a gene, e.g., exons, in coding or non coding regions of exons, introns, and promoter region.

In an exemplary embodiment, there is provided a nucleic acid composition comprising a nucleic acid probe including a region of nucleotide sequence which is capable of hybridizing to a sense or antisense sequence of a Pitx3 gene or naturally occurring mutants thereof, or 5' or 3' flanking sequences or intronic sequences naturally associated with the subject Pitx3 genes or naturally occurring mutants thereof. The nucleic acid of a cell is rendered accessible for hybridization, the probe is contacted with the nucleic acid of the sample, and the hybridization of the probe to the sample nucleic acid is detected. Such techniques can be used to detect lesions or allelic variants at either the genomic or mRNA level, including deletions, substitutions, etc., as well as to determine mRNA transcript levels.

A preferred detection method is allele specific hybridization using probes overlapping the mutation or polymorphic site and having about 5, 10, 20, 25, or 30 nucleotides around the mutation or polymorphic region. In a preferred embodiment of the invention, several probes capable of hybridizing specifically to allelic variants or mutants or wild-type genes are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) *Human Mutation* 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

In certain embodiments, detection of the lesion comprises utilizing a probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the Pitx3 gene (see Abravaya et al. (1995) *Nuc Acid Res* 23:675–682). In a merely illustrative embodiment, the method includes the steps of (i) collecting a sample of cells from a patient, (ii) isolating nucleic acid (e., genomic, mRNA or both) from the cells of the sample, (iii) contacting the nucleic acid sample with one or more primers which specifically hybridize to a Pitx3 gene under conditions such that hybridization and amplification of the Pitx3 gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *PNAS USA* 87:1874–1878), transcriptional amplification system (Kwoh, D. Y. et al. (1989) *PNAS USA* 86:1173–1177), Q-Beta Replicase (Lizardi, P. M. et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in, or allelic variants, of a Pitx3 gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the Pitx3 gene and detect mutations by comparing the sequence of the sample Pitx3 with the corresponding wild-type (control) sequence. Exemplary sequencing reactions include those based on techniques developed by Maxim and Gilbert (*PNAS USA* (1977) 74:560) or Sanger (Sanger et al (1977) *PNAS* 74:5463). It is also contemplated that any of a variety of automated sequencing procedures may be utilized when performing the subject assays (*Biotechniques* (1995) 19:448), including sequencing by mass spectrometry (see, for example PCT publication WO 94/16101; Cohen et al. (1996) *Adv Chromatogr* 36:127–162; and Griffin et al. (1993) *Appl Biochem Biotechnol* 38:147–159). It will be evident to one skilled in the art that, for certain embodiments, the occurrence of only one, two or three of the nucleic acid bases need be determined in the sequencing reaction. For instance, A-tract or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) *Science* 230:1242). In general, the art technique of "mismatch cleavage" starts by providing heteroduplexes formed by hybridizing (labelled) RNA or DNA containing the wild-type Pitx3 sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *PNAS USA* 85:4397; Saleeba et al (1992) *Methods Enzymol* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Pitx3 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a Pitx3 sequence, e.g., a wild-type Pitx3 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations or the identity of the allelic variant of a polymorphic region in Pitx3 genes. For example, single strand conformation polymorphism (SSCP) may be used to detect differences in electrophoretic mobility between mutant and wild type nucleic acids (Orita et al. (1989) *PNAS USA* 86:2766, see also Cotton (1993) *Mutat Res* 285:125–144; and Hayashi (1992) *Genet Anal Tech Appl* 9:73–79). Single-stranded DNA fragments of sample and control Pitx3 nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1 991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) *Biophys Chem* 265: 12753).

Examples of other techniques for detecting point mutations or the identity of the allelic variant of a polymorphic region include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) *Nature* 324:163); Saiki et al (1989) *PNAS USA* 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al (1992) *Mol. Cell Probes* 6:1). It is anticipated that in certain embodiments amplification may also be performed using Taq ligase for amplification (Barany (1991) *PNAS USA* 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al. (1988) *Science* 241:1077–1080. The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) *PNAS USA* 87:8923–8927. In this method, PCR is used to achieve the exponential amplification of target DNA, which is then detected using OLA.

Several techniques based on this OLA method have been developed and can be used to detect specific allelic variants of a polymorphic region of an Pitx3 gene. For example, U.S. Pat. No. 5593826 discloses an OLA using an oligonucleotide having 3'-amino group and a 5'-phosphorylated oligonucleotide to form a conjugate having a phosphoramidate linkage. In another variation of OLA described in Tobe et al. ((1996) *Nucleic Acids Res* 24:3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting single nucleotide polymorphisms in an Pitx3 gene. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No.4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO 91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO 91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al. (1989) *Nucl. Acids. Res.* 17:7779–7784; Sokolov, B. P. (1990) *Nucl. Acids Res.* 18:3671; Syvanen, A. -C., et al. (1990) *Genomics* 8:684–692; Kuppuswamy, M. N. et al. (1991) *PNAS USA* 88:1143–1147; Prezant, T. R. et al. (1992) *Hum. Mutat.* 1:159–164; Ugozzoli, L. et al. (1992) *GATA* 9:107–112; Nyren, P. et al. (1993) *Anal. Biochem.* 208:171–175). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. -C., et al. (1993) *Amer. J. Hum. Genet.* 52:46–59).

For mutations that produce premature termination of protein translation, the protein truncation test (PTT) offers an efficient diagnostic approach (Roest, et. al. (1993) *Hum. Mol. Genet.* 2:1719–21; van der Luijt, et. al. (1994) *Genomics* 20:1–4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

The methods described herein may be performed, for example, by utilizing pre-packaged diagnostic kits comprising at least one probe nucleic acid, primer set; and/or antibody reagent described herein, which may be conveniently used, e.g., in clinical settings to diagnose patients exhibiting symptoms or family history of a disease or illness involving a Pitx3 polypeptide.

Any cell type or tissue may be utilized in the diagnostics described below. In a preferred embodiment a bodily fluid, e.g., blood, is obtained from the subject to determine the presence of a mutation or the identity of the allelic variant of a polymorphic region of a Pitx3 gene. A bodily fluid, e.g., blood, can be obtained by known techniques (e.g. venipuncture). Alternatively, nucleic acid tests can be performed on dry samples (e.g. hair or skin). For prenatal diagnosis, fetal nucleic acid samples can be obtained from maternal blood as described in International Patent Application No. WO 91/07660 to Bianchi. Alternatively, amniocytes or chorionic villi may be obtained for performing prenatal testing.

When using RNA or protein to determine the presence of a mutation or of a specific allelic variant of a polymorphic region of a Pitx3 gene, the cells or tissues that may be utilized must express the Pitx3 gene. Preferred cells for use in these methods include lens cells, which have been shown to express Pitx3 (see Examples). Alternative cells or tissues that can be used, can be identified by determining the expression pattern of the specific Pitx3 gene in a subject, such as by Northern blot analysis.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J. (1992) PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant Pitx3 polypeptides or allelic variant thereof, which are discussed above, may also be used in disease diagnostics and prognostics. Such diagnostic methods, may be used to detect abnormalities in the level of Pitx3 polypeptide expression, or abnormalities in the structure and/or tissue, cellular, or subcellular location of a Pitx3 polypeptide. Structural differences may include, for example, differences in the size, electronegativity, or antigenicity of the mutant Pitx3 polypeptide relative to the normal Pitx3 polypeptide. Protein from the tissue or cell type to be analyzed may easily be detected or isolated using techniques which are well known to one of skill in the art, including but not limited to western blot analysis. For a detailed explanation of methods for carrying out Western blot analysis, see Sambrook et al., 1989, supra at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of Pitx3 polypeptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the Pitx3 polypeptide, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-Pitx3 polypeptide specific antibody is via linkage to an enzyme and use in an enzyme immunoassay (EIA) (Voller, "The Enzyme Linked Immunosorbent Assay (ELISA)", *Diagiostic Horizons* 2:1–7, 1978, Microbiological Associates Quarterly Publication, Walkersville, Md.; Voller, et al. (1978) *J. Clin. Pathol.* 31:507–520; Butler (198 1) *Meth. Enzymol.* 73 :482–523; Maggio, (ed.) *Enzyme Immunoassay,* CRC Press, Boca Raton, Fl., 1980; Ishikawa, et al., (eds.) *Enzynme Immunoassay, Kgaku Shoin, Tokyo,* 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays,* Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a gene or gene product or polymorphic variants can be used to monitor the course of treatment or therapy.

Drug Screening Assays

The present invention facilitates the development of assays which can be used to screen for drugs, i.e., Pitx3 therapeutics, that modulate the expression of a Pitx3 gene or the activity of a Pitx3 polypeptide, which can then be used to treat diseases or disorders associated with an abnormal Pitx3.

The Pitx3 polypeptide used in these assays can be a native or mutant polypeptide isolated from a cell. Alternatively, the Pitx3 polypeptide can be produced recombinantly.

Cell-free in vitro Assays

In one embodiment of the invention, a Pitx3 therapeutics is a drug which modulates the interaction of a Pitx3 polypeptide with another molecule, such as a macromolecule. The molecule can be a nucleic acid, such as a DNA target sequence, a bicoid target sequence. The macromolecule can also be a protein. The molecule with which Pitx3 polypeptide interacts can be a molecule located upstream or downstream of Pitx3 in the biochemical pathway in which Pitx3 is involved. Yet other Pitx3 therapeutics are drugs which modulate expression of a Pitx3 gene.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream molecules. Accordingly, in an exemplary screening assay of the present invention, the compound of interest is contacted with proteins, which may function upstream (including both activators (enhancers) and repressors of its activity) or to proteins and/or nucleic acids (e.g. promoter) which may function downstream of the Pitx3 polypeptide, whether they are positively or negatively regulated by it. To the mixture of the compound and the upstream or downstream molecule (e.g., protein or nucleic acid) is then added a composition containing a Pitx3 polypeptide. Detection and quantification of complexes of Pitx3 with it's upstream or downstream binding molecules (referred to herein as "Pitx3 binding molecule") provide a means for determining a compound's efficacy at antagonizing (inhibiting) or agonizing (potentiating) complex formation between a Pitx3 and a Pitx3 binding molecule, such as a specific DNA target sequence. The efficacy of the compound can be assessed by generating dose response curves from data obtained using various concentrations of the test compound. Moreover, a control assay can also be performed to provide a baseline for comparison. In the control assay, isolated and purified Pitx3 polypeptide is added to a composition containing the Pitx3 binding molecule, and the formation of a complex is quantitated in the absence of the test compound.

Complex formation between the Pitx3 polypeptide and a binding molecule may be detected by a variety of techniques. Modulation of the formation of complexes can be quantitated using, for example, detectably labeled proteins or nucleic acids, such as radiolabeled, fluorescently labeled, or enzymatically labeled Pitx3 polypeptides or nucleic acids, by immunoassay, or by chromatographic detection.

Typically, it will be desirable to immobilize either Pitx3 or its binding molecule to facilitate separation of complexes from uncomplexed forms, as well as to accommodate automation of the assay. Binding of Pitx3 to an upstream or downstream molecule, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/Pitx3 (GST/Pitx3) fusion proteins can be adsorbed onto glutathione sepharose beads (Sigma Chemical, St. Louis, Mo.) or glutathione derivatized microtitre plates.

Other techniques for immobilizing proteins on matrices are also available for use in the subject assay. For instance, a Pitx3 polypeptide or its cognate binding molecule can be immobilized utilizing conjugation of biotin and streptavidin. For instance, biotinylated Pitx3 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with Pitx3 but which do not interfere with binding of upstream or downstream molecule can be derivatized to the wells of the plate, and Pitx3 trapped in the wells by antibody conjugation. As above, preparations of a Pitx3 binding protein and a test compound are incubated in the Pitx3 presenting wells of the plate, and the amount of complex trapped in the well can be quantitated. Exemplary methods for detecting such complexes, in addition to those described above for the GST-immobilized complexes, include immunodetection of complexes using antibodies reactive with the Pitx3 binding element, or which are reactive with the Pitx3 polypeptide and compete with the binding molecule; as well as enzyme-linked assays which rely on detecting an enzymatic activity associated with the binding element, either intrinsic or extrinsic activity. In the instance of the latter, the enzyme can be chemically conjugated or provided as a fusion protein with the Pitx3 binding partner. To illustrate, the Pitx3 binding partner can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating the molecule or Pitx3 polypeptide trapped in the complex, antibodies against the protein, such as anti-Pitx3 antibodies, can be used. Alternatively, the. protein to be detected in the complex can be "epitope tagged" in the form of a fusion protein which includes, in addition to the Pitx3 sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J. Biol Chem* 266:21150–21157) which includes a 10-residue sequence from c-myc, as well as the pFLAG system (International Biotechnologies, Inc.) or the pEZZ-protein A system (Pharamacia, N.J.).

Assays for screening drugs which disrupt the interaction of a DNA binding protein with a nucleic acid can also be performed using, e.g., transcription factor-DNA binding assays, such as those described in U.S. Pat. No. 5,563,036, which is owned by Tularik and is specifically incorporated by reference herein. Other assays for monitoring interaction of a DNA binding factor to DNA are within the skill in the art and include, e.g., gel shift assays, also referred to herein as "EMSA". According to this assay, a purifed Pitx3 protein, or a cellular or nuclear extract prepared from a cell expressing a Pitx3 gene are incubated in the presence of a nucleic acid comprising at least one Pitx3 binding site. Compounds, e.g., competing nucleic acids (for example, yeast tRNA) can be added to reduce or eliminate non specific binding of proteins to the nucleic acid. After incubation for an adequate amount of time, e.g., 20 minutes, the mixture of nucleic acid and protein is then subjected to gel electophoresis allowing for the separation of complexes between nucleic acid and proteins and non complexed nucleic acids and proteins. In a preferred embodiment, the nucleic acid is radioactively labeled and the protein-DNA complex is detected by autoradiography of the gel. Compounds which modulate the interaction between a Pitx3 protein and a DNA target site, can be identified by performing gel shift assays in the presence of varying amounts of test compounds.

Further, an in vitro transcriptional control assay can be used to detect agonists or antagonists of Pitx3 which can be used for treatment of diseases caused by or contributed to by an aberrant Pitx3. For example, an in vitro transcription array can be performed comprising Pitx3, and a reporter construct comprising Pitx3 binding sites and a nuclear extract. A test compound can then be added to the transcription reaction and transcription of the reporter gene is determined according to methods known in the art.

Further, Pitx3 may be translationally or post-translationally modified by processes such as mRNA editing or protein truncation. Assays to specifically monitor these processes can be performed according to protocols, which are well-known in the art and compounds which modulate such modifications can be isolated using such assays.

In yet another aspect of the invention, the subject Pitx3 polypeptides can be used in a "two hybrid" assay (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO 94/10300), for isolating coding sequences for other cellular proteins which bind to or interact with a Pitx3 (e.g., "Pitx3 binding proteins" or "Pitx3bp"). Such proteins can then be used in an assay for isolating Pitx3 therapeutics which modulate Pitx3 activity.

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a Pitx3 polypeptide. The second hybrid protein encodes a transcriptional activation domain fused in frame to a sample gene from a cDNA library. If the bait and sample hybrid proteins are able to interact, e.g., form a Pitx3 dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the Pitx3 and sample proteins.

Cell Based Assays

In addition to cell-free assays, such as described above, cell-based assays for identifying small molecule agonists/antagonists and the like which modulate Pitx3 activity can be performed.

In one embodiment, test compounds are added to primary culture cells or to tissue culture cells expressing Pitx3 for an appropriate amount of time and at least one activity of Pitx3 is measured. In one embodiment, the Pitx3 activity that is measured is the expression of a gene which is modulated by Pitx3 binding.

Primary lens cell cultures can be prepared as follows. New Zealand White rabbit lenses are removed from freshly enucleated eyes and the anterior capsules are isolated and cut into pieces. The capsular pieces, which have adherent lens epithelial cells are cultured in Dulbeccos Modified Eagle Medium supplemented with 10% fetal calf serum 20% Hams' F-12, 1% Non Essential Amino Acids, 1% L-Glutamine and 1% Antibiotic Antimycotic Solution (all from Gibco). After reaching confluence, the cells are passed with 0.05% trypsin and 0.02% EDTA for 10 minutes and split 1:3. The cells are incubated at 37° C. in 5% $CO_2$. Preparations of Pitx3 therapeutics can be tested for modulation of a Pitx3 activity by addition to the cell culture.

For example, cells can be engineered to express Pitx3 genes and a second gene construct containing a Pitx3 response element in operative linkage with a reporter gene construct, such as luciferase or chloramphenicol acetyl transferase, or other reporter gene known in the art. Cells can then be contacted with test compounds. Pitx3 ligands will cause transcriptional activation of the reporter gene as compared to that seen in control cells in the absence of ligand or in the absence of the recombinant Pitx3 or Pitx3 response element-reporter gene construct. For testing antagonist compounds, cells can be contacted with an agonist prior to being contacted with test compounds and an inhibition of reporter gene transcription or product can be detected.

The transgenic or knock-out animals discussed herein may be used to generate cell lines, which can be used in the above-described cell based assays. While primary cultures derived from these transgenic animals of the invention may be utilized, the generation of continuous cell lines is preferred. For examples of techniques which may be used to derive a continuous cell line from the transgenic animals, see Small et al., 1985, Mol. Cell Biol. 5:642–648.

Monitoring the influence of compounds on cells may be applied not only in basic drug screening, but also in clinical trials. In such clinical trials, the expression of a panel of genes may be used as a "read out" of a particular drug's therapeutic effect.

Transgenic and Knock-out Animals

These systems may be used in a variety of applications. For example, the cell- and animal-based model systems may be used to further characterize Pitx3 genes and polypeptides, in particular their role in diseases associated with an aberrant Pitx3. For example, a knock-out animal can be used to determine the effect of total absence of the Pitx3 polypeptide in a animal. Transgenic mice can be used to determine the effect of mutant Pitx3 proteins, and in particular, to isolate drugs for treating or preventing diseases associated with an abnormal Pitx3 protein, such as the mutant Pitx3 protein resulting from the 17 bp insertion or the Pitx3 protein having an Arginine at position 13 of the protein.

In a preferred embodiment, Pitx3 knock-out mice or cells thereof are used in screening assays for identifying drugs which can overcome the defect of a cell resulting from the absence of a Pitx3 polypeptide. Such drugs can then be used to treat subjects having an absence of functional Pitx3 polypeptide or decreased amounts of functional Pitx3 or a Pitx3 polypeptide which is less active than wild-type Pitx3 polypeptide.

Furthermore, crossing of Pitx3 knock-out mice with mice transgenic for a wild-type or mutated Pitx3 gene or portion thereof can have multiple applications. For example, a mouse or other animal, can be created which has only a mutated form of a Pitx3 polypeptide similar to a mutated form found in humans. These mice could be used to identify drugs which remedy the cellular defect caused by this genetic defect.

Thus, the animal- and cell-based models may be used to identify drugs, pharmaceuticals, therapies and interventions which may be effective in treating diseases, such as cataracts, ASMD, and other ocular diseases.

One aspect of the present invention concerns transgenic animals which are comprised of cells (of that animal) which contain a transgene of the present invention and which preferably (though optionally) express an exogenous Pitx3 polypeptide in one or more cells in the animal. A Pitx3 transgene can encode the wild-type form of the polypeptide, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a Pitx3 polypeptide can be essential for many forms of lineage analysis and can additionally provide a means to assess the effects of, for example, lack of Pitx3 expression which might grossly alter development in small patches of tissue within an otherwise normal embryo. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject Pitx3 polypeptides. For example, excision of a target sequence which interferes with the expression of a recombinant Pitx3 gene, such as one which encodes an antagonistic homolog or an antisense transcript, can be designed to activate expression of that gene. This interference with expression of the polypeptide can result from a variety of mechanisms, such as spatial separation of the Pitx3 gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant Pitx3 polypeptide can be regulated via control of recombinase expression.

Use of the cre/loxP recombinase system to regulate expression of a recombinant Pitx3 polypeptide requires the construction of a transgenic animal containing transsgenes encoding both the Cre recombinase and the subject polypeptide. Animals containing both the Cre recombinase and a recombinant Pitx3 gene can be provided through the construction of "double" transgenic animals. A convenient method for providing such animals is to mate two transgenic animals each containing a transgene, e.g., a Pitx3 gene and recombinase gene.

One advantage derived from initially constructing transgenic animals containing a Pitx3 transgene in a recombinase-mediated expressible format derives from the likelihood that the subject polypeptide, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic Pitx3 transgene is silent will allow the study of progeny from that founder in which disruption of Pitx3 mediated induction in a particular tissue or at certain developmental stages would result in, for example, a lethal phenotype.

Similar conditional transgenes can be provided using prokaryotic promoter sequences which require prokaryotic polypeptides to be simultaneous expressed in order to facilitate expression of the Pitx3 transgene. Exemplary promoters and the corresponding trans- activating prokaryotic polypeptides are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a Pitx3 transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where iii vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a Pitx3 polypeptide (either agonistic or antagonistic), and antisense transcript, or a Pitx3 mutant. Further, in such embodiments, the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73 :1260–1264). Efficient infection of the blastomeres is obtained by enzymatic treatment to remove the zona pellucida (*Manipulating the Mouse Embryo,* Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–693 1; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83:9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

In one embodiment, gene targeting, which is a method of using homologous recombination to modify an animal's genome, can be used to introduce changes into cultured embryonic stem cells. By targeting a Pitx3 gene of interest in ES cells, these changes can be introduced into the gernlines of animals to generate chimeras. The gene targeting procedure is accomplished by introducing into tissue culture cells a DNA targeting construct that includes a segment homologous to a target Pitx3 locus, and which also includes an intended sequence modification to the Pitx3 genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a Pitx3 gene function through the use of a targeting transgene construct designed to undergo homologous recombination with one or more Pitx31 genomic sequences. The targeting construct can be arranged so that, upon recombination with an element of a Pitx3 gene, a positive selection marker is inserted into (or replaces) coding sequences of the targeted gene. The inserted sequence functionally disrupts the Pitx3 gene, while also providing a positive selection trait.

Generally, the embryonic stem cells (ES cells ) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp. Morphol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector (described in infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, for example, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the Pitx3 coding sequence, transcriptional regulatory sequence, etc. Typically, less than about 1–5% of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, as the appended Examples describe, the transformed ES cells can be microinjected into blastocytes.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the Pitx3 gene knocked out in various tissues of the offspring by probing the Western blot with an antibody against the particular Pitx3 polypeptide, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986).

Recombinase dependent knockouts can also be generated, e.g. by homologous recombination to insert target sequences, such that tissue specific and/or temporal control of inactivation of a Pitx3 gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

Kits

The invention further provides kits for use in diagnostics or prognostic methods or for treating a disease or condition associated with an aberrant Pitx3 protein. In one embodiment, the kit comprises a pharmaceutical composition containing an effective amount of a Pitx3 therapeutic and instruction for use in treating or preventing a disease or disorder associated with an abnormal Pitx3, e.g., ASMD.

Yet other kits can be used to determine whether a subject has or is likely to develop a disease or condition associated with an aberrant Pitx3. Such a kit can comprise, e.g., one or more nucleic acid probes capable of hybridizing specifically to at least a portion of an Pitx3 gene or allelic variant thereof, or mutated form thereof, such as a probe specifically hybridizing to the 17 base pair insert of the mutated Pitx3 gene characteristic of cataracts and ASMD or to a region overlapping the nucleotide substitution found in congenital cataracts.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis (M. J. Gait ed., 1984);* Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells,* (R. I. Freshney, Alan R. Liss, Inc., 1987); *Immobilized Cells And Enzymes* (IRL Press, 1986); B. Perbal, *A Practical Guide To Molecular Cloning* (1984), the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

EXAMPLES

Isolation of a Pitx3 cDNA

Mouse day-15-embryo (Novagene) and embryonic-carcinoma (Stratagene) cDNA libraries were screened with a random-prime radiolabeled (Boehringer) probe comprising the homeobox region of the Rieg1 (5). Hybridization was carried out in standard hybridization buffer at 50° C. for 18 hours, followed by several washes at room temperature and a one-hour wash at 55° C. in 0.1% SSC and 0.5% SDS. Plasmids from positive plaques were isolated from their Uni-Zap XR or $\lambda$Exlox$^R$ hosts by in vivo excision with R408 helper phage as described by the manufacturer.

Three distinct clones were identified from the $3 \times 10^6$ clones examined. These clones were sequenced and analyzed to construct a cDNA contig, designated r13-2, which was then sequenced in both directions. The sequence was analyzed using the BLASTN and GRAIL search engines.

The cDNA is 1392 bp in length, with a putative polyadenylation signal at positions 1352–1358 and a poly-A tail (FIG. 1). The nucleotide sequence is shown in FIG. 1 and set forth as SEQ ID NO. 1 and has Genbank accession number AF005772. The first codon for methionine associated with the longest open reading frame was found at position 134 of the cDNA. The region 5' of this codon comprises 80% G/C content, which is characteristic of the 5' untranslated regions of vertebrate genes. The protein ascribed to the open reading frame (nucleotides 134–1039) consists of 302 amino acids, which is comparable to proteins encoded by other genes from this family; i.e., the 271- and 317-amino-acid isoforms generated by alternative splicing from Rieg1/Pitx2 (10) and the 315-amino-acid Pitx1/POTX (11). The amino acid sequence of the mouse Pitx3 protein is shown in FIG. 1 and set forth as SEQ ID NO. 3. The nucleotide sequence corresponding to the open-reading frame is set forth as SEQ ID NO. 2.

Comparison of the Pitx3 nucleotide and protein sequences with Genbank sequences identified strong homology with the Rieg1/Pitx2 and Pitx1/POTX nucleotide and protein sequences (see FIG. 2). The most remarkable homology at the protein level is seen in the homeodomain region of Pitx3 (100% identify with the Rieg1/Pitx2 and 97% with Pitx1/POTX) and the region encompassing the 14-amino-acid motif discussed by Semina et al. (5) and Gage et al. (10). These data strongly suggest that Pitx3 represents a third member of the Pitx/Rieg homeobox-containing gene family; hence, the designation Pitx3.

Comparison with the EST sequences in Genbank identified strong homology between the region spanning nucleotides 851–903 of Pitx3 and the 407698 clone of the Soares mouse-embryo NbME13.5 14.5 library from the IMAGE consortium.

Human Pitx3 Gene and cDNA

A human Pitx3 nucleotide sequence was obtained in part from the cDNA clones isolated from the human craniofacial cDNA library and in part from human genomic BAC clones, isolated from the library provided by Research Genetics Company. The nucleotide sequence encoding human Pitx3 is shown in FIG. 3 and set forth as SEQ ID NO. 4. The nucleotide sequence of human Pitx3 excluding intron sequences is set forth in SEQ ID NO. 5. The putative protein encoded by the open reading frame of SEQ ID NOS. 4 and 5 is shown in FIG. 3 and set forth as SEQ ID NO. 7. The nucleotide sequence of the open-reading frame (starting at nucleotide 4 and ending at nucleotide 897 of SEQ ID NO.

4) is set forth as SEQ ID NO. 6. Mouse and human Pitx3 nucleotide sequences are about 90% identical in the coding region and about 80% identical in the 3' untranslated region (UTR). Mouse and human Pitx3 proteins are about 99% identical over the entire protein (overall identity) and 100% identical in the homeodomain region.

Overall identity of human Pitx3 nucleotide sequence (SEQ ID NO. 5) with that of other Pitx genes is about 81% in the coding region. There is no homology between Pitx3 nucleotide sequence and that of Pitx sequences in the 3' and 5' UTRs. Overall identity between the amino acid sequence of human Pitx3 and that of other Pitx proteins is about 40%. There is about 99% identity in the homeodomain.

Mutation of Pitx3 in a Family with Anterior Segment Mesenchymal Dysgenesis (ASMD) and Cataracts The Pitx3 gene was localized to human chromosomal region 10q25 by radiation hybrid mapping. Using neighboring polymorphic markers, the disorder termed Anterior Segment Mesenchymal Dysgenesis (ASMD) disorder, was located to the same chromosomal region. ASMD is characterized by an abnormal development of anterior eye structures and all affected individuals have cataracts.

The sequencing of the fourth Pitx3 exon in the DNA from an affected individual revealed an insertion of a 17 base pair sequence. The nucleotide sequence of this insertion and the exact position of this insertion is shown in FIG. 4. This insertion gives rise to a frameshift, resulting in a Pitx3 protein having a different amino acid sequence at its C-terminus. The nucleotide sequence of this mutant Pitx3 gene is shown in FIG. 5 and set forth as SEQ ID NO. 8 and the putative protein encoded by this nucleotide sequence is shown in FIG. 5 and set forth as SEQ ID NO. 9. The analysis of the Pitx3 gene in individuals of a family with ASMD (the family described in Hittner et al. (1982) Am. J. Ophthalmol. 93:57), indicated that the 17 bp insertion mutation coseg-ragates with the phenotype in this family. In fact, the 17 bp insertion was found in all affected individuals, i.e., individuals showing the symptoms of the disease (14 family members), and was not found in about 300 control chromosomes.

Thus, this Example demonstrates that Pitx3 is associated with the ocular disease ASMD which is characterized by the development of cataracts in all affected individuals.

A Second Variant form of Pitx3 is Found in Congenital Cataract

To further investigate the role of Pitx3 in formation of cataracts, the Pitx3 gene of an individual having congenital cataract was analyzed. The Pitx3 sequence of this individual shows the presence of a single nucleotide difference in the 5' portion of the coding region with the wild-type sequence of human Pitx3 shown in FIG. 3 and set forth as SEQ ID NO. 4. The nucleotide difference is the substitution of the G at position 41 of SEQ ID NO. 4, which is in codon 13 of the open reading frame, of the wild-type Pitx3 with a C in the Pitx3 gene of the individual having congenital cataract. This nucleotide substitution results in a protein having an Asparagine at position 13 of the Pitx3 protein, as opposed to a Serine in the wild-type Pitx3 protein. The nucleotide and amino acid sequences of this variant of Pitx3 are shown in FIG. 6 and set forth as SEQ ID NOS. 29 and 30, respectively.

Thus, this Example further indicates the role of Pitx3 in cataract formation.

Genomic Structure of the Pitx3 Gene

BAC genomic clones for Pitx3 were isolated by screening of a mouse BAC genomic library obtained from Research Genetics with a PCR product containing a specific sequence from the 3' UTR of the gene amplified from 5'-gcaggtctgtggatccat-3' (SEQ ID NO. 10) and 5'-aaaggccctcttcgaagc-3' (SEQ ID NO. 11) forward and reverse primers, respectively. Genomic structure of Pitx3 was identified by primer walking between cDNA and genomic clones.

The Pitx3 gene was found to consist of three exons of 251, 203 and 918 bp each (see Table I, below). Sequencing of the exon-intron junctions revealed the standard donor and acceptor site sequences (see Table I, below). The homeobox region of the gene is interrupted by an intron located in the same position as in other genes from this family (Rieg1/Pitx2 and Pitx1/Potx)—between codons for amino acids 46 and 47 of the homeodomain.

TABLE I

Genomic Structure of Murine Pitx3 gene

| Exon | cDNA | Exon Size | intron/exon | exon/intron |
|---|---|---|---|---|
| 1 | 1–251 | 251 bp | — | gt/gagcgcgcccctt (SEQ ID NO. 12) |
| 2 | 252–454 | 203 bp | ctttctggccctc/ag (SEQ ID NO. 13) | gt/atggcccacctg (SEQ ID NO. 14) |
| 3 | 455–1372 | 918 bp | ctcggatacccgc/ag (SEQ ID NO. 15) | — |

Pitx3 is Expressed Selectively in the Lens During Embryogenesis

This Example shows that Pitx3 is expressed predominantly in the lens in developing mouse embryos, as shown by in situ hybridization.

A 1-kb fragment spanning the 5' UTR region of Pitx3 cDNA and most of the coding sequence (nucleotides 25–1026) was used to create probes for in-situ hybridization. From linearized cDNA, $^{35}$S- or digoxigenin-labeled RNA probes were synthesized using either T3 or T7 RNA polymerase. NIH Swiss mice from Harlan (Indianapolis, Ind.), staged according to Theiler (The House Mouse. Atlas of Embryonic Development. Springer-Verlag, N.Y., 1989)), were used.

Embryonic mice for radioactive in-situ hybridization on sections were fixed overnight at 4° C. in 4% paraformaldehyde in PBS, dehydrated, cleared in Histosol (National Diagnostics), and embedded in Paraplast Plus (Oxford). Seven-micron sections were cut and mounted on Superfrost-plus slides (Fisher) with DEPC-treated water, dried overnight at 40° C., and then stored at room temperature. Before use, the slides were baked at 60° C. overnight and then processed for in situ hybridization as described by Sassoon and Rosenthal (Meth. Enzymol. 225:384 (1993)). Slides were hybridized overnight at 50° C., washed in 5×SSC at 50° C. to remove coverslips, and then washed in 2×SSC, 50% formamide at 60° C. Autoradiography was done with Kodak NTB-2 emulsions. Embryonic mice for whole-mount in-situ hybridization were fixed and processed according to a modification of the method of Harland (Meth. Bio. 36:685 (1991)).

Whole-mount in-situ hybridization of 8.5-, 9-, 10-, 11- and 11.5-dpc (day post coitus) mouse embryos revealed a strong signal in the developing lens beginning with day 11. Hybridization on embryo sections at the eye level of day-11 and day-15 embryos further evidenced Pitx3 expression in the developing lens. At 11 dpc the strong signal is present in the lens vesicle, with expression throughout the developing lens at 15 dpc. including the fiber cells, but most notably in the anterior epithelium and in the equator (bow) regions of the lens. Pitx3 expression was also detected in the eye muscles and the eyelid in day-15 embryos.

Pitx3 is Located on Mouse Chromosome 19 in the Vicinity of Aphakia

A single-strand conformational variation between two mouse strains, C57BL/6J and *M.spretus,* was identified in the 212-bp PCR product spanning nucleotides 455–666 of the Pitx3 cDNA. Interspecific backcross panels from The Jackson Laboratory (Bar Harbor, Me.)—(C57BL/6J *M.spretus*) F1xC57BL/6J (BSB) and (C57BL/6J *M.spretus*) F1x*M.spretus* (BSS)—were then used to map Pitx3 within the mouse genome. Each panel contains 94 backcross animals plus parental controls (47). Complete haplotype data for these crosses are available electronically at http://www.jax.org/resources/documents/cmdata.

As shown in FIG. 7, Pitx3 maps to the distal half of mouse chromosome 19 between markers D19Mit27 and D19Mit4, positioned 32.8 and 35 cM, respectively, from the proximal end of the chromosome according to the MIT map and 43 and 48 cM according to the Mouse Genome Database (MGD) map.

Inspection of the relative positions of other loci and mutant phenotypes incorporated into the MGD map revealed the presence of the mutant phenotype aphakia (ak) 31 cM from the proximal part of chromosome 19. Moreover, the Pitx3 locus is 9.7 cM distal of D19Mit87 according to the BSS cross, while ak is approximately 7 cM distal from the same marker on the MGB map (FIG. 7). Unfortunately, mapping data regarding the ak locus are very restricted and include only its position relative to another mutant phenotype, bm (Varnum, D. S. and Stevens, L. C. (1975) *Mouse News Lett.* 53:35). Inconsistency between the mouse genetic maps and restricted mapping precluded an accurate determination of the relative positions of Pitx3 and ak on the chromosome. Mouse genetic composite maps have broad confidence intervals and generally about a ±10 cM range for gene location.

The aphakia phenotype, characterized by small eyes lacking a lens and closed eyelids, is seen only in homozygous mice, while heterozygous mice appear to be unaffected (Varnum, D. S. and Stevens, L. C. (1968) *J. Hered.* 59(2): 147–150; Zwaan, J. (1975) supra; Kaufman, M. H. (1992) supra). The mapping data, together with the expression pattern of the Pitx3 gene described earlier, suggest Pitx3 as a strong candidate gene for the ak phenotype in mouse.

Mutation Search in the Aphakia Mouse

The Pitx3 gene fragments were amplified from genomic DNA of mouse strain B6xC57BL/ks-ak, homozygous for the aphakia mutant allele obtained from Mouse DNA Resources of The Jackson Laboratory. Oligonucleotides for PCR were designed to amplify the entire coding region and each exon-intron junction sequence. The oligonucleotides used had the following sequences: 5'-cgcactagacctccctcc-3' (SEQ ID NO. 16) and 5'-ggttatcatcactctcgctc-3' (SEQ ID NO. 17), forward and reverse, respectively, for exon 1; 5'-aggaattccttgaggcccct-3' (SEQ ID NO. 18) and 5'-ctcatgtcagggtagcgatt-3' (SEQ ID NO. 19) for intron 1-exon 2; 5'-aggacggctctctgaagaa-3' (SEQ ID NO. 20) and 5'-ccgcagagtcaccagcta-3' (SEQ ID NO. 21) for exon 2-intron 2; 5'-tgacagcctttctcggatac-3' (SEQ ID NO. 22) and 5'-ttgaccgagttgaaggcgaa-3' (SEQ ID NO. 23) for intron 2-exon 3; and 5'-tactcgtacggcaactgg-3' (SEQ ID NO. 24) and 5'-acgagggcaagccagtcta-3' (SEQ ID NO. 25) for exon 3.

Genomic DNA from the aphakia mouse was amplified in a PCR thermocycler (Perkin-Elmer Cetus), with a single four-minute, 94° C. stage followed by 30 cycles comprising three 45-sec. steps at 94° C., 55° C., and 72° C., respectively, in 10 µl total volume of 1 µl Boehringer 10× PCR buffer, 2.5 pmol of each primer, 2-mM in each dNTP, and 0.25 units of Taq polymerase (Boehringer).

The amplified fragments of the aphakia Pitx3 gene were analyzed by single strand conformation variant analysis and sequencing with its generating primers using an ABI PRISM 373 DNA Sequencer. The sequences were compared with the normal sequence. Although no variant band or sequence differences with normal were seen in this experiments, a mutation could be present, e.g, in other regions of the gene, e.g., in a regulatory region or in an alternative exon. These results do not exclude the involvement of Pitx3 in aphakia.

Equivalents

Those skilled in the art will recognize, or be able to ascertain using no more than routine experimentation, many equivalents of the specific embodiments of the invention described herein. Such equivalents are intended to be encompassed by the following claims.

---

What is claimed is:

1. An isolated nucleic acid, which hybridizes to a nucleic acid having the nucleotide sequence set forth in SEQ ID NO. 2, 4, 5, 6, 8 or 29, or the complement thereof, outside of the region encoding the homeobox region and outside of the 14 amino acid C-terminal domain in 6×SSC at 65° C. followed by a wash step in 0.2×SSC at 65° C. and detects a wild-type Pitx3 gene or a Pitx3 gene having an insertion in codon 219 or a frameshift at, or before, codon 219, or a codon 13 encoding an asparagine.

2. The nucleic acid of claim 1, which is from a mammal.

3. The isolated nucleic acid of claim 2, which is from a human.

4. A vector comprising a nucleic acid of anyone of claims 1, 2 and 3.

5. A host cell comprising the vector of claim 4.

6. A method for determining whether a subject is at risk of developing cataracts, comprising determining whether the Pitx3 gene of the subject comprises a genetic lesion consisting of an insertion in codon 219 or a frameshift at, or before, codon 219, or a codon 13 encoding an asparagine, such that the presence of a genetic lesion in the Pitx3 gene of the subject indicates that the subject has or is at risk of developing cataracts.

7. The method of claim 6, wherein the step of determining whether the Pitx3 gene comprises a genetic lesion, comprises the steps of:

(i) contacting a nucleic acid comprising at least a portion of the Pitx3 gene from a subject with at least one nucleic acid probe capable of interacting with a wild-type or mutated Pitx3 gene; and (ii) detecting the formation of a hybrid between the portion of the Pitx3 gene from the subject and the at least one nucleic acid probe, such that the extent of formation of a hybrid between the portion of the Pitx3 gene from the subject and the at least one nucleic acid indicates whether the Pitx3 gene of the subject comprises a genetic lesion.

8. The method of claim 6, wherein the genetic lesion is a nucleotide insertion in codon 219.

9. The method of claim 8, wherein the insertion in codon 219 is a 17 base pair insertion.

10. An isolated nucleic acid of claim 1 comprising the nucleotide sequence of SEQ ID NO: 1, 2, 4, 5, 6, 8 or 29 that encodes the homeobox domain.

11. An isolated nucleic acid of claim 10 further comprising the nucleotide sequence of SEQ ID NO: 1, 2, 4, 5, 6, 8 or 29 that encodes the 14 amino acid C-terminal domain.

12. An isolated nucleic acid comprising a nucleotide sequence which encodes a polypeptide having the amino acid sequence set forth in SEQ ID NO: 3, 7, 9, or 30.

13. An isolated nucleic acid of claim 12 comprising the nucleotide sequence set forth in SEQ ID NO: 1, 2, 4, 5, 6, 8 or 29.

14. An isolated nucleic acid consisting of a nucleotide sequence of at least 25 consecutive nucleotides of SEQ ID NO. 2, 4, 5, 6, 8 or 29, or complement thereof, that is located outside of the sequence encoding the homeobox domain and outside of the sequence encoding the 14 amino acid C-terminal domain.

15. An isolated nucleic acid of claim 14 further comprising a label.

16. An isolated nucleic acid of claim 1 further comprising a label.

17. The method of claim 6, wherein determining whether the Pitx3 gene of the subject comprises a genetic lesion comprises determining alterations in the electrophoretic mobility of a Pitx3 gene or mRNA or portion thereof in the subject, such that a difference in the electrophoretic mobility of a Pitx3 gene or mRNA or portion thereof in the subject relative to a wild-type Pitx3 gene or mRNA or portion thereof indicates that the Pitx3 gene of the subject has a genetic lesion.

18. The method of claim 17, wherein determining whether the Pitx3 gene of the subject comprises a genetic lesion comprises using the technique of single strand conformation polymorphism.

19. The method of claim 6, wherein determining whether the Pitx3 gene of the subject comprises a genetic lesion comprises determining alterations in the Pitx3 protein or portion thereof in the subject, such that a difference in the Pitx3 protein or portion thereof in the subject relative to a wild-type Pitx3 protein or portion thereof indicates that the Pitx3 gene of subject has a genetic lesion.

20. An isolated nucleic acid comprising a nucleotide sequence having an overall sequence identity of at least about 95% with the sequence set forth in SEQ ID NOS. 1, 2, 4, 5, 6, 8 or 29, or complement thereof, as calculated by aligning the two sequences, counting the number of positions at which the nucleotides in both sequences are identical, and converting this number into a percentage of the total number of nucleotides of SEQ ID NO: 1, 2, 4, 5, 6, 8, or 29, respectively, which nucleic acid hybridizes to and detects a wild-type Pitx3 gene or a Pitx3 gene having an insertion in codon 219 or a frameshift at, or before, codon 219, or a codon 13 encoding an asparagine.

21. An isolated nucleic acid consisting of a nucleotide sequence of at least 30 consecutive nucleotides of SEQ ID NO. 2, 4, 5, 6, 8 or 29, or complement thereof, that is located outside of the sequence encoding the homeobox domain and outside of the sequence encoding the 14 amino acid C-terminal domain.

22. The isolated nucleic acid of claim 13 consisting of the nucleotide sequence set forth in SEQ ID NO: 1, 2, 4, 5, 6, 8 or 29.

23. The method of claim 9, wherein the 17 base pair insertion has SEQ ID NO: 28.

24. The method of claim 19, wherein the alteration in the Pitx3 protein results from a frame shift at, or before, codon 219 of the Pitx3 gene of the subject.

25. A method for determining whether a subject is at risk of developing cataracts, comprising determining whether the Pitx3 gene of the subject comprises an insertion in codon 219 or a frameshift at, or before, codon 219, such that the presence of an insertion in codon 219 or a frameshift at, or before, codon 219 of the Pitx3 gene of the subject indicates that the subject is at risk of developing cataracts.

26. A method for determining whether a subject has or is at risk of developing Anterior Segment Mesenchymal Dysgenesis (ASMD), comprising determining whether the Pitx3 gene of the subject comprises an insertion in codon 219 or a frameshift at, or before, codon 219, such that the presence of an insertion in codon 219 or a frameshift at, or before, codon 219 in the Pitx3 gene of the subject indicates that the subject has or is at risk of developing ASMD.

27. The method of claim 26, comprising determining whether the Pitx3 gene of the subject has an insertion of 17 nucleotides having SEQ ID NO: 28 in codon 219.

28. The isolated nucleic acid of claim 12, comprising the coding sequence of SEQ ID NO: 8 or 29.

29. The isolated nucleic acid of claim 28, consisting of the coding sequence of SEQ ID NO: 8 or 29.

30. The method of claim 6, wherein the subject is a human subject.

31. The method of claim 26, wherein the subject is a human subject.

* * * * *

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
        (A) LENGTH: 1392 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

-continued

```
TGCGGCCGCC CAGAGCAGGG GGCGGCCCAC CCGCAGGGTG CCTGGCCCCT GGCCCCTGCC      60

TGCGCTCCAG AACGCCGCCG CCACAGCCAC CACCCGGAGT CTGCCTGCTG CGGGACGCAC     120

TAGACCTCCC TCCATGGAGT TTGGGCTGCT TGGTGAGGCA GAGGCGCGAA GCCCTGCGCT     180

GTCGTTATCG GACGCAGGCA CTCCACACCC TCCGCTTCCA GAACATGGCT GCAAGGGGCA     240

GGAGCACAGT GACTCGGAGA AGGCCTCGGC CTCACTGCCG GGGGGCTCCC CCGAGGACGG     300

CTCTCTGAAG AAGAAGCAGC GGCGGCAGCG CACGCACTTC ACCAGCCAGC AGCTGCAGGA     360

GCTGGAGGCC ACCTTCCAGA GGAATCGCTA CCCTGACATG AGCACCCGCG AAGAGATCGC     420

GGTGTGGACC AACCTCACTG AGGCCCGCGT GCGGGTGTGG TTCAAGAACC GGCGCGCCAA     480

GTGGCGGAAG CGGGAGCGCA GCCAGCAGGC GGAGCTGTGC AAAGGTGGCT TCGCAGCCCC     540

GCTCGGGGGC CTGGTGCCAC CCTACGAGGA GGTGTACCCG GGCTACTCGT ACGGCAACTG     600

GCCGCCCAAG GCTCTCGCCC CGCCGCTCGC CGCCAAGACC TTCCCGTTCG CCTTCAACTC     660

GGTCAACGTG GGGCCTCTGG CTTCACAGCC TGTATTCTCA CCGCCCAGCT CCATCGCCGC     720

TTCTATGGTG CCCTCGGCCG CCGCTGCCCC GGGCACCGTA CCAGGTCCCG GAGCCTTGCA     780

GGGCCTGGGC GGGGCACCCC CCGGGCTGGC TCCAGCCGCC GTGTCCTCCG GGCAGTGTC     840

CTGCCCTTAC GCCTCGGCCG CCGCAGCCGC CGCTGCAGCC GCCTCCTCCC CCTATGTATA     900

CCGGGACCCG TGTAACTCGA GCCTGGCTAG CCTGCGGCTC AAAGCCAAGC AGCACGCCTC     960

TTTCAGCTAT CCCGCCGTGC CCGGGCCGCC GCCGGCCGCT AACCTTAGCC CCTGCCAGTA    1020

CGCCGTGGAA CGGCCGGTGT GAGCCGCAGG TCTGTGGATC CATCCCCGAG GCGGGGCAG    1080

TAATTCACAG CCTCTCCGGA CAGGGGTCGC CTAGACTGGC TTGCCCTCGT CCCAGGGTCT    1140

GAAAGGGGTG CCAGAGCACC CGGGAAGAGG CCGCGGGCTT CGAAGAGGGC CTTTTCCCTC    1200

GCAGCCCCCG AGCGGTGGTC TGACCCCTAT GCGGAGACCG CGCCCCTAGG ACTAAGGCCA    1260

GGAACAGGGA CCAGCTCCCC CAGGGCCAAT TCACCCTTGG CTCACCCCGC CTTCTCCAGA    1320

CTCCCCCTAT CCCATTTTCA AAGATCAATG AAATAAACGT GCGCGGACTG TCAAAAAAAA    1380

AAAAAAAAA AA                                                         1392
```

(2) INFORMATION FOR SEQ ID NO:2:

(i) SEQUENCE CHARACTERISTICS:
        (A) LENGTH: 906 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..906

(xi) SEQUENCE DESCRIPTION: SEQ ID NO:2:

```
ATG GAG TTT GGG CTG CTT GGT GAG GCA GAG GCG CGA AGC CCT GCG CTG       48
Met Glu Phe Gly Leu Leu Gly Glu Ala Glu Ala Arg Ser Pro Ala Leu
 1               5                  10                  15

TCG TTA TCG GAC GCA GGC ACT CCA CAC CCT CCG CTT CCA GAA CAT GGC       96
Ser Leu Ser Asp Ala Gly Thr Pro His Pro Pro Leu Pro Glu His Gly
            20                  25                  30

TGC AAG GGG CAG GAG CAC AGT GAC TCG GAG AAG GCC TCG GCC TCA CTG      144
Cys Lys Gly Gln Glu His Ser Asp Ser Glu Lys Ala Ser Ala Ser Leu
        35                  40                  45

CCG GGG GGC TCC CCC GAG GAC GGC TCT CTG AAG AAG AAG CAG CGG CGG      192
Pro Gly Gly Ser Pro Glu Asp Gly Ser Leu Lys Lys Lys Gln Arg Arg
```

|  |  |  |  |  |  |  |  |  |  |  |  |  |  |  |  |
|---|---|---|---|---|---|---|---|---|---|---|---|---|---|---|---|
|  |  | 50 |  |  |  | 55 |  |  |  | 60 |  |  |  |  |  |
| CAG | CGC | ACG | CAC | TTC | ACC | AGC | CAG | CAG | CTG | CAG | GAG | CTG | GAG | GCC | ACC |
| Gln | Arg | Thr | His | Phe | Thr | Ser | Gln | Gln | Leu | Gln | Glu | Leu | Glu | Ala | Thr |
| 65 |  |  |  |  | 70 |  |  |  |  | 75 |  |  |  |  | 80 |

240

TTC CAG AGG AAT CGC TAC CCT GAC ATG AGC ACC CGC GAA GAG ATC GCG  288
Phe Gln Arg Asn Arg Tyr Pro Asp Met Ser Thr Arg Glu Glu Ile Ala
              85                  90                  95

GTG TGG ACC AAC CTC ACT GAG GCC CGC GTG CGG GTG TGG TTC AAG AAC  336
Val Trp Thr Asn Leu Thr Glu Ala Arg Val Arg Val Trp Phe Lys Asn
             100                 105                 110

CGG CGC GCC AAG TGG CGG AAG CGG GAG CGC AGC CAG CAG GCG GAG CTG  384
Arg Arg Ala Lys Trp Arg Lys Arg Glu Arg Ser Gln Gln Ala Glu Leu
         115                 120                 125

TGC AAA GGT GGC TTC GCA GCC CCG CTC GGG GGC CTG GTG CCA CCC TAC  432
Cys Lys Gly Gly Phe Ala Ala Pro Leu Gly Gly Leu Val Pro Pro Tyr
     130                 135                 140

GAG GAG GTG TAC CCG GGC TAC TCG TAC GGC AAC TGG CCG CCC AAG GCT  480
Glu Glu Val Tyr Pro Gly Tyr Ser Tyr Gly Asn Trp Pro Pro Lys Ala
145                 150                 155                 160

CTC GCC CCG CCG CTC GCC GCC AAG ACC TTC CCG TTC GCC TTC AAC TCG  528
Leu Ala Pro Pro Leu Ala Ala Lys Thr Phe Pro Phe Ala Phe Asn Ser
                 165                 170                 175

GTC AAC GTG GGG CCT CTG GCT TCA CAG CCT GTA TTC TCA CCG CCC AGC  576
Val Asn Val Gly Pro Leu Ala Ser Gln Pro Val Phe Ser Pro Pro Ser
             180                 185                 190

TCC ATC GCC GCT TCT ATG GTG CCC TCG GCC GCC GCT GCC CCG GGC ACC  624
Ser Ile Ala Ala Ser Met Val Pro Ser Ala Ala Ala Ala Pro Gly Thr
         195                 200                 205

GTA CCA GGT CCC GGA GCC TTG CAG GGC CTG GGC GGG GCA CCC CCC GGG  672
Val Pro Gly Pro Gly Ala Leu Gln Gly Leu Gly Gly Ala Pro Pro Gly
     210                 215                 220

CTG GCT CCA GCC GCC GTG TCC TCC GGG GCA GTG TCC TGC CCT TAC GCC  720
Leu Ala Pro Ala Ala Val Ser Ser Gly Ala Val Ser Cys Pro Tyr Ala
225                 230                 235                 240

TCG GCC GCC GCA GCC GCC GCT GCA GCC GCC TCC TCC CCC TAT GTA TAC  768
Ser Ala Ala Ala Ala Ala Ala Ala Ser Ser Pro Tyr Val Tyr
                 245                 250                 255

CGG GAC CCG TGT AAC TCG AGC CTG GCT AGC CTG CGG CTC AAA GCC AAG  816
Arg Asp Pro Cys Asn Ser Ser Leu Ala Ser Leu Arg Leu Lys Ala Lys
             260                 265                 270

CAG CAC GCC TCT TTC AGC TAT CCC GCC GTG CCC GGG CCG CCG CCG GCC  864
Gln His Ala Ser Phe Ser Tyr Pro Ala Val Pro Gly Pro Pro Pro Ala
         275                 280                 285

GCT AAC CTT AGC CCC TGC CAG TAC GCC GTG GAA CGG CCG GTG          906
Ala Asn Leu Ser Pro Cys Gln Tyr Ala Val Glu Arg Pro Val
     290                 295                 300

(2) INFORMATION FOR SEQ ID NO:3:

(i) SEQUENCE CHARACTERISTICS:
        (A) LENGTH: 302 amino acids
        (B) TYPE: amino acid
        (D) TOPOLOGY: linear (ii) MOLECULE TYPE: protein (xi) SEQUENCE DESCRIPTION: SEQ ID NO:3:

Met Glu Phe Gly Leu Leu Gly Glu Ala Glu Ala Arg Ser Pro Ala Leu
 1               5                  10                  15

Ser Leu Ser Asp Ala Gly Thr Pro His Pro Pro Leu Pro Glu His Gly
             20                  25                  30

```
Cys Lys Gly Gln Glu His Ser Asp Ser Glu Lys Ala Ser Ala Ser Leu
         35                  40                  45

Pro Gly Gly Ser Pro Glu Asp Gly Ser Leu Lys Lys Lys Gln Arg Arg
 50                  55                  60

Gln Arg Thr His Phe Thr Ser Gln Gln Leu Gln Glu Leu Glu Ala Thr
 65                  70                  75                  80

Phe Gln Arg Asn Arg Tyr Pro Asp Met Ser Thr Arg Glu Glu Ile Ala
                 85                  90                  95

Val Trp Thr Asn Leu Thr Glu Ala Arg Val Arg Val Trp Phe Lys Asn
                 100                 105                 110

Arg Arg Ala Lys Trp Arg Lys Arg Glu Arg Ser Gln Gln Ala Glu Leu
                 115                 120                 125

Cys Lys Gly Gly Phe Ala Ala Pro Leu Gly Gly Leu Val Pro Pro Tyr
 130                 135                 140

Glu Glu Val Tyr Pro Gly Tyr Ser Tyr Gly Asn Trp Pro Pro Lys Ala
145                 150                 155                 160

Leu Ala Pro Pro Leu Ala Ala Lys Thr Phe Pro Phe Ala Phe Asn Ser
                 165                 170                 175

Val Asn Val Gly Pro Leu Ala Ser Gln Pro Val Phe Ser Pro Pro Ser
                 180                 185                 190

Ser Ile Ala Ala Ser Met Val Pro Ser Ala Ala Ala Pro Gly Thr
         195                 200                 205

Val Pro Gly Pro Gly Ala Leu Gln Gly Leu Gly Gly Ala Pro Pro Gly
 210                 215                 220

Leu Ala Pro Ala Ala Val Ser Ser Gly Ala Val Ser Cys Pro Tyr Ala
225                 230                 235                 240

Ser Ala Ala Ala Ala Ala Ala Ala Ser Ser Pro Tyr Val Tyr
                 245                 250                 255

Arg Asp Pro Cys Asn Ser Ser Leu Ala Ser Leu Arg Leu Lys Ala Lys
                 260                 265                 270

Gln His Ala Ser Phe Ser Tyr Pro Ala Val Pro Gly Pro Pro Ala
         275                 280                 285

Ala Asn Leu Ser Pro Cys Gln Tyr Ala Val Glu Arg Pro Val
 290                 295                 300
```

(2) INFORMATION FOR SEQ ID NO:4:

(i) SEQUENCE CHARACTERISTICS:
       (A) LENGTH: 1223 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: intron
       (B) LOCATION: 169

(ix) FEATURE:
       (A) NAME/KEY: intron
       (B) LOCATION: 482

(xi) SEQUENCE DESCRIPTION: SEQ ID NO:4:

```
TCCATGGAGT TCGGCCTGCT CAGCGAGGCA GAGGCCCGGA GCCCTGCCCT GTCGCTGTCA      60

GACGCTGGCA CTCCGCACCC CCAGCTCCCA GAGCACGGCT GCAAGGGCCA GGAGCACAGC     120

GGTAAGCGCG CCCCCTTCCG GGGGTGCAGG ACATAACAGC TTCATCCCNG GAGAATATGC     180
```

-continued

```
GCTGGCTTGG GCGCTCTGTG ACCTGCCCCC ACCCTGGCCC CCAGACTCAG AAAAGGCCTC      240

GGCTTCGCTG CCCGGCGGCT CCCCAGAGGA CGGTTCGCTG AAAAAGAAGC AGCGGCGGCA      300

GCGCACGCAC TTCACCAGCC AGCAGCTACA GGAGCTAGAG GCGACCTTCC AGAGGAACCG      360

CTACCCCGAC ATGAGCACGC GCGAGGAGAT CGCCGTGTGG ACAAACCTCA CCGAGGCCCG      420

CGTGCGGGTA TGCTCTCCAG ACCCGCGACT CGCACCCGCG CGGGCCCTCC GCGCTCAGCC      480

TNGCTGGGAC CCGGCCCCGG GCCCTGACCG CCTTTCTCCC GTGCCCGCAG GTGTGGTTCA      540

AGAACCGGCG CGCCAAATGG CGGAAGCGCG AGCGCAGCCA GCAGGCCGAG CTATGCAAAG      600

GCAGCTTCGC GGCGCCGCTC GGGGGGCTGG TGCCGCCCTA CGAGGAGGTG TACCCCGGCT      660

ACTCGTACGG CAACTGGCCG CCCAAGGCTC TTGCCCCGCC GCTCGCCGCC AAGACCTTTC      720

CATTCGCCTT CAACTCGGTC AACGTGGGGC CTCTGGCTTC GCAGCCCGTC TTCTCGCCAC      780

CCAGCTCCAT CGCCGCCTCC ATGGTGCCCT CCGCCGCGGC TGCCCCGGGC ACCGTGCCAG      840

GGCCTGGGGC CCTGCAGGGC CTGGGCGGGG GCCCCCCCGG GCTGGCTCCG GCCGCCGTGT      900

CCTCCGGGGC CGTGTCCTGC CCTTATGCCT CGGCCGCCGC CGCCGCCGCG GCTGCCGCCT      960

CTTCCCCCTA CGTCTATCGG GACCCGTGTA ACTCGAGCCT GGCCAGCCTG CGGCTCAAAG     1020

CCAAACAGCA CGCCTCCTTC AGCTACCCCG CTGTGCACGG GCCGCCCCG GCAGCCAACC     1080

TTAGTCCGTG CCAGTACGCC GTGGAAAGGC CCGTATGAGC GGCCCCGCCC GTAGATCATC     1140

CCCGAGGGCG GGGCAACGA TTCACAGCCT CCGCGGACTG GGGTCATTTT GACTGGCTTG     1200

CTCCCGCCCC AGGGTCTGAA AGG                                             1223
```

(2) INFORMATION FOR SEQ ID NO:5:

(i) SEQUENCE CHARACTERISTICS:
        (A) LENGTH: 1017 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
TCCATGGAGT TCGGCCTGCT CAGCGAGGCA GAGGCCCGGA GCCCTGCCCT GTCGCTGTCA       60

GACGCTGGCA CTCCGCACCC CCAGCTCCCA GAGCACGGCT GCAAGGGCCA GGAGCACAGC      120

GACTCAGAAA AGGCCTCGGC TTCGCTGCCC GGCGGCTCCC CAGAGGACGG TTCGCTGAAA      180

AAGAAGCAGC GGCGGCAGCG CACGCACTTC ACCAGCCAGC AGCTACAGGA GCTAGAGGCG      240

ACCTTCCAGA GGAACCGCTA CCCCGACATG AGCACGCGCG AGGAGATCGC CGTGTGGACA      300

AACCTCACCG AGGCCCGCGT GCGGGTGTGG TTCAAGAACC GGCGCGCCAA ATGGCGGAAG      360

CGCGAGCGCA GCCAGCAGGC CGAGCTATGC AAAGGCAGCT TCGCGGCGCC GCTCGGGGGG      420

CTGGTGCCGC CCTACGAGGA GGTGTACCCC GGCTACTCGT ACGGCAACTG GCCGCCCAAG      480

GCTCTTGCCC CGCCGCTCGC CGCCAAGACC TTTCCATTCG CCTTCAACTC GGTCAACGTG      540

GGGCCTCTGG CTTCGCAGCC CGTCTTCTCG CCACCCAGCT CCATCGCCGC CTCCATGGTG      600

CCCTCCGCCG CGGCTGCCCC GGGCACCGTG CCAGGGCCTG GGGCCCTGCA GGGCCTGGGC      660

GGGGGCCCCC CCGGGCTGGC TCCGGCCGCC GTGTCCTCCG GGGCCGTGTC CTGCCCTTAT      720

GCCTCGGCCG CCGCCGCCGC CGCGGCTGCC GCCTCTTCCC CCTACGTCTA TCGGGACCCG      780

TGTAACTCGA GCCTGGCCAG CCTGCGGCTC AAAGCCAAAC AGCACGCCTC CTTCAGCTAC      840

CCCGCTGTGC ACGGGCCGCC CCCGGCAGCC AACCTTAGTC CGTGCCAGTA CGCCGTGGAA      900
```

```
AGGCCCGTAT GAGCGGCCCC GCCCGTAGAT CATCCCCGAG GGCGGGGGCA ACGATTCACA      960

GCCTCCGCGG ACTGGGGTCA TTTTGACTGG CTTGCTCCCG CCCCAGGGTC TGAAAGG        1017
```

(2) INFORMATION FOR SEQ ID NO:6:

(i) SEQUENCE CHARACTERISTICS:
        (A) LENGTH: 906 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..906

(xi) SEQUENCE DESCRIPTION: SEQ ID NO:6:

```
ATG GAG TTC GGC CTG CTC AGC GAG GCA GAG GCC CGG AGC CCT GCC CTG        48
Met Glu Phe Gly Leu Leu Ser Glu Ala Glu Ala Arg Ser Pro Ala Leu
 1               5                  10                  15

TCG CTG TCA GAC GCT GGC ACT CCG CAC CCC CAG CTC CCA GAG CAC GGC        96
Ser Leu Ser Asp Ala Gly Thr Pro His Pro Gln Leu Pro Glu His Gly
             20                  25                  30

TGC AAG GGC CAG GAG CAC AGC GAC TCA GAA AAG GCC TCG GCT TCG CTG       144
Cys Lys Gly Gln Glu His Ser Asp Ser Glu Lys Ala Ser Ala Ser Leu
         35                  40                  45

CCC GGC GGC TCC CCA GAG GAC GGT TCG CTG AAA AAG AAG CAG CGG CGG       192
Pro Gly Gly Ser Pro Glu Asp Gly Ser Leu Lys Lys Lys Gln Arg Arg
     50                  55                  60

CAG CGC ACG CAC TTC ACC AGC CAG CAG CTA CAG GAG CTA GAG GCG ACC       240
Gln Arg Thr His Phe Thr Ser Gln Gln Leu Gln Glu Leu Glu Ala Thr
 65                  70                  75                  80

TTC CAG AGG AAC CGC TAC CCC GAC ATG AGC ACG CGC GAG GAG ATC GCC       288
Phe Gln Arg Asn Arg Tyr Pro Asp Met Ser Thr Arg Glu Glu Ile Ala
                 85                  90                  95

GTG TGG ACA AAC CTC ACC GAG GCC CGC GTG CGG GTG TGG TTC AAG AAC       336
Val Trp Thr Asn Leu Thr Glu Ala Arg Val Arg Val Trp Phe Lys Asn
            100                 105                 110

CGG CGC GCC AAA TGG CGG AAG CGC GAG CGC AGC CAG CAG GCC GAG CTA       384
Arg Arg Ala Lys Trp Arg Lys Arg Glu Arg Ser Gln Gln Ala Glu Leu
        115                 120                 125

TGC AAA GGC AGC TTC GCG GCG CCG CTC GGG GGG CTG GTG CCG CCC TAC       432
Cys Lys Gly Ser Phe Ala Ala Pro Leu Gly Gly Leu Val Pro Pro Tyr
    130                 135                 140

GAG GAG GTG TAC CCC GGC TAC TCG TAC GGC AAC TGG CCG CCC AAG GCT       480
Glu Glu Val Tyr Pro Gly Tyr Ser Tyr Gly Asn Trp Pro Pro Lys Ala
145                 150                 155                 160

CTT GCC CCG CCG CTC GCC GCC AAG ACC TTT CCA TTC GCC TTC AAC TCG       528
Leu Ala Pro Pro Leu Ala Ala Lys Thr Phe Pro Phe Ala Phe Asn Ser
                165                 170                 175

GTC AAC GTG GGG CCT CTG GCT TCG CAG CCC GTC TTC TCG CCA CCC AGC       576
Val Asn Val Gly Pro Leu Ala Ser Gln Pro Val Phe Ser Pro Pro Ser
            180                 185                 190

TCC ATC GCC GCC TCC ATG GTG CCC TCC GCC GCG GCT GCC CCG GGC ACC       624
Ser Ile Ala Ala Ser Met Val Pro Ser Ala Ala Ala Ala Pro Gly Thr
        195                 200                 205

GTG CCA GGG CCT GGG GCC CTG CAG GGC CTG GGC GGG GCC CCC CGG           672
Val Pro Gly Pro Gly Ala Leu Gln Gly Leu Gly Gly Ala Pro Pro Gly
    210                 215                 220

CTG GCT CCG GCC GCC GTG TCC TCC GGG GCC GTG TCC TGC CCT TAT GCC       720
Leu Ala Pro Ala Ala Val Ser Ser Gly Ala Val Ser Cys Pro Tyr Ala
```

```
                225                 230                 235                 240
TCG GCC GCC GCC GCC GCC GCG GCT GCC GCC TCT TCC CCC TAC GTC TAT           768
Ser Ala Ala Ala Ala Ala Ala Ala Ala Ala Ser Ser Pro Tyr Val Tyr
                    245                 250                 255

CGG GAC CCG TGT AAC TCG AGC CTG GCC AGC CTG CGG CTC AAA GCC AAA           816
Arg Asp Pro Cys Asn Ser Ser Leu Ala Ser Leu Arg Leu Lys Ala Lys
                260                 265                 270

CAG CAC GCC TCC TTC AGC TAC CCC GCT GTG CAC GGG CCG CCC CCG GCA           864
Gln His Ala Ser Phe Ser Tyr Pro Ala Val His Gly Pro Pro Pro Ala
            275                 280                 285

GCC AAC CTT AGT CCG TGC CAG TAC GCC GTG GAA AGG CCC GTA                   906
Ala Asn Leu Ser Pro Cys Gln Tyr Ala Val Glu Arg Pro Val
        290                 295                 300
```

(2) INFORMATION FOR SEQ ID NO:7:

(i) SEQUENCE CHARACTERISTICS:
        (A) LENGTH: 302 amino acids
        (B) TYPE: amino acid
        (D) TOPOLOGY: linear (ii) MOLECULE TYPE: protein (xi) SEQUENCE DESCRIPTION: SEQ ID NO:7:

```
Met Glu Phe Gly Leu Leu Ser Glu Ala Glu Ala Arg Ser Pro Ala Leu
 1               5                  10                  15

Ser Leu Ser Asp Ala Gly Thr Pro His Pro Gln Leu Pro Glu His Gly
                20                  25                  30

Cys Lys Gly Gln Glu His Ser Asp Ser Glu Lys Ala Ser Ala Ser Leu
            35                  40                  45

Pro Gly Gly Ser Pro Glu Asp Gly Ser Leu Lys Lys Lys Gln Arg Arg
        50                  55                  60

Gln Arg Thr His Phe Thr Ser Gln Gln Leu Gln Glu Leu Glu Ala Thr
 65                  70                  75                  80

Phe Gln Arg Asn Arg Tyr Pro Asp Met Ser Thr Arg Glu Glu Ile Ala
                85                  90                  95

Val Trp Thr Asn Leu Thr Glu Ala Arg Val Arg Val Trp Phe Lys Asn
                100                 105                 110

Arg Arg Ala Lys Trp Arg Lys Arg Glu Arg Ser Gln Gln Ala Glu Leu
            115                 120                 125

Cys Lys Gly Ser Phe Ala Ala Pro Leu Gly Gly Leu Val Pro Pro Tyr
        130                 135                 140

Glu Glu Val Tyr Pro Gly Tyr Ser Tyr Gly Asn Trp Pro Pro Lys Ala
145                 150                 155                 160

Leu Ala Pro Pro Leu Ala Ala Lys Thr Phe Pro Phe Ala Phe Asn Ser
                165                 170                 175

Val Asn Val Gly Pro Leu Ala Ser Gln Pro Val Phe Ser Pro Pro Ser
            180                 185                 190

Ser Ile Ala Ala Ser Met Val Pro Ser Ala Ala Ala Pro Gly Thr
        195                 200                 205

Val Pro Gly Pro Gly Ala Leu Gln Gly Leu Gly Gly Pro Pro Gly
    210                 215                 220

Leu Ala Pro Ala Ala Val Ser Ser Gly Ala Val Ser Cys Pro Tyr Ala
225                 230                 235                 240

Ser Ala Ala Ala Ala Ala Ala Ala Ala Ser Ser Pro Tyr Val Tyr
                245                 250                 255

Arg Asp Pro Cys Asn Ser Ser Leu Ala Ser Leu Arg Leu Lys Ala Lys
```

```
                    260                 265                 270
Gln His Ala Ser Phe Ser Tyr Pro Ala Val His Gly Pro Pro Ala
        275                 280                 285
Ala Asn Leu Ser Pro Cys Gln Tyr Ala Val Glu Arg Pro Val
        290                 295                 300

(2) INFORMATION FOR SEQ ID NO:8:

(i) SEQUENCE CHARACTERISTICS:
        (A) LENGTH: 1240 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: join(4..121, 225..427, 531..1148)

(ix) FEATURE:
        (A) NAME/KEY: intron
        (B) LOCATION: 169

(ix) FEATURE:
        (A) NAME/KEY: intron
        (B) LOCATION: 482

(xi) SEQUENCE DESCRIPTION: SEQ ID NO:8:

TCC ATG GAG TTC GGC CTG CTC AGC GAG GCA GAG GCC CGG AGC CCT GCC       48
    Met Glu Phe Gly Leu Leu Ser Glu Ala Glu Ala Arg Ser Pro Ala
     1               5                  10                  15

CTG TCG CTG TCA GAC GCT GGC ACT CCG CAC CCC CAG CTC CCA GAG CAC       96
Leu Ser Leu Ser Asp Ala Gly Thr Pro His Pro Gln Leu Pro Glu His
                 20                  25                  30

GGC TGC AAG GGC CAG GAG CAC AGC G GTAAGCGCGC CCCCTTCCGG              141
Gly Cys Lys Gly Gln Glu His Ser
                35

GGGTGCAGGA CATAACAGCT TCATCCCNGG AGAATATGCG CTGGCTTGGG CGCTCTGTGA    201

CCTGCCCCCA CCCTGGCCCC CAG  AC TCA GAA AAG GCC TCG GCT TCG CTG        250
                         Asp Ser Glu Lys Ala Ser Ala Ser Leu
                              40                  45

CCC GGC GGC TCC CCA GAG GAC GGT TCG CTG AAA AAG AAG CAG CGG CGG      298
Pro Gly Gly Ser Pro Glu Asp Gly Ser Leu Lys Lys Lys Gln Arg Arg
 50                  55                  60

CAG CGC ACG CAC TTC ACC AGC CAG CAG CTA CAG GAG CTA GAG GCG ACC      346
Gln Arg Thr His Phe Thr Ser Gln Gln Leu Gln Glu Leu Glu Ala Thr
 65                  70                  75                  80

TTC CAG AGG AAC CGC TAC CCC GAC ATG AGC ACG CGC GAG GAG ATC GCC      394
Phe Gln Arg Asn Arg Tyr Pro Asp Met Ser Thr Arg Glu Glu Ile Ala
                 85                  90                  95

GTG TGG ACA AAC CTC ACC GAG GCC CGC GTG CGG GTATGCTCTC CAGACCCGCG    447
Val Trp Thr Asn Leu Thr Glu Ala Arg Val Arg
            100                 105

ACTCGCACCC GCGCGGGCCC TCCGCGCTCA GCCTNGCTGG ACCCGGCCC CGGGCCCTGA     507

CCGCCTTTCT CCCGTGCCCG CAG GTG TGG TTC AAG AAC CGG CGC GCC AAA        557
                         Val Trp Phe Lys Asn Arg Arg Ala Lys
                                    110                 115

TGG CGG AAG CGC GAG CGC AGC CAG CAG GCC GAG CTA TGC AAA GGC AGC      605
Trp Arg Lys Arg Glu Arg Ser Gln Gln Ala Glu Leu Cys Lys Gly Ser
            120                 125                 130

TTC GCG GCG CCG CTC GGG GGG CTG GTG CCG CCC TAC GAG GAG GTG TAC      653
Phe Ala Ala Pro Leu Gly Gly Leu Val Pro Pro Tyr Glu Glu Val Tyr
```

```
CCC GGC TAC TCG TAC GGC AAC TGG CCG CCC AAG GCT CTT GCC CCG CCG      701
Pro Gly Tyr Ser Tyr Gly Asn Trp Pro Pro Lys Ala Leu Ala Pro Pro
    150                 155                 160

CTC GCC GCC AAG ACC TTT CCA TTC GCC TTC AAC TCG GTC AAC GTG GGG      749
Leu Ala Ala Lys Thr Phe Pro Phe Ala Phe Asn Ser Val Asn Val Gly
165                 170                 175                 180

CCT CTG GCT TCG CAG CCC GTC TTC TCG CCA CCC AGC TCC ATC GCC GCC      797
Pro Leu Ala Ser Gln Pro Val Phe Ser Pro Pro Ser Ser Ile Ala Ala
                185                 190                 195

TCC ATG GTG CCC TCC GCC GCG GCT GCC CCG GGC ACC GTG CCA GGG CCT      845
Ser Met Val Pro Ser Ala Ala Ala Ala Pro Gly Thr Val Pro Gly Pro
            200                 205                 210

GGG GCC CTG CAG GGC CTG GGG CCC TGC AGG GCC TGG GCG GGG GCC CCC      893
Gly Ala Leu Gln Gly Leu Gly Pro Cys Arg Ala Trp Ala Gly Ala Pro
        215                 220                 225

CCG GGC TGG CTC CGG CCG CCG TGT CCT CCG GGG CCG TGT CCT GCC CTT      941
Pro Gly Trp Leu Arg Pro Pro Cys Pro Pro Gly Pro Cys Pro Ala Leu
    230                 235                 240

ATG CCT CGG CCG CCG CCG CCG CGG CTG CCG CCT CTT CCC CCT ACG          989
Met Pro Arg Pro Pro Pro Pro Arg Leu Pro Pro Leu Pro Pro Thr
245                 250                 255                 260

TCT ATC GGG ACC CGT GTA ACT CGA GCC TGG CCA GCC TGC GGC TCA AAG     1037
Ser Ile Gly Thr Arg Val Thr Arg Ala Trp Pro Ala Cys Gly Ser Lys
                265                 270                 275

CCA AAC AGC ACG CCT CCT TCA GCT ACC CCG CTG TGC ACG GGC CGC CCC     1085
Pro Asn Ser Thr Pro Pro Ser Ala Thr Pro Leu Cys Thr Gly Arg Pro
            280                 285                 290

CGG CAG CCA ACC TTA GTC CGT GCC AGT ACG CCG TGG AAA GGC CCG TAT     1133
Arg Gln Pro Thr Leu Val Arg Ala Ser Thr Pro Trp Lys Gly Pro Tyr
        295                 300                 305

GAG CGG CCC CGC CCG TAGATCATCC CCGAGGGCGG GGGCAACGAT TCACAGCCTC     1188
Glu Arg Pro Arg Pro
    310

CGCGGACTGG GGTCATTTTG ACTGGCTTGC TCCCGCCCCA GGGTCTGAAA GG           1240
```

(2) INFORMATION FOR SEQ ID NO:9:

(i) SEQUENCE CHARACTERISTICS:
        (A) LENGTH: 313 amino acids
        (B) TYPE: amino acid
        (D) TOPOLOGY: linear (ii) MOLECULE TYPE: protein (xi) SEQUENCE DESCRIPTION: SEQ ID NO:9:

```
Met Glu Phe Gly Leu Leu Ser Glu Ala Glu Ala Arg Ser Pro Ala Leu
1               5                   10                  15

Ser Leu Ser Asp Ala Gly Thr Pro His Pro Gln Leu Pro Glu His Gly
                20                  25                  30

Cys Lys Gly Gln Glu His Ser Asp Ser Glu Lys Ala Ser Ala Ser Leu
            35                  40                  45

Pro Gly Gly Ser Pro Glu Asp Gly Ser Leu Lys Lys Gln Arg Arg
    50                  55                  60

Gln Arg Thr His Phe Thr Ser Gln Gln Leu Gln Glu Leu Glu Ala Thr
65                  70                  75                  80

Phe Gln Arg Asn Arg Tyr Pro Asp Met Ser Thr Arg Glu Glu Ile Ala
                85                  90                  95

Val Trp Thr Asn Leu Thr Glu Ala Arg Val Arg Val Trp Phe Lys Asn
```

```
              100                 105                 110
        Arg Arg Ala Lys Trp Arg Lys Arg Glu Arg Ser Gln Gln Ala Glu Leu
                115                 120                 125

Cys Lys Gly Ser Phe Ala Ala Pro Leu Gly Gly Leu Val Pro Pro Tyr
        130                 135                 140

Glu Glu Val Tyr Pro Gly Tyr Ser Tyr Gly Asn Trp Pro Pro Lys Ala
        145                 150                 155                 160

Leu Ala Pro Pro Leu Ala Ala Lys Thr Phe Pro Phe Ala Phe Asn Ser
                        165                 170                 175

Val Asn Val Gly Pro Leu Ala Ser Gln Pro Val Phe Ser Pro Pro Ser
                        180                 185                 190

Ser Ile Ala Ala Ser Met Val Pro Ser Ala Ala Ala Ala Pro Gly Thr
                    195                 200                 205

Val Pro Gly Pro Gly Ala Leu Gln Gly Leu Gly Pro Cys Arg Ala Trp
        210                 215                 220

Ala Gly Ala Pro Pro Gly Trp Leu Arg Pro Pro Cys Pro Pro Gly Pro
        225                 230                 235                 240

Cys Pro Ala Leu Met Pro Arg Pro Pro Pro Pro Arg Leu Pro Pro
                        245                 250                 255

Leu Pro Pro Thr Ser Ile Gly Thr Arg Val Thr Arg Ala Trp Pro Ala
                    260                 265                 270

Cys Gly Ser Lys Pro Asn Ser Thr Pro Pro Ser Ala Thr Pro Leu Cys
                    275                 280                 285

Thr Gly Arg Pro Arg Gln Pro Thr Leu Val Arg Ala Ser Thr Pro Trp
            290                 295                 300

Lys Gly Pro Tyr Glu Arg Pro Arg Pro
        305                 310

(2) INFORMATION FOR SEQ ID NO:10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:10:

GCAGGTCTGT GGATCCAT                                                    18

(2) INFORMATION FOR SEQ ID NO:11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:11:

AAAGGCCCTC TTCGAAGC                                                    18

(2) INFORMATION FOR SEQ ID NO:12:

(i) SEQUENCE CHARACTERISTICS:
            (A) LENGTH: 14 base pairs
            (B) TYPE: nucleic acid
```

```
        (C) STRANDEDNESS: single
        (D) TOPOLOGY: linear (ii) MOLECULE TYPE: DNA (genomic)

(xi) SEQUENCE DESCRIPTION: SEQ ID NO:12:

GKAGCGCGCC CCTT                                                        14

(2) INFORMATION FOR SEQ ID NO:13:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CTTTCTGGCC CTMG                                                        14

(2) INFORMATION FOR SEQ ID NO:14:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GWTGGCCCAC CTG                                                         13

(2) INFORMATION FOR SEQ ID NO:15:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CTCGGATACC CGMG                                                        14

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:16:

CGCACTAGAC CTCCCTCC                                                    18

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

-continued (ii) MOLECULE TYPE: other nucleic acid
        (A) DESCRIPTION: /desc = "oligonucleotide"

(xi) SEQUENCE DESCRIPTION: SEQ ID NO:17:

GGTTATCATC ACTCTCGCTC                                          20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:18:

AGGAATTCCT TGAGGCCCCT                                          20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:19:

CTCATGTCAG GGTAGCGATT                                          20

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:20:

AGGACGGCTC TCTGAAGAA                                           19

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:21:

CCGCAGAGTC ACCAGCTA                                            18

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:22:

TGACAGCCTT TCTCGGATAC                                                    20

(2) INFORMATION FOR SEQ ID NO:23:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:23:

TTGACCGAGT TGAAGGCGAA                                                    20

(2) INFORMATION FOR SEQ ID NO:24:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:24:

TACTCGTACG GCAACTGG                                                      18

(2) INFORMATION FOR SEQ ID NO:25:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:25:

ACGAGGGCAA GCCAGTCTA                                                     19

(2) INFORMATION FOR SEQ ID NO:26:

(i) SEQUENCE CHARACTERISTICS:
            (A) LENGTH: 271 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:26:

Met Glu Thr Asn Cys Arg Lys Leu Val Ser Ala Cys Val Gly Leu Glu
1               5                   10                  15

Lys Asp Lys Gly Gln Gln Gly Lys Asn Glu Asp Val Gly Ala Glu Asp
            20                  25                  30

Pro Ser Lys Lys Lys Arg Gln Arg Arg Gln Arg Thr His Phe Thr Ser
        35                  40                  45

Gln Gln Leu Gln Glu Leu Glu Ala Thr Phe Gln Arg Asn Arg Tyr Pro

```
                50                  55                  60
Asp Met Ser Thr Arg Glu Glu Ile Ala Val Trp Thr Asn Leu Thr Glu
 65                  70                  75                  80

Ala Arg Val Arg Val Trp Phe Lys Asn Arg Arg Ala Lys Trp Arg Lys
                 85                  90                  95

Arg Glu Arg Asn Gln Gln Ala Glu Leu Cys Lys Asn Gly Phe Gly Pro
            100                 105                 110

Gln Phe Asn Gly Leu Met Gln Pro Tyr Asp Asp Met Tyr Pro Gly Tyr
            115                 120                 125

Ser Tyr Asn Asn Trp Ala Ala Lys Gly Leu Thr Ser Ala Ser Leu Ser
130                 135                 140

Thr Lys Ser Phe Pro Phe Phe Asn Ser Met Asn Val Asn Pro Leu Ser
145                 150                 155                 160

Ser Gln Ser Met Phe Ser Pro Pro Asn Ser Ile Ser Ser Met Ser Met
                165                 170                 175

Ser Ser Ser Met Val Pro Ser Ala Val Thr Gly Val Pro Gly Ser Ser
                180                 185                 190

Leu Asn Ser Leu Asn Asn Leu Asn Asn Leu Ser Ser Pro Ser Leu Asn
                195                 200                 205

Ser Ala Val Pro Thr Pro Ala Cys Pro Tyr Ala Pro Pro Thr Pro Pro
210                 215                 220

Tyr Val Tyr Arg Asp Thr Cys Asn Ser Ser Leu Ala Ser Leu Arg Leu
225                 230                 235                 240

Lys Ala Lys Gln His Ser Ser Phe Gly Tyr Ala Ser Val Gln Asn Pro
                245                 250                 255

Ala Ser Asn Leu Ser Ala Cys Gln Tyr Ala Val Asp Arg Pro Val
                260                 265                 270

(2) INFORMATION FOR SEQ ID NO:27:

(i) SEQUENCE CHARACTERISTICS:
        (A) LENGTH: 315 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:27:

Met Asp Ala Phe Lys Gly Gly Met Ser Leu Glu Arg Leu Pro Glu Gly
 1               5                  10                  15

Leu Arg Pro Pro Pro Pro Pro His Asp Met Gly Pro Ser Phe His
                 20                  25                  30

Leu Ala Arg Ala Ala Asp Pro Arg Glu Pro Leu Glu Asn Ser Ala Ser
             35                  40                  45

Glu Ser Ser Asp Ala Asp Leu Pro Asp Lys Glu Arg Gly Gly Glu Ala
 50                  55                  60

Lys Gly Pro Glu Asp Gly Gly Ala Gly Ser Ala Gly Cys Gly Gly Gly
 65                  70                  75                  80

Ala Glu Asp Pro Ala Lys Lys Lys Gln Arg Arg Gln Arg Thr His
                 85                  90                  95

Phe Thr Ser Gln Gln Leu Gln Glu Leu Glu Ala Thr Phe Gln Arg Asn
            100                 105                 110

Arg Tyr Pro Asp Met Ser Met Arg Glu Glu Ile Ala Val Trp Thr Asn
            115                 120                 125

Leu Thr Glu Pro Arg Val Arg Val Trp Phe Lys Asn Arg Arg Ala Lys
```

130                 135                 140
Trp Arg Lys Arg Glu Arg Asn Gln Gln Leu Asp Leu Cys Lys Gly Gly
145                 150                 155                 160

Tyr Val Pro Gln Phe Ser Gly Leu Val Gln Pro Tyr Glu Asp Val Tyr
                165                 170                 175

Ala Ala Gly Tyr Ser Tyr Asn Asn Trp Ala Ala Lys Ser Leu Ala Pro
                180                 185                 190

Ala Pro Leu Ser Thr Lys Ser Phe Thr Phe Phe Asn Ser Met Ser Pro
                195                 200                 205

Leu Ser Ser Gln Ser Met Phe Ser Ala Pro Ser Ser Ile Ser Ser Met
                210                 215                 220

Thr Met Pro Ser Ser Met Gly Pro Gly Ala Val Pro Gly Met Pro Asn
225                 230                 235                 240

Ser Gly Leu Asn Asn Ile Asn Asn Leu Thr Gly Ser Ser Leu Asn Ser
                245                 250                 255

Ala Met Ser Pro Gly Ala Cys Pro Tyr Gly Thr Pro Ala Ser Pro Tyr
                260                 265                 270

Ser Val Tyr Arg Asp Thr Cys Asn Ser Ser Leu Ala Ser Leu Ala Leu
                275                 280                 285

Lys Ser Lys Gln His Ser Ser Phe Gly Tyr Gly Leu Gln Gly Pro
                290                 295                 300

Ala Ser Gly Leu Asn Ala Cys Gln Tyr Asn Ser
305                 310                 315

(2) INFORMATION FOR SEQ ID NO:28:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:28:

GCCCTGCAGG GCCTGGG                                                  17

(2) INFORMATION FOR SEQ ID NO:29:

(i) SEQUENCE CHARACTERISTICS:
        (A) LENGTH: 1223 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: join(4..121, 225..427, 531..1115)

(ix) FEATURE:
        (A) NAME/KEY: intron
        (B) LOCATION: 169

(ix) FEATURE:
        (A) NAME/KEY: intron
        (B) LOCATION: 482

(xi) SEQUENCE DESCRIPTION: SEQ ID NO:29:

TCC ATG GAG TTC GGC CTG CTC AGC GAG GCA GAG GCC CGG ACC CCT GCC    48
    Met Glu Phe Gly Leu Leu Ser Glu Ala Glu Ala Arg Thr Pro Ala
     1              5              10            15

```
CTG TCG CTG TCA GAC GCT GGC ACT CCG CAC CCC CAG CTC CCA GAG CAC      96
Leu Ser Leu Ser Asp Ala Gly Thr Pro His Pro Gln Leu Pro Glu His
             20                  25                  30

GGC TGC AAG GGC CAG GAG CAC AGC G GTAAGCGCGC CCCCTTCCGG              141
Gly Cys Lys Gly Gln Glu His Ser
             35

GGGTGCAGGA CATAACAGCT TCATCCCNGG AGAATATGCG CTGGCTTGGG CGCTCTGTGA    201

CCTGCCCCCA CCCTGGCCCC CAG AC TCA GAA AAG GCC TCG GCT TCG CTG         250
                            Asp Ser Glu Lys Ala Ser Ala Ser Leu
                             40                  45

CCC GGC GGC TCC CCA GAG GAC GGT TCG CTG AAA AAG AAG CAG CGG CGG      298
Pro Gly Gly Ser Pro Glu Asp Gly Ser Leu Lys Lys Lys Gln Arg Arg
 50                  55                  60

CAG CGC ACG CAC TTC ACC AGC CAG CAG CTA CAG GAG CTA GAG GCG ACC      346
Gln Arg Thr His Phe Thr Ser Gln Gln Leu Gln Glu Leu Glu Ala Thr
 65                  70                  75                  80

TTC CAG AGG AAC CGC TAC CCC GAC ATG AGC ACG CGC GAG GAG ATC GCC      394
Phe Gln Arg Asn Arg Tyr Pro Asp Met Ser Thr Arg Glu Glu Ile Ala
                 85                  90                  95

GTG TGG ACA AAC CTC ACC GAG GCC CGC GTG CGG GTATGCTCTC CAGACCCGCG    447
Val Trp Thr Asn Leu Thr Glu Ala Arg Val Arg
            100                 105

ACTCGCACCC GCGCGGGCCC TCCGCGCTCA GCCTNGCTGG GACCCGGCCC CGGGCCCTGA    507

CCGCCTTTCT CCCGTGCCCG CAG GTG TGG TTC AAG AAC CGG CGC GCC AAA        557
                          Val Trp Phe Lys Asn Arg Arg Ala Lys
                                       110                 115

TGG CGG AAG CGC GAG CGC AGC CAG CAG GCC GAG CTA TGC AAA GGC AGC      605
Trp Arg Lys Arg Glu Arg Ser Gln Gln Ala Glu Leu Cys Lys Gly Ser
            120                 125                 130

TTC GCG GCG CCG CTC GGG GGG CTG GTG CCG CCC TAC GAG GAG GTG TAC      653
Phe Ala Ala Pro Leu Gly Gly Leu Val Pro Pro Tyr Glu Glu Val Tyr
            135                 140                 145

CCC GGC TAC TCG TAC GGC AAC TGG CCG CCC AAG GCT CTT GCC CCG CCG      701
Pro Gly Tyr Ser Tyr Gly Asn Trp Pro Pro Lys Ala Leu Ala Pro Pro
150                 155                 160

CTC GCC GCC AAG ACC TTT CCA TTC GCC TTC AAC TCG GTC AAC GTG GGG      749
Leu Ala Ala Lys Thr Phe Pro Phe Ala Phe Asn Ser Val Asn Val Gly
165                 170                 175                 180

CCT CTG GCT TCG CAG CCC GTC TTC TCG CCA CCC AGC TCC ATC GCC GCC      797
Pro Leu Ala Ser Gln Pro Val Phe Ser Pro Pro Ser Ser Ile Ala Ala
                185                 190                 195

TCC ATG GTG CCC TCC GCC GCG GCT GCC CCG GGC ACC GTG CCA GGG CCT      845
Ser Met Val Pro Ser Ala Ala Ala Pro Gly Thr Val Pro Gly Pro
                200                 205                 210

GGG GCC CTG CAG GGC CTG GGC GGG GGC CCC CCC GGG CTG GCT CCG GCC      893
Gly Ala Leu Gln Gly Leu Gly Gly Gly Pro Pro Gly Leu Ala Pro Ala
            215                 220                 225

GCC GTG TCC TCC GGG GCC GTG TCC TGC CCT TAT GCC TCG GCC GCC GCC      941
Ala Val Ser Ser Gly Ala Val Ser Cys Pro Tyr Ala Ser Ala Ala Ala
            230                 235                 240

GCC GCC GCG GCT GCC GCC TCT TCC CCC TAC GTC TAT CGG GAC CCG TGT      989
Ala Ala Ala Ala Ala Ala Ser Ser Pro Tyr Val Tyr Arg Asp Pro Cys
245                 250                 255                 260

AAC TCG AGC CTG GCC AGC CTG CGG CTC AAA GCC AAG CAG CAC GCC TCC     1037
Asn Ser Ser Leu Ala Ser Leu Arg Leu Lys Ala Lys Gln His Ala Ser
                265                 270                 275

TTC AGC TAC CCC GCT GTG CAC GGG CCG CCC CCG GCA GCC AAC CTT AGT     1085
Phe Ser Tyr Pro Ala Val His Gly Pro Pro Pro Ala Ala Asn Leu Ser
```

```
                  280                 285                 290
CCG TGC CAG TAC GCC GTG GAA AGG CCC GTA TGAGCGGCCC CGCCCGTAGA      1135
Pro Cys Gln Tyr Ala Val Glu Arg Pro Val
        295                 300

TCATCCCCGA GGGCGGGGGC AACGATTCAC AGCCTCCGCG GACTGGGGTC ATTTTGACTG  1195

GCTTGCTCCC GCCCCAGGGT CTGAAAGG                                    1223

(2) INFORMATION FOR SEQ ID NO:30:

(i) SEQUENCE CHARACTERISTICS:
        (A) LENGTH: 302 amino acids
        (B) TYPE: amino acid
        (D) TOPOLOGY: linear (ii) MOLECULE TYPE: protein (xi) SEQUENCE DESCRIPTION: SEQ ID NO:30:

Met Glu Phe Gly Leu Leu Ser Glu Ala Glu Ala Arg Thr Pro Ala Leu
  1               5                  10                  15

Ser Leu Ser Asp Ala Gly Thr Pro His Pro Gln Leu Pro Glu His Gly
                 20                  25                  30

Cys Lys Gly Gln Glu His Ser Asp Ser Glu Lys Ala Ser Ala Ser Leu
             35                  40                  45

Pro Gly Gly Ser Pro Glu Asp Gly Ser Leu Lys Lys Lys Gln Arg Arg
 50                  55                  60

Gln Arg Thr His Phe Thr Ser Gln Gln Leu Gln Glu Leu Glu Ala Thr
 65                  70                  75                  80

Phe Gln Arg Asn Arg Tyr Pro Asp Met Ser Thr Arg Glu Glu Ile Ala
                 85                  90                  95

Val Trp Thr Asn Leu Thr Glu Ala Arg Val Arg Val Trp Phe Lys Asn
                100                 105                 110

Arg Arg Ala Lys Trp Arg Lys Arg Glu Arg Ser Gln Gln Ala Glu Leu
            115                 120                 125

Cys Lys Gly Ser Phe Ala Ala Pro Leu Gly Gly Leu Val Pro Pro Tyr
130                 135                 140

Glu Glu Val Tyr Pro Gly Tyr Ser Tyr Gly Asn Trp Pro Pro Lys Ala
145                 150                 155                 160

Leu Ala Pro Pro Leu Ala Ala Lys Thr Phe Pro Phe Ala Phe Asn Ser
                165                 170                 175

Val Asn Val Gly Pro Leu Ala Ser Gln Pro Val Phe Ser Pro Pro Ser
            180                 185                 190

Ser Ile Ala Ala Ser Met Val Pro Ser Ala Ala Ala Pro Gly Thr
            195                 200                 205

Val Pro Gly Pro Gly Ala Leu Gln Gly Leu Gly Gly Pro Pro Gly
            210                 215                 220

Leu Ala Pro Ala Ala Val Ser Ser Gly Ala Val Ser Cys Pro Tyr Ala
225                 230                 235                 240

Ser Ala Ala Ala Ala Ala Ala Ala Ser Ser Pro Tyr Val Tyr
                245                 250                 255

Arg Asp Pro Cys Asn Ser Ser Leu Ala Ser Leu Arg Leu Lys Ala Lys
            260                 265                 270

Gln His Ala Ser Phe Ser Tyr Pro Ala Val His Gly Pro Pro Pro Ala
            275                 280                 285

Ala Asn Leu Ser Pro Cys Gln Tyr Ala Val Glu Arg Pro Val
290                 295                 300
```

(2) INFORMATION FOR SEQ ID NO:31:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

CCAGGGCCTG GGGCCCTGCA GGGCCTGGGC GGGGGC                         36

(2) INFORMATION FOR SEQ ID NO:32:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..48

(xi) SEQUENCE DESCRIPTION: SEQ ID NO:32:

```
CCA GGG CCT GGG GCC CTG CAG GGC CTG GGG CCC TGC AGG GCC TGG GCG     48
Pro Gly Pro Gly Ala Leu Gln Gly Leu Gly Pro Cys Arg Ala Trp Ala
 1               5                  10                  15
```

(2) INFORMATION FOR SEQ ID NO:33:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:33:

```
Pro Gly Pro Gly Ala Leu Gln Gly Leu Gly Pro Cys Arg Ala Trp Ala
 1               5                  10                  15
```